United States Patent
Reddy et al.

(10) Patent No.: US 10,543,200 B2
(45) Date of Patent: Jan. 28, 2020

(54) COMPOSITIONS AND METHODS FOR DRUG SENSITIZATION OF PARASITES

(71) Applicant: The Texas A&M University System, College Station, TX (US)

(72) Inventors: Manchi C M Reddy, College Station, TX (US); James C. Sacchettini, College Station, TX (US); Nian E. Zhou, Naperville, IL (US); Billy F. McCutchen, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/754,244

(22) PCT Filed: Aug. 26, 2016

(86) PCT No.: PCT/US2016/048890
§ 371 (c)(1),
(2) Date: Feb. 21, 2018

(87) PCT Pub. No.: WO2017/035438
PCT Pub. Date: Mar. 2, 2017

(65) Prior Publication Data
US 2018/0243275 A1    Aug. 30, 2018

Related U.S. Application Data

(60) Provisional application No. 62/210,224, filed on Aug. 26, 2015.

(51) Int. Cl.
| | | |
|---|---|---|
| *A61K 31/44* | (2006.01) | |
| *A61K 31/428* | (2006.01) | |
| *A61K 31/4439* | (2006.01) | |
| *A61K 31/454* | (2006.01) | |
| *A61K 31/541* | (2006.01) | |
| *A61P 33/02* | (2006.01) | |
| *A61K 31/423* | (2006.01) | |
| *A61K 31/496* | (2006.01) | |
| *A61K 31/498* | (2006.01) | |
| *A61K 31/501* | (2006.01) | |
| *A61K 31/5377* | (2006.01) | |
| *A61K 31/7036* | (2006.01) | |

(52) U.S. Cl.
CPC ............ *A61K 31/44* (2013.01); *A61K 31/423* (2013.01); *A61K 31/428* (2013.01); *A61K 31/4439* (2013.01); *A61K 31/454* (2013.01); *A61K 31/496* (2013.01); *A61K 31/498* (2013.01); *A61K 31/501* (2013.01); *A61K 31/5377* (2013.01); *A61K 31/541* (2013.01); *A61K 31/7036* (2013.01); *A61P 33/02* (2018.01)

(58) Field of Classification Search
CPC .. A61K 31/44; A61K 31/428; A61K 31/4439; A61K 31/454; A61K 33/02; A61K 41/496; A61K 31/498; A61K 31/501; A61K 31/5377; A61K 31/7036
See application file for complete search history.

(56) References Cited

U.S. PATENT DOCUMENTS

| | | | |
|---|---|---|---|
| 2005/0142113 A1 | 6/2005 | Mcleod et al. | |
| 2007/0105848 A1* | 5/2007 | Wood | A61K 31/185 |
| | | | 514/224.5 |
| 2009/0197943 A1 | 8/2009 | Chan et al. | |

FOREIGN PATENT DOCUMENTS

| | | | |
|---|---|---|---|
| WO | WO 88/04294 | * | 6/1988 |
| WO | 2012/135064 | | 10/2012 |
| WO | 2015/127089 | | 8/2015 |
| WO | 2015/131019 | | 9/2015 |

OTHER PUBLICATIONS

Zuther et al. (PNAS, 9(96), 1999; 13387-13392).*
Qian et al. (parasitlolgy International 64; 597-602 (2015) first publishing on line Aug. 8, 2015.*
International Search Report and Written Opinion for International application No. PCT/US2016/48890, dated Nov. 4, 2016, 15 pages.
Office Action for Eurasian Patent Application No. 201890575, dated Oct. 26, 2018; 4 pages.
Partial Supplementary European Search Report for European Patent Application No. 16840186.7, dated Mar. 7, 2019; 15 pages.

\* cited by examiner

*Primary Examiner* — Shirley V Gembeh
(74) *Attorney, Agent, or Firm* — Baker Botts L.L.P.

(57) ABSTRACT

Compositions and methods for inhibiting and/or sensitizing or re-sensitizing a parasite to an antiparasitic drug are provided. The compositions can comprise a an arylphenoxy-propionate derivative, an aryloxyphenoxyacetate derivative, an aryloxyphenylacetate derivative, one or more substituted quinols, or a pharmaceutically acceptable salt, hydrate, or prodrug thereof, or a combination thereof in an amount and formulation sufficient to sensitize the parasite to the drug, treating infection of a patient by a parasite with a drug, or to prevent symptomatic infection of a patient by a parasite with a drug.

8 Claims, 4 Drawing Sheets

EFFICACY OF NZ 369 VS C. PARVUM DIARRHEA: AVERAGE DAILY FECAL VOLUME $p < 0.001; R^2 = 0.262$

COMPOSITIONS AND METHODS FOR DRUG SENSITIZATION OF PARASITES

CROSS-REFERENCE TO RELATED APPLICATIONS

This application is a national phase of International Application No. PCT/US2016/048890 filed Aug. 26, 2016 which claims priority to U.S. Provisional Patent Application Ser. No. 62/210,224, filed Aug. 26, 2015, all of which are hereby incorporated by reference in their entirety.

TECHNICAL FIELD

The present disclosure relates to compositions for parasite inhibition and/or sensitization or re-sensitization of a parasite to another drug or combination of drugs. In particular, it relates to compositions including one or more arylphenoxypropionate derivatives, such as, but not limited to, quizalofop, fenoxaprop, proquizalofop, and haloxyfop, one or more aryloxyphenoxyacetate derivatives, one or more aryloxyphenylacetate derivatives, and one or more substituted quinols, and combinations thereof. The present disclosure also relates to methods of parasite inhibition and/or sensitizing or re-sensitizing a parasite to another drug or combination of drugs by applying more arylphenoxypropionate derivatives to the parasite.

BACKGROUND

Parasitic infection is treated, or prevented, by the administration of a drug or drugs, such as xenobiotic chemotherapeutic drugs, to a susceptible or infected host organism. Effective treatment of parasitic infection by drug administration is frequently impaired, however, due to resistance of the parasite to the drug. Such resistance can be "inherent" to the parasite in the sense that the susceptibility of the parasite to the drug has not increased due to widespread use of the drug. Commonly, however, drug resistance of infectious parasites is observed due to evolved resistance associated with widespread treatment with the drug and associated selection pressure for resistant phenotypes. Currently, many infectious parasites are completely or highly resistant to available drugs and drug combinations, and parasites still susceptible to available drugs require treatment with greater doses than previously required, such that complete or effectively complete resistance is foreseeable.

For example, chloroquine resistance in certain species of malaria-causing *Plasmodium* parasites is so widespread that alternative or combination anti-malarial therapies are now required, and many parasitic species, including malaria-causing *Plasmodium* species, are now multi-drug resistant. As a further example, the incidence of parasite resistance to avermectins, a widely used class of nematicides, acaricides and insecticides in veterinary and human medicine and plant protection, is increasing.

Resistance of infectious parasites to anti-parasitic drugs can be avoided or lessened by rendering the parasites more sensitive to one or more drugs. The calcium channel blocker Verapramil, for example, has been evaluated for its effect on sensitization of parasites to xenobiotics. However, safe, economical, and effective methods for sensitizing parasites in such a manner are lacking.

SUMMARY

Compositions and methods for inhibiting and/or sensitizing or re-sensitizing a parasite to an antiparasitic drug are provided. The compositions can comprise a an arylphenoxypropionate derivative, an aryloxyphenoxyacetate derivative, an aryloxyphenylacetate derivative, one or more substituted quinols, or a pharmaceutically acceptable salt, hydrate, or prodrug thereof, or a combination thereof in an amount and formulation sufficient to sensitize the parasite to the drug, treating infection of a patient by a parasite with a drug, or to prevent symptomatic infection of a patient by a parasite with a drug.

BRIEF DESCRIPTION OF THE DRAWINGS

A more complete understanding of the present embodiments and advantages thereof may be acquired by referring to the following description taken in conjunction with the accompanying drawings, which depict embodiments of the present disclosure, and in which like numbers refer to similar components, and in which.

DETAILED DESCRIPTION

Figure 1:
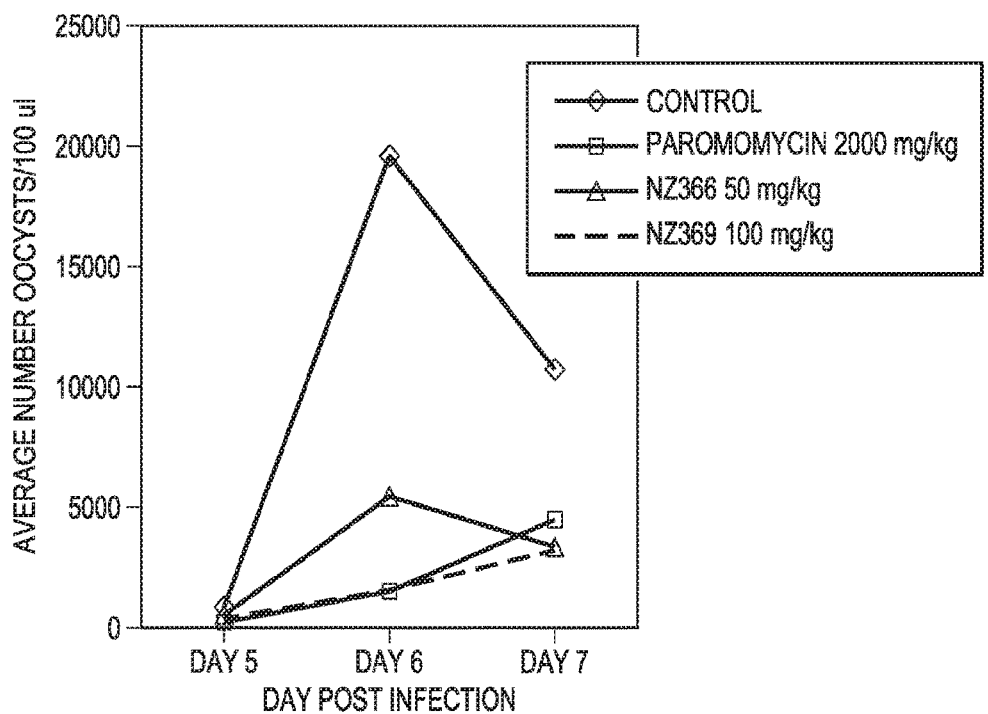
FIG. 1 is a graph of oocyst numbers vs. days post infection in mice with Cryptosporodosis treated with a control or test compounds.

The present disclosure relates to compositions and methods for inhibition and/or drug-sensitization of a parasite. These compositions and methods are described in further detail below.

Unless otherwise indicated by the specific context of this specification, a parasite can include any type of parasite, or any part thereof. Furthermore, it can include a parasite in a host organism, or outside a host organism, such as in the environment occupied by an organism susceptible to infection by the parasite. The organism or host organism can be any animal. By way of example, and not limitation, the organism or host organism can be a mammal, such as a human, a pet mammal such as a dog or cat, an agricultural mammal, such as a horse, cow, pig, sheep, or goat, or a zoo mammal.

Although many embodiments herein are described with reference to a single parasite, the present disclosure is not so limited. The present disclosure encompasses, for example, infections of a single host animal with a plurality of parasites of the same species and with a plurality of parasites of different species, concurrently or otherwise. These embodiments and others will be readily apparent to one of ordinary skill in the art in view of the present disclosure.

Drug-sensitization, unless otherwise indicated by the specific context of this specification, can include increased sensitivity to a drug, decreased resistance to a drug, or potentiation of a drug's activity or efficacy. Any effect can be measured using any methods accepted in the art. In certain embodiments, drug-sensitization can be determined by an increased ability of the drug to inhibit a parasite. Parasitic inhibition can include killing the parasite, rendering the parasite more susceptible to the immune system of a host organism, arresting the parasite in a phase of its life cycle that is relatively benign with respect to the host organism, reducing the rate of propagation of the parasite in the host organism, or otherwise negatively affecting a parasite. An increased ability of the drug to inhibit a parasite can be demonstrated by, for example, an ability to inhibit the cell with a reduced amount of drug or in a shorter period of time than in the absence of drug-sensitization. In the case of drug-resistant parasites, which include parasites with inherent or acquired resistance, drug-sensitization can result in a renewed, restored, restored or newly acquired ability of the drug to inhibit a parasite or type of parasite.

Administration to a parasite, unless otherwise indicated by the specific context of this specification, can include administration directly to a parasite or indirect administration to a parasite, such as by direct or indirect administration to a host organism infected by the parasite or by prophylactic administration to an organism susceptible to infection by the parasite, or such as by administration to the environment of the parasite, such as by administration to an environment of the parasite. By way of example and not limitation, administration to a parasite can include, in addition to directly contacting the parasite with the composition administered, oral, enteral, and parenteral administration to an infected or susceptible host, as well as administration of the compound to a body of or source of water, for example, in which the parasite resides or will reside, as well as administration of the compound to a substrate or fomite upon which the parasite resides or will reside, or upon which another host or susceptible host organism resides or will reside, such as, for example, a mosquito netting, a portion of a plant such as a leaf, or a consumer product that can come into close contact with the skin of a human or animal, such as a bedsheet, a protective athletic garment, or a harness. By way of further example, the compositions of the present disclosure can be administered to a susceptible animal or infected host in the form of aerosolized particles, e.g., by way of aerosolizer, nebulizer or other like device, or transdermally, or transbucally, or sublingually, or by subcutaneous administration, or any other method of drug delivery, and any combination thereof.

Compositions

The present disclosure includes parasite drug-sensitization compositions, including one or more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof.

In certain embodiments, the present disclosure provides arylphenoxypropionate derivatives according to one of the following structures:

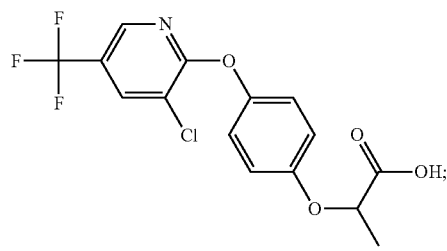

haloxyfop (IUPAC name: (RS)-2-{4-[3-chloro-5-(trifluoromethyl)-2-pyridyloxy]phenoxy}propionic acid)

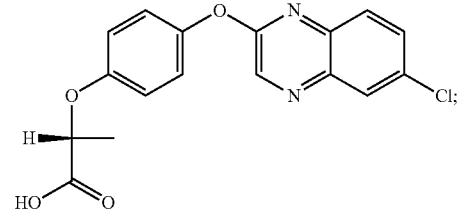

quizalofop-p (IUPAC name: (R)-2-[4-(6-chloroquinoxalin-2-yloxy)phenoxy]propionic acid)

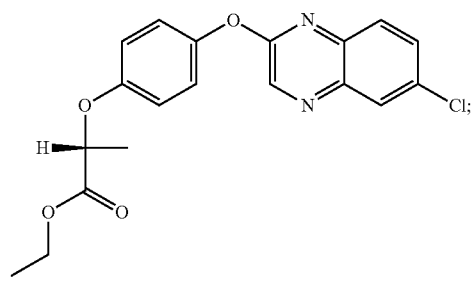

quizalofop-p-ethyl (IUPAC name: ethyl (2R)-2-[4-(6-chloroquinoxalin-2-yloxy)phenoxy]propionate)

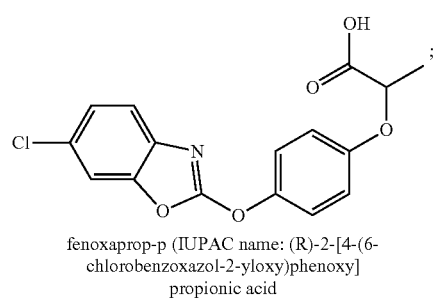

fenoxaprop-p (IUPAC name: (R)-2-[4-(6-chlorobenzoxazol-2-yloxy)phenoxy]propionic acid and enantiomers of the general structures.

In certain embodiments, the present disclosure provides aryloxyphenoxyacetate derivatives according to the following structure:

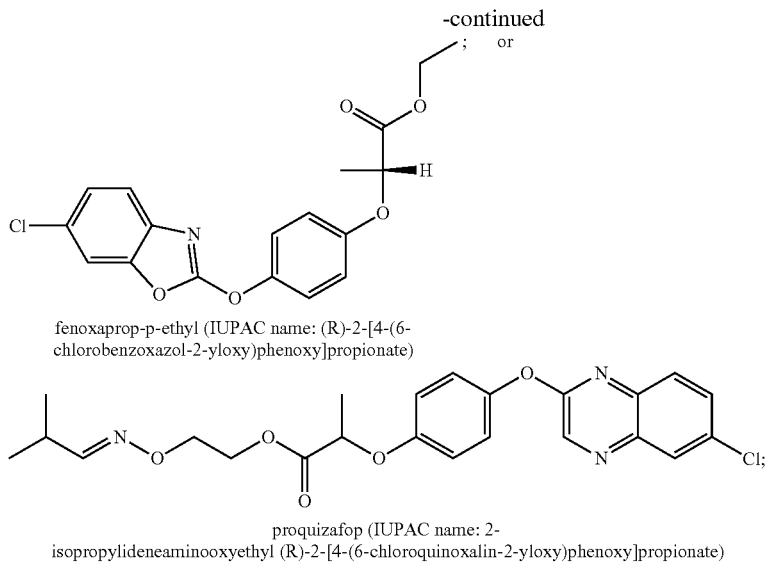

fenoxaprop-p-ethyl (IUPAC name: (R)-2-[4-(6-chlorobenzoxazol-2-yloxy)phenoxy]propionate)

proquizafop (IUPAC name: 2-isopropylideneaminooxyethyl (R)-2-[4-(6-chloroquinoxalin-2-yloxy)phenoxy]propionate)

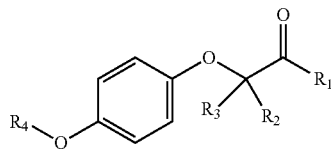

wherein $R_1$ is selected from $-OR_5$, $-NR_6R_7$ and $-NH-SO_2-R_8$ groups, $R_2$ and $R_3$ are independently selected from hydrogen, alkyl, alkenyl, alkynyl, cycloalkyl, aryl, and heteroaryl groups; or $R_2$ and $R_3$ together are a cycloalkyl group; $R_4$ is selected from the group consisting of aryl, heteroaryl, bicycloaryl, and bicycloheteroaryl groups optionally additionally substituted with from zero to four substitutions selected independently from halogen, hydroxyl, alkyl, alkoxy, nitril, nitro, amino, alkylamino, dialkylamino, dialkylaminoalkyl, carboxy, acyl, carboxamido, alkylsulfoxide, acylamino, phenyl, benzyl, phenoxy, and benzyloxy groups; $R_5$ is selected from hydrogen or an alkyl, aryl, or benzyl group that is optionally additionally substituted with an alkyloxy, alkylamino, dialkylamino, or acylamino group; $R_6$ and $R_7$ are independently selected from hydrogen, alkyl, alkenyl, alkynyl, cycloalkyl, heterocycloalkyl, aryl, heteroaryl, and alkoxy groups; or $R_6$ and $R_7$ together are a cycloalkyl or heterocycloalkyl group; and $R_8$ is an alkyl or aryl group optionally substituted with halogen.

In certain embodiments, the present disclosure provides aryloxyphenylacetate derivatives according to the following structure:

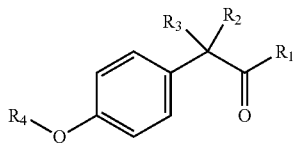

wherein $R_1$ is selected from $-OR_5$, $-NR_6R_7$ and $-NH-SO_2-R_8$ groups, $R_2$ and $R_3$ are independently selected from hydrogen, alkyl, alkenyl, alkynyl, cycloalkyl, aryl, and heteroaryl groups; or $R_2$ and $R_3$ together are a cycloalkyl group; $R_4$ is selected from the group consisting of aryl, heteroaryl, bicycloaryl, and bicycloheteroaryl groups optionally additionally substituted with from zero to four substitutions selected independently from halogen, hydroxyl, alkyl, alkoxy, nitril, nitro, amino, alkylamino, dialkylamino, dialkylaminoalkyl, carboxy, acyl, carboxamido, alkylsulfoxide, acylamino, phenyl, benzyl, phenoxy, and benzyloxy groups; $R_5$ is selected from hydrogen or an alkyl, aryl, or benzyl group that is optionally additionally substituted with an alkyloxy, alkylamino, dialkylamino, or acylamino group; $R_6$ and $R_7$ are independently selected from hydrogen, alkyl, alkenyl, alkynyl, cycloalkyl, heterocycloalkyl, aryl, heteroaryl, and alkoxy groups; or $R_6$ and $R_7$ together are a cycloalkyl or heterocycloalkyl group; and $R_8$ is an alkyl or aryl group optionally substituted with halogen.

In certain embodiments, the present disclosure provides substituted quinols according to the following structure:

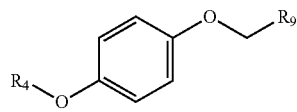

wherein $R_9$ is selected from nitril, hydroxyl, heterocycloaryl and alkyloxy groups; and $R_4$ is selected from the group consisting of aryl, heteroaryl, bicycloaryl, and bicycloheteroaryl groups optionally additionally substituted with from zero to four substitutions chosen independently from the group consisting of halogen, hydroxyl, alkyl, alkyloxy, nitril, nitro, amino, alkylamino, dialkylamino, dialkylaminoalkyl, carboxy, acyl, carboxamido, alkylsulfoxide, acylamino, phenyl, benzyl, phenoxy, and benzyloxy groups.

Specific compounds of the invention include those named in Table 1 and characterized in the examples herein.

TABLE 1

| | Arylphenoxypropionate Derivatives | |
|---|---|---|
| WuXi-N8 | | 1-{5-[(6-chloro-1,3-benzothiazol-2-yl)oxy]pyridin-2-yl}-3-(propan-2-yl)urea |
| WuXi-N7 | | 1-{6-[(6-chloro-1,3-benzothiazol-2-yl)oxy]pyridazin-3-yl}-3-(propan-2-yl)urea |
| WuXi-N6 | | 1-{6-[(6-chloro-1,3-benzothiazol-2-yl)oxy]pyridin-3-yl}-3-(propan-2-yl)urea |
| WUXI-N5 | | 3-{4-[(6-chloro-1,3-benzothiazol-2-yl)oxy]piperidin-1-yl}-N-methoxypropanamide |
| WUXI-N4 | | 2-{4-[(6-chloro-1,3-benzothiazol-2-yl)oxy]piperidin-1-yl}-N-methoxyacetamide |
| quizalofop-p-ethyl | | ethyl (2R)-2-{4-[(6-chloroquinoxalin-2-yl)oxy]phenoxy}propanoate |
| quizalofop-p | | (2R)-2-{4-[(6-chloroquinoxalin-2-yl)oxy]phenoxy}propanoic acid |

TABLE 1-continued

Arylphenoxypropionate Derivatives

| | | |
|---|---|---|
| propaquizafop | 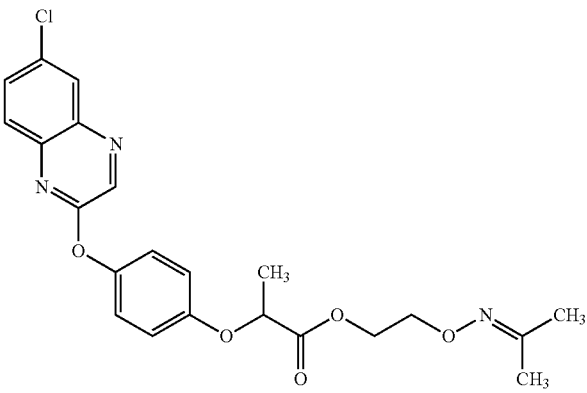 [SMILES: CC(C)=NOCCOC(=O)C(C)Oc1ccc(Oc2cnc3cc(Cl)ccc3n2)cc1] | 2-{[(propan-2-ylidene)amino]oxy}ethyl 2-{4-[(6-chloroquinoxalin-2-yl)oxy]phenoxy}propanoate |
| NZ-578 | 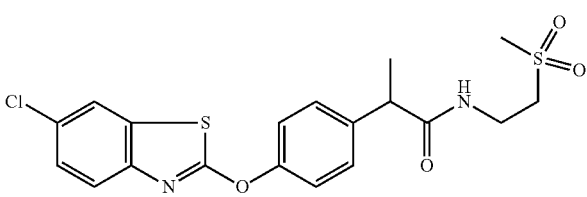 [SMILES: CC(C(=O)NCCS(C)(=O)=O)c1ccc(Oc2nc3ccc(Cl)cc3s2)cc1] | 2-{4-[(6-chloro-1,3-benzothiazol-2-yl)oxy]phenyl}-N-(2-methanesulfonylethyl)propanamide |
| NZ-577 | 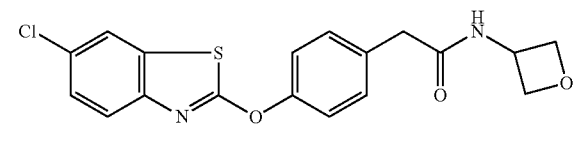 [SMILES: O=C(Cc1ccc(Oc2nc3ccc(Cl)cc3s2)cc1)NC1COC1] | 2-{4-[(6-chloro-1,3-benzothiazol-2-yl)oxy]phenyl}-N-(oxetan-3-yl)acetamide |
| NZ-576 | 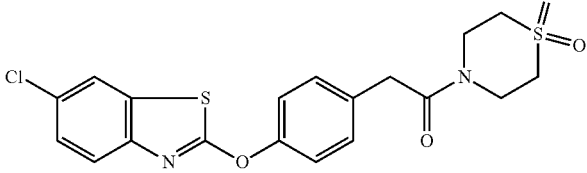 | 4-(2-{4-[(6-chloro-1,3-benzothiazol-2-yl)oxy]phenyl}acetyl)-1λ$^6$,4-thiomorpholine-1,1-dione |
| NZ-575 | 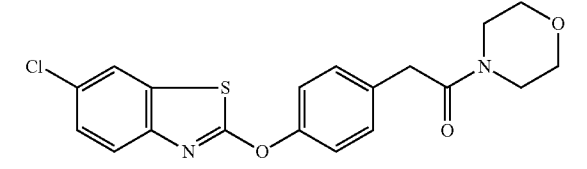 [SMILES: O=C(Cc1ccc(Oc2nc3ccc(Cl)cc3s2)cc1)N1CCOCC1] | 2-{4-[(6-chloro-1,3-benzothiazol-2-yl)oxy]phenyl}-1-(morpholin-4-yl)ethan-1-one |
| NZ-574 | 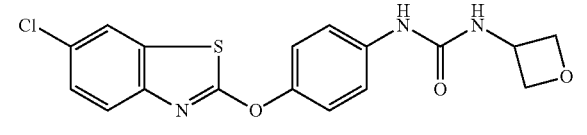 [SMILES: O=C(Nc1ccc(Oc2nc3ccc(Cl)cc3s2)cc1)NC1COC1] | 1-{4-[(6-chloro-1,3-benzothiazol-2-yl)oxy]phenyl}-3-(oxetan-3-yl)urea |
| NZ-573 | 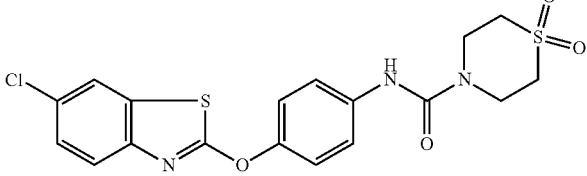 | N-{4-[(6-chloro-1,3-benzothiazol-2-yl)oxy]phenyl}-1,1-dioxo-1λ$^6$,4-thiomorpholine-4-carboxamide |
| NZ-572 | 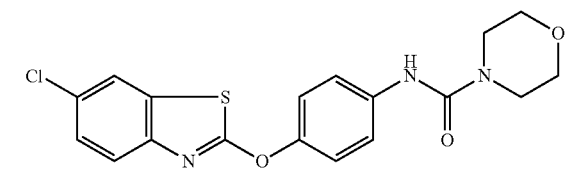 [SMILES: O=C(Nc1ccc(Oc2nc3ccc(Cl)cc3s2)cc1)N1CCOCC1] | N-{4-[(6-chloro-1,3-benzothiazol-2-yl)oxy]phenyl}morpholine-4-carboxamide |

TABLE 1-continued

Arylphenoxypropionate Derivatives

NZ-564 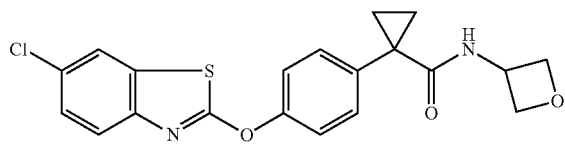 [SMILES: O=C(NC1COC1)C1(c2ccc(Oc3nc4ccc(Cl)cc4s3)cc2)CC1] 1-{4-[(6-chloro-1,3-benzothiazol-2-yl)oxy]phenyl}-N-(oxetan-3-yl)cyclopropane-1-carboxamide NZ-563 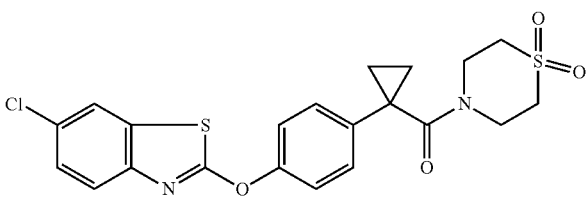 [SMILES: O=C(N1CCS(=O)(=O)CC1)C1(c2ccc(Oc3nc4ccc(Cl)cc4s3)cc2)CC1] 4-(1-{4-[(6-chloro-1,3-benzothiazol-2-yl)oxy]phenyl}cyclopropanecarbonyl)-1$\lambda^6$,4-thiomorpholine-1,1-dione NZ-562 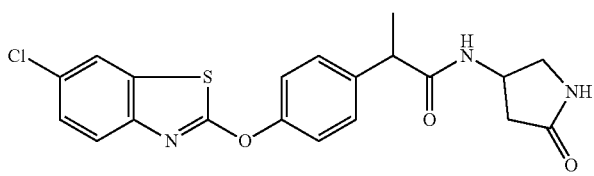 [SMILES: CC(C(=O)NC1CNC(=O)C1)c1ccc(Oc2nc3ccc(Cl)cc3s2)cc1] 2-{4-[(6-chloro-1,3-benzothiazol-2-yl)oxy]phenyl}-N-(5-oxopyrrolidin-3-yl)propanamide NZ-561 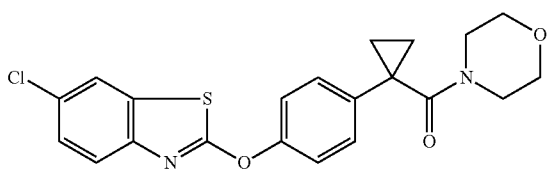 [SMILES: O=C(N1CCOCC1)C1(c2ccc(Oc3nc4ccc(Cl)cc4s3)cc2)CC1] 6-chloro-2-{4-[1-(morpholine-4-carbonyl)cyclopropyl]phenoxy}-1,3-benzothiazole NZ-560 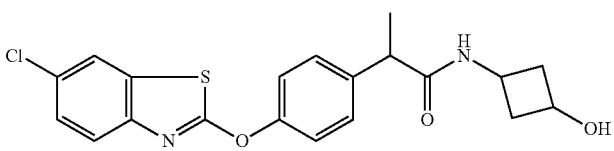 [SMILES: CC(C(=O)NC1CC(O)C1)c1ccc(Oc2nc3ccc(Cl)cc3s2)cc1] 2-{4-[(6-chloro-1,3-benzothiazol-2-yl)oxy]phenyl}-N-(3-hydroxycyclobutyl)propanamide NZ-559 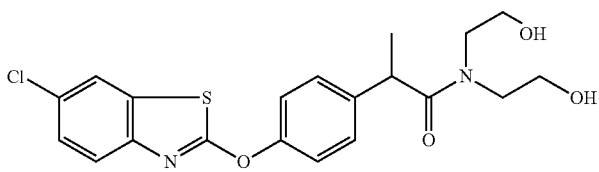 [SMILES: CC(C(=O)N(CCO)CCO)c1ccc(Oc2nc3ccc(Cl)cc3s2)cc1] 2-{4-[(6-chloro-1,3-benzothiazol-2-yl)oxy]phenyl}-N,N-bis(2-hydroxyethyl)propanamide NZ-558 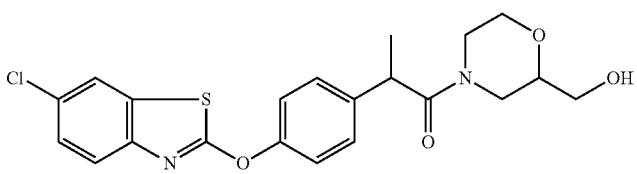 [SMILES: CC(C(=O)N1CCOC(CO)C1)c1ccc(Oc2nc3ccc(Cl)cc3s2)cc1] 2-{4-[(6-chloro-1,3-benzothiazol-2-yl)oxy]phenyl}-1-[2-(hydroxymethyl)morpholin-4-yl]propan-1-one NZ-557 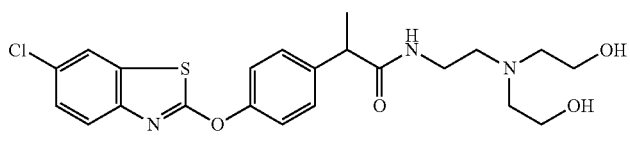 [SMILES: CC(C(=O)NCCN(CCO)CCO)c1ccc(Oc2nc3ccc(Cl)cc3s2)cc1] N-{2-[bis(2-hydroxyethyl)amino]ethyl}-2-{4-[(6-chloro-1,3-benzothiazol-2-yl)oxy]phenyl}propanamide NZ-556 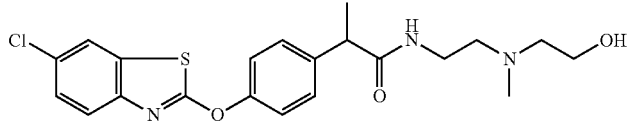 [SMILES: CC(C(=O)NCCN(C)CCO)c1ccc(Oc2nc3ccc(Cl)cc3s2)cc1] 2-{4-[(6-chloro-1,3-benzothiazol-2-yl)oxy]phenyl}-N-{2-[(2-hydroxyethyl)(methyl)amino]ethyl}propanamide TABLE 1-continued Arylphenoxypropionate Derivatives

| | | |
|---|---|---|
| NZ-555 | | 2-{4-[(6-chloro-1,3-benzothiazol-2-yl)oxy]phenyl}-1-[3-(hydroxymethyl)morpholin-4-yl]propan-1-one |
| NZ-554 | | 4-(2-{4-[(6-chloro-1,3-benzothiazol-2-yl)oxy]phenyl}propanoyl)morpholine-2-carboxamide |
| NZ-553 | | 4-(2-{4-[(6-chloro-1,3-benzothiazol-2-yl)oxy]phenyl}propanoyl)-1$\lambda^6$,4-thiomorpholine-1,1-dione |
| NZ-550 | | 2-{4-[(6-chloroquinoxalin-2-yl)oxy]phenyl}-N-[2-(methylamino)ethyl]propanamide |
| NZ-548 | | 2-{4-[(6-chloro-1,3-benzothiazol-2-yl)oxy]phenyl}-N-[2-(methylamino)ethyl]propanamide |
| NZ-547 | | 2-{4-[(6-chloro-1,3-benzothiazol-2-yl)oxy]phenyl}-N-[2-(dimethylamino)ethyl]-N-methylpropanamide |
| NZ-546 | | N-[2-(dimethylamino)ethyl]-2,2-difluoro-2-{4-[(6-fluoro-1,3-benzothiazol-2-yl)oxy]phenyl}acetamide |
| NZ-545 | | 2,2-difluoro-2-{4-[(6-fluoro-1,3-benzothiazol-2-yl)oxy]phenyl}-1-(4-methylpiperazin-1-yl)ethan-1-one |
| NZ-544 | | 2-{4-[(6-chloro-1,3-benzothiazol-2-yl)oxy]phenyl}-N-(oxolan-3-yl)propanamide |

TABLE 1-continued

| Arylphenoxypropionate Derivatives | | |
|---|---|---|
| NZ-543 | | 2-{4-[(6-chloro-1,3-benzothiazol-2-yl)oxy]phenyl}-N-(oxetan-3-yl)propanamide |
| NZ-542 | | 2-{4-[(6-chloro-1,3-benzothiazol-2-yl)oxy]phenyl}-N-(1,3-dimethoxypropan-2-yl)propanamide |
| NZ-541 | | 2-{4-[(6-chloro-1,3-benzothiazol-2-yl)oxy]phenyl}-N-(2-methoxyethyl)propanamide |
| NZ-539 | | 2-{4-[(6-chloro-1,3-benzothiazol-2-yl)oxy]phenyl}-N-cyclobutylpropanamide |
| NZ-538 | | 2-{4-[(6-chloro-1,3-benzothiazol-2-yl)oxy]phenyl}-N-cyclopropylpropanamide |
| NZ-537 | | 2-{4-[(6-chloroquinoxalin-2-yl)oxy]phenyl}-1-(piperazin-1-yl)propan-1-one |
| NZ-536 | | 2-{4-[(6-chloroquinoxalin-2-yl)oxy]phenyl}-N-(1,3-dihydroxypropan-2-yl)propanamide |
| NZ-535 | | 2-{4-[(6-chloroquinoxalin-2-yl)oxy]phenyl}-N-[2-(dimethylamino)ethyl]propanamide |
| NZ-534 | | 2-{4-[(6-chloroquinoxalin-2-yl)oxy]phenyl}-N-(2,3-dihydroxypropyl)propanamide |
| NZ-533 | | 2-{4-[(6-chloroquinoxalin-2-yl)oxy]phenyl}-N-(2-hydroxyethyl)propanamide |

TABLE 1-continued

Arylphenoxypropionate Derivatives

| | | |
|---|---|---|
| NZ-532 | 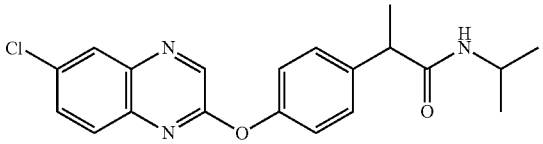 [SMILES: CC(C)NC(=O)C(C)c1ccc(Oc2cnc3cc(Cl)ccc3n2)cc1] | 2-{4-[(6-chloroquinoxalin-2-yl)oxy]phenyl}-N-(propan-2-yl)propanamide |
| NZ-531 | 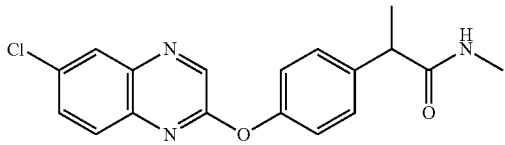 [SMILES: CNC(=O)C(C)c1ccc(Oc2cnc3cc(Cl)ccc3n2)cc1] | 2-{4-[(6-chloroquinoxalin-2-yl)oxy]phenyl}-N-methylpropanamide |
| NZ-530 | 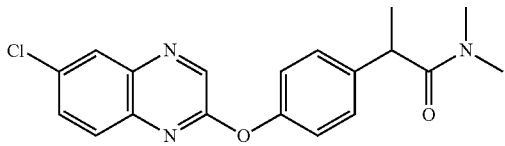 [SMILES: CC(C(=O)N(C)C)c1ccc(Oc2cnc3cc(Cl)ccc3n2)cc1] | 2-{4-[(6-chloroquinoxalin-2-yl)oxy]phenyl}-N,N-dimethylpropanamide |
| NZ-529 | 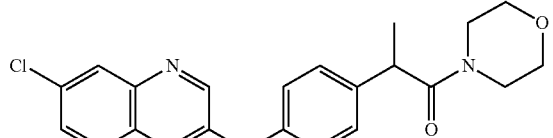 | 2-{4-[(6-chloroquinoxalin-2-yl)oxy]phenyl}-1-(morpholin-4-yl)propan-1-one |
| NZ-522 | 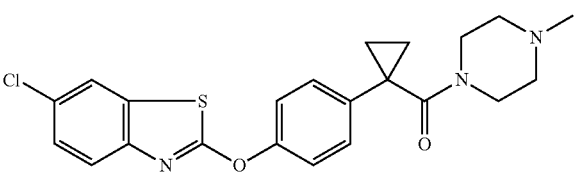 [SMILES: CN1CCN(C(=O)C2(c3ccc(Oc4nc5ccc(Cl)cc5s4)cc3)CC2)CC1] | 6-chloro-2-{4-[1-(4-methylpiperazine-1-carbonyl)cyclopropyl]phenoxy}-1,3-benzothiazole |
| NZ-521 | 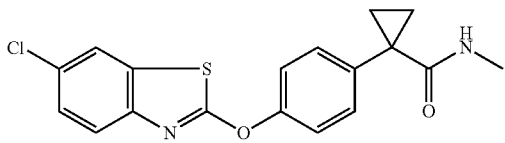 [SMILES: CNC(=O)C1(c2ccc(Oc3nc4ccc(Cl)cc4s3)cc2)CC1] | 1-{4-[(6-chloro-1,3-benzothiazol-2-yl)oxy]phenyl}-N-methylcyclopropane-1-carboxamide |
| NZ-518 | 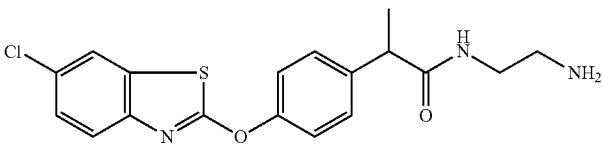 [SMILES: CC(C(=O)NCCN)c1ccc(Oc2nc3ccc(Cl)cc3s2)cc1] | N-(2-aminoethyl)-2-{4-[(6-chloro-1,3-benzothiazol-2-yl)oxy]phenyl}propanamide |
| NZ-516 | 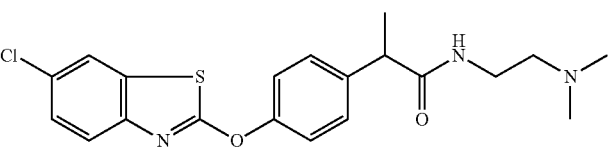 [SMILES: CC(C(=O)NCCN(C)C)c1ccc(Oc2nc3ccc(Cl)cc3s2)cc1] | 2-{4-[(6-chloro-1,3-benzothiazol-2-yl)oxy]phenyl}-N-[2-(dimethylamino)ethyl]propanamide |
| NZ-513 | 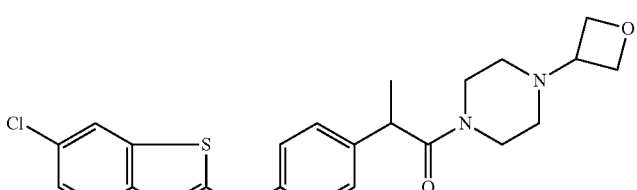 | 2-{4-[(6-chloro-1,3-benzothiazol-2-yl)oxy]phenyl}-1-[4-(oxetan-3-yl)piperazin-1-yl]propan-1-one |

TABLE 1-continued

Arylphenoxypropionate Derivatives

| | | |
|---|---|---|
| NZ-512 | | 2-{4-[(6-chloro-1,3-benzothiazol-2-yl)oxy]phenyl}-1-[4-(2,2,2-trifluoroethyl)piperazin-1-yl]propan-1-one |
| NZ-511 | | 2-{4-[(6-chloro-1,3-benzothiazol-2-yl)oxy]phenyl}-1-(4-cyclopropylpiperazin-1-yl)propan-1-one |
| NZ-510 | | 2-{4-[(6-chloro-1,3-benzothiazol-2-yl)oxy]phenyl}-1-[4-(propan-2-yl)piperazin-1-yl]propan-1-one |
| NZ-509 | | N-{4-[(6-chloro-1,3-benzothiazol-2-yl)oxy]phenyl}piperazine-1-carboxamide |
| NZ-506 | | 4-[(6-chloro-1,3-benzothiazol-2-yl)oxy]phenyl 4-methylpiperazine-1-carboxylate |
| NZ-505 | | 2-{4-[(6-chloro-1,3-benzothiazol-2-yl)oxy]phenyl}acetamide |
| NZ-500 | | 2-{4-[(6-chloro-1,3-benzothiazol-2-yl)oxy]-2-fluorophenyl}acetamide |
| NZ-496 | | 2-{4-[(5,6-difluoro-1,3-benzothiazol-2-yl)oxy]-2-fluorophenyl}acetamide |
| NZ-490 | | 2-{4-[(6-fluoro-1,3-benzothiazol-2-yl)oxy]phenyl}-1-(pyrrolidin-1-yl)ethan-1-one |

TABLE 1-continued

Arylphenoxypropionate Derivatives

| | | |
|---|---|---|
| NZ-489 | 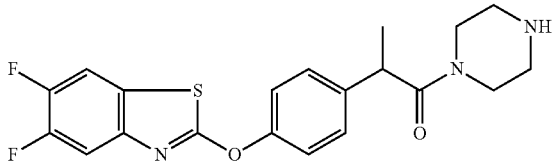 [SMILES: CC(C(=O)N1CCNCC1)c1ccc(Oc2nc3cc(F)c(F)cc3s2)cc1] | 2-{4-[(5,6-difluoro-1,3-benzothiazol-2-yl)oxy]phenyl}-1-(piperazin-1-yl)propan-1-one |
| NZ-485 | 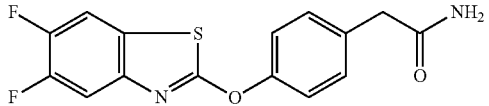 [SMILES: NC(=O)Cc1ccc(Oc2nc3cc(F)c(F)cc3s2)cc1] | 2-{4-[(5,6-difluoro-1,3-benzothiazol-2-yl)oxy]phenyl}acetamide |
| NZ-484 | 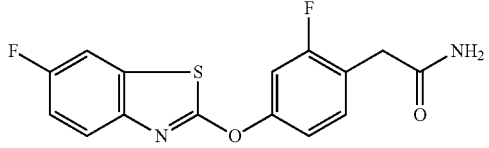 [SMILES: NC(=O)Cc1ccc(Oc2nc3ccc(F)cc3s2)cc1F] | 2-{2-fluoro-4-[(6-fluoro-1,3-benzothiazol-2-yl)oxy]phenyl}acetamide |
| NZ-481 | 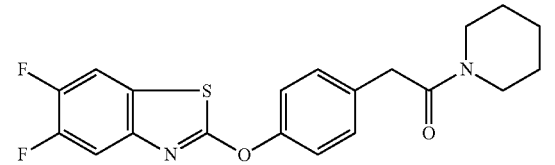 [SMILES: O=C(Cc1ccc(Oc2nc3cc(F)c(F)cc3s2)cc1)N1CCCCC1] | 2-{4-[(5,6-difluoro-1,3-benzothiazol-2-yl)oxy]phenyl}-1-(piperidin-1-yl)ethan-1-one |
| NZ-479 | 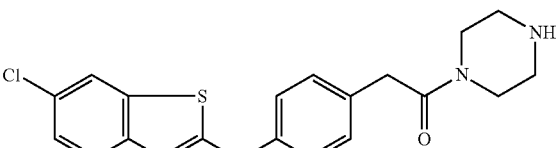 | 2-{4-[(6-chloro-1,3-benzothiazol-2-yl)oxy]phenyl}-1-(piperazin-1-yl)ethan-1-one |
| NZ-477 | 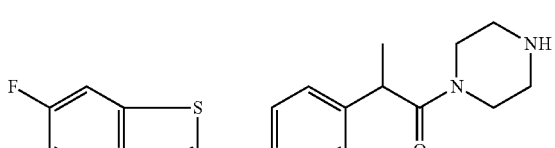 | 2-{4-[(6-fluoro-1,3-benzothiazol-2-yl)oxy]phenyl}-1-(piperazin-1-yl)propan-1-one |
| NZ-476 | 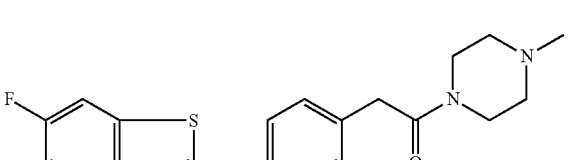 | 2-{4-[(6-fluoro-1,3-benzothiazol-2-yl)oxy]phenyl}-1-(4-methylpiperazin-1-yl)ethan-1-one |
| NZ-475 | 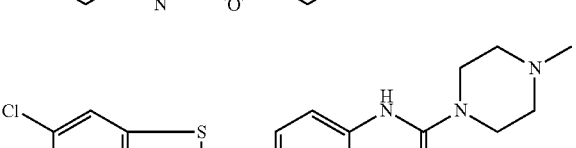 | N-{4-[(6-chloro-1,3-benzothiazol-2-yl)oxy]phenyl}-4-methylpiperazine-1-carboxamide |
| NZ-472 | 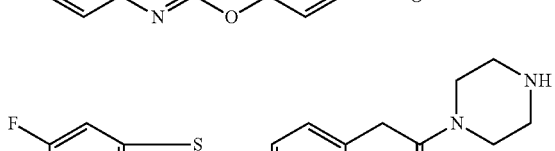 | 2-{4-[(6-fluoro-1,3-benzothiazol-2-yl)oxy]phenyl}-1-(piperazin-1-yl)ethan-1-one |

TABLE 1-continued

| Arylphenoxypropionate Derivatives | | |
|---|---|---|
| NZ-471 | | 2-{4-[(6-fluoro-1,3-benzothiazol-2-yl)oxy]phenyl}-1-(piperidin-1-yl)ethan-1-one |
| NZ-469 | | tert-butyl 4-(2-{4-[(6-fluoro-1,3-benzothiazol-2-yl)oxy]phenyl}acetyl)piperazine-1-carboxylate |
| NZ-467 | | 2-{2-fluoro-4-[(6-fluoro-1,3-benzothiazol-2-yl)oxy]phenyl}-1-(4-methylpiperazin-1-yl)ethan-1-one |
| NZ-466 | | 2-{4-[(6-fluoro-1,3-benzothiazol-2-yl)oxy]phenyl}-1-(4-methylpiperazin-1-yl)propan-1-one |
| NZ-465 | | 2-{4-[(5,6-difluoro-1,3-benzothiazol-2-yl)oxy]phenyl}-1-(4-methylpiperazin-1-yl)propan-1-one |
| NZ-464 | | 2-{4-[(6-chloro-1,3-benzothiazol-2-yl)oxy]phenyl}-1-(4-methylpiperazin-1-yl)ethan-1-one |
| NZ-460 | | 2-{4-[(6-chloroquinoxalin-2-yl)oxy]-2,6-difluorophenyl}-N-methylacetamide |
| NZ-459 | | 2-{4-[(6-chloro-1,3-benzothiazol-2-yl)oxy]-2,6-difluorophenyl}-N-methylacetamide |
| NZ-458 | | 2-{4-[(6-chloro-1,3-benzothiazol-2-yl)oxy]-2,6-difluorophenyl}acetic acid |

TABLE 1-continued

Arylphenoxypropionate Derivatives

NZ-450 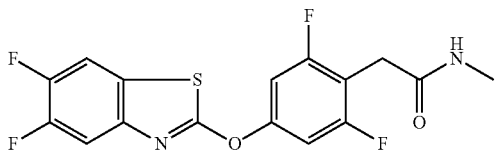 [SMILES: CNC(=O)Cc1c(F)cc(Oc2nc3cc(F)c(F)cc3s2)cc1F] 2-{4-[(5,6-difluoro-1,3-benzothiazol-2-yl)oxy]-2,6-difluorophenyl}-N-methylacetamide NZ-446 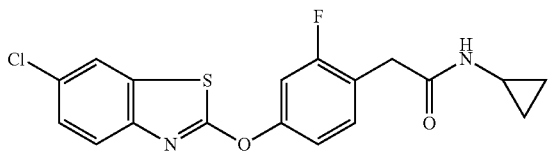 [SMILES: O=C(Cc1ccc(Oc2nc3ccc(Cl)cc3s2)cc1F)NC1CC1] N-cyclopropyl-2-{2-fluoro-4-[(6-fluoro-1,3-benzothiazol-2-yl)oxy]phenyl}acetamide NZ-440 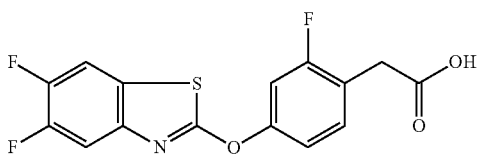 [SMILES: O=C(O)Cc1ccc(Oc2nc3cc(F)c(F)cc3s2)cc1F] 2-{4-[(5,6-difluoro-1,3-benzothiazol-2-yl)oxy]-2-fluorophenyl}acetic acid NZ-438 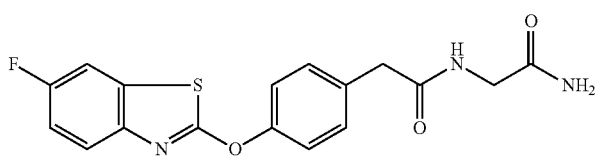 [SMILES: NC(=O)CNC(=O)Cc1ccc(Oc2nc3ccc(F)cc3s2)cc1] N-(carbamoylmethyl)-2-{4-[(6-fluoro-1,3-benzothiazol-2-yl)oxy]phenyl}acetamide NZ-433 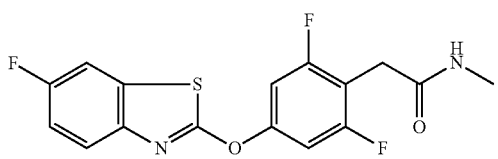 [SMILES: CNC(=O)Cc1c(F)cc(Oc2nc3ccc(F)cc3s2)cc1F] 2-{2,6-difluoro-4-[(6-fluoro-1,3-benzothiazol-2-yl)oxy]phenyl}-N-methylacetamide NZ-427 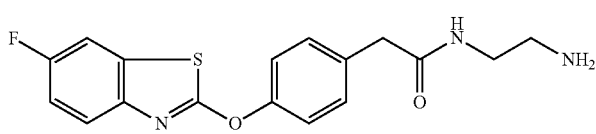 [SMILES: NCCNC(=O)Cc1ccc(Oc2nc3ccc(F)cc3s2)cc1] N-(2-aminoethyl)-2-{4-[(6-fluoro-1,3-benzothiazol-2-yl)oxy]phenyl}acetamide NZ-426 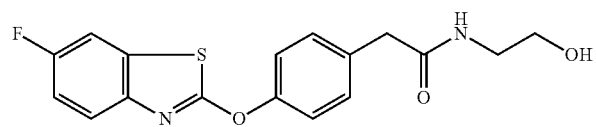 [SMILES: O=C(Cc1ccc(Oc2nc3ccc(F)cc3s2)cc1)NCCO] 2-{4-[(6-fluoro-1,3-benzothiazol-2-yl)oxy]phenyl}-N-(2-hydroxyethyl)acetamide NZ-425 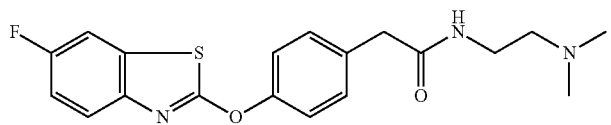 [SMILES: CN(C)CCNC(=O)Cc1ccc(Oc2nc3ccc(F)cc3s2)cc1] N-[2-(dimethylamino)ethyl]-2-{4-[(6-fluoro-1,3-benzothiazol-2-yl)oxy]phenyl}acetamide NZ-420 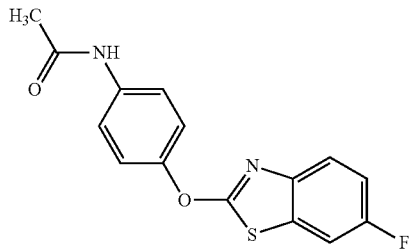 [SMILES: CC(=O)Nc1ccc(Oc2nc3ccc(F)cc3s2)cc1] N-{4-[(6-fluoro-1,3-benzothiazol-2-yl)oxy]phenyl}acetamide TABLE 1-continued Arylphenoxypropionate Derivatives

| | | |
|---|---|---|
| NZ-419 | 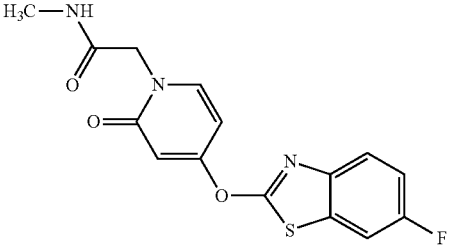 [SMILES: CNC(=O)Cn1ccc(Oc2nc3ccc(F)cc3s2)cc1=O] | 2-{4-[(6-fluoro-1,3-benzothiazol-2-yl)oxy]-2-oxo-1,2-dihydropyridin-1-yl}-N-methylacetamide |
| NZ-418 | 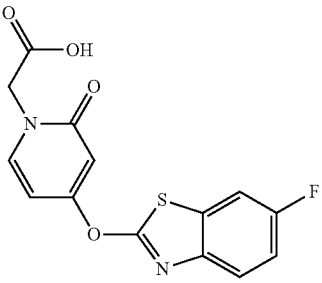 [SMILES: O=C(O)Cn1ccc(Oc2nc3ccc(F)cc3s2)cc1=O] | 2-{4-[(6-fluoro-1,3-benzothiazol-2-yl)oxy]-2-oxo-1,2-dihydropyridin-1-yl}acetic acid |
| NZ-417 | 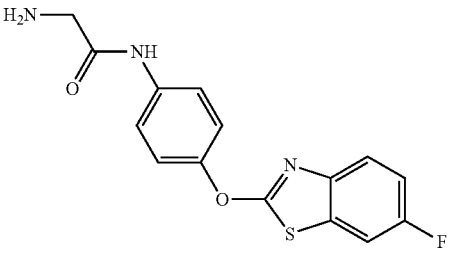 [SMILES: NCC(=O)Nc1ccc(Oc2nc3ccc(F)cc3s2)cc1] | 2-amino-N-{4-[(6-fluoro-1,3-benzothiazol-2-yl)oxy]phenyl}acetamide |
| NZ-416 | 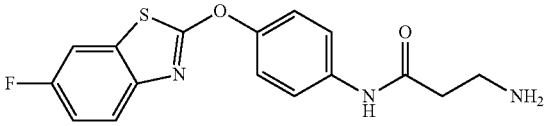 | 3-amino-N-{4-[(6-fluoro-1,3-benzothiazol-2-yl)oxy]phenyl}propanamide |
| NZ-415 | 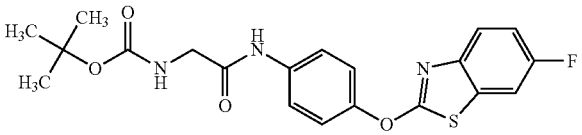 [SMILES: CC(C)(C)OC(=O)NCC(=O)Nc1ccc(Oc2nc3ccc(F)cc3s2)cc1] | tert-butyl N-[({4-[(6-fluoro-1,3-benzothiazol-2-yl)oxy]phenyl}carbamoyl)methyl]carbamate |
| NZ-414 | 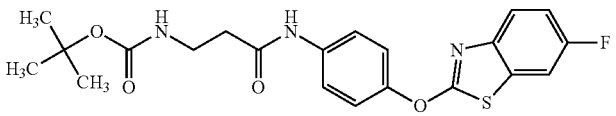 [SMILES: CC(C)(C)OC(=O)NCCC(=O)Nc1ccc(Oc2nc3ccc(F)cc3s2)cc1] | tert-butyl N-[2-({4-[(6-fluoro-1,3-benzothiazol-2-yl)oxy]phenyl}carbamoyl)ethyl]carbamate |
| NZ-413 | 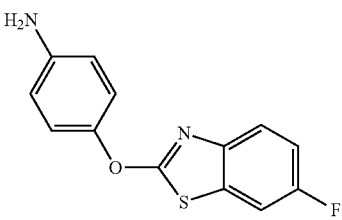 [SMILES: Nc1ccc(Oc2nc3ccc(F)cc3s2)cc1] | 4-[(6-fluoro-1,3-benzothiazol-2-yl)oxy]aniline |

TABLE 1-continued

Arylphenoxypropionate Derivatives

| NZ-412 | 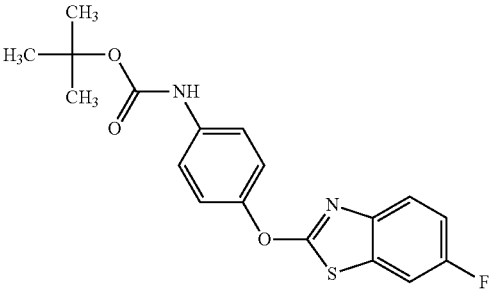 [SMILES: CC(C)(C)OC(=O)Nc1ccc(Oc2nc3ccc(F)cc3s2)cc1] | tert-butyl N-{4-[(6-fluoro-1,3-benzothiazol-2-yl)oxy]phenyl}carbamate |
| --- | --- | --- |
| NZ-411 | 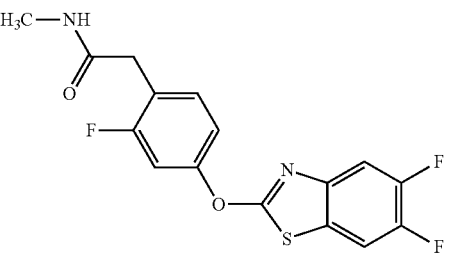 [SMILES: CNC(=O)Cc1ccc(Oc2nc3cc(F)c(F)cc3s2)cc1F] | 2-{4-[(5,6-difluoro-1,3-benzothiazol-2-yl)oxy]-2-fluorophenyl}-N-methylacetamide |
| NZ-410 | 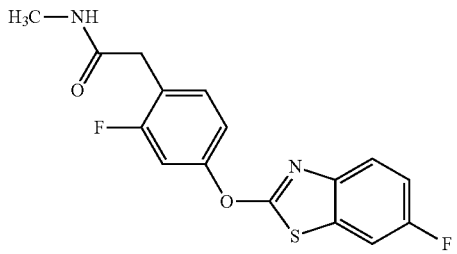 [SMILES: CNC(=O)Cc1ccc(Oc2nc3ccc(F)cc3s2)cc1F] | 2-{2-fluoro-4-[(6-fluoro-1,3-benzothiazol-2-yl)oxy]phenyl}-N-methylacetamide |
| NZ-409 | 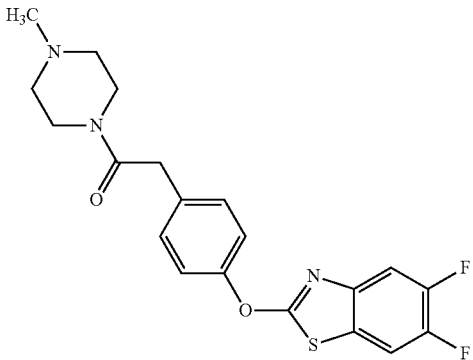 [SMILES: CN1CCN(C(=O)Cc2ccc(Oc3nc4cc(F)c(F)cc4s3)cc2)CC1] | 2-{4-[(5,6-difluoro-1,3-benzothiazol-2-yl)oxy]phenyl}-1-(4-methylpiperazin-1-yl)ethan-1-one |
| NZ-408 | 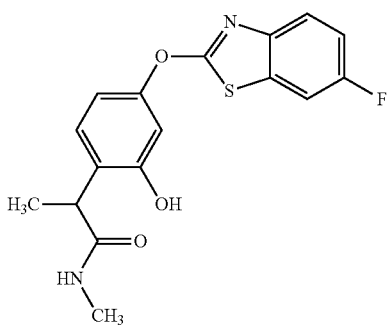 [SMILES: CNC(=O)C(C)c1ccc(Oc2nc3ccc(F)cc3s2)cc1O] | 2-{4-[(6-fluoro-1,3-benzothiazol-2-yl)oxy]-2-hydroxyphenyl}-N-methylpropanamide |

TABLE 1-continued

| Arylphenoxypropionate Derivatives | | |
|---|---|---|
| NZ-407 | | 2-{4-[(5,6-difluoro-1,3-benzothiazol-2-yl)oxy]-2-hydroxyphenyl}-N-(propan-2-yl)acetamide |
| NZ-406 | | 2-{2-[(6-fluoro-1,3-benzothiazol-2-yl)oxy]-4-hydroxyphenyl}-N-(propan-2-yl)acetamide |
| NZ-405 | | 2-{4-[(6-fluoro-1,3-benzothiazol-2-yl)oxy]-2-hydroxyphenyl}-N-(propan-2-yl)acetamide |
| NZ-404 | | 2-{4-[(6-chloro-1,3-benzothiazol-2-yl)oxy]-2-oxo-1,2-dihydropyridin-1-yl}-N-(propan-2-yl)acetamide |
| NZ-403 | | 2-{4-[(5,6-difluoro-1,3-benzothiazol-2-yl)oxy]phenyl}-N-(propan-2-yl)acetamide |
| NZ-402 | | 2-{4-[(6-chloroquinoxalin-2-yl)oxy]-2-hydroxyphenyl}-N-methylacetamide |
| NZ-401 | | 2-{4-[(5,6-difluoro-1,3-benzothiazol-2-yl)oxy]-2-hydroxyphenyl}-N-methylacetamide |

TABLE 1-continued

Arylphenoxypropionate Derivatives

| | | |
|---|---|---|
| NZ-400 | 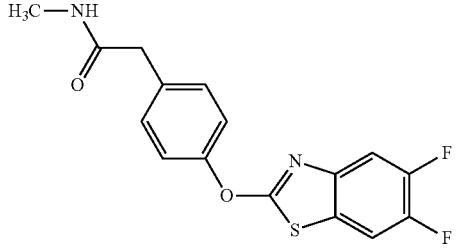 [SMILES: CNC(=O)Cc1ccc(Oc2nc3cc(F)c(F)cc3s2)cc1] | 2-{4-[(5,6-difluoro-1,3-benzothiazol-2-yl)oxy]phenyl}-N-methylacetamide |
| NZ-399 | 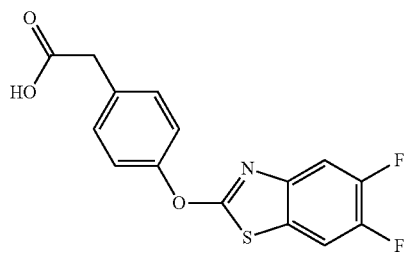 [SMILES: O=C(O)Cc1ccc(Oc2nc3cc(F)c(F)cc3s2)cc1] | 2-{4-[(5,6-difluoro-1,3-benzothiazol-2-yl)oxy]phenyl}acetic acid |
| NZ-398 | 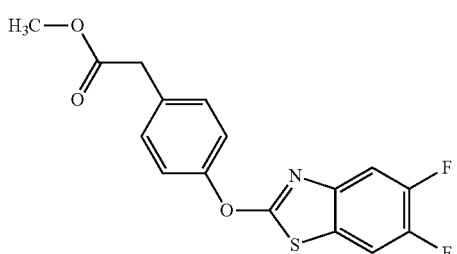 | methyl 2-{4-[(5,6-difluoro-1,3-benzothiazol-2-yl)oxy]phenyl}acetate |
| NZ-397 | 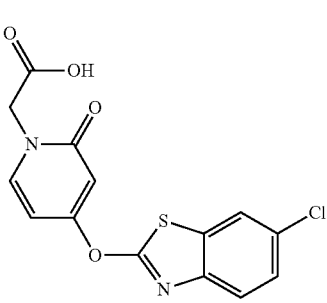 [SMILES: O=C(O)Cn1ccc(Oc2nc3ccc(Cl)cc3s2)cc1=O] | 2-{4-[(6-chloro-1,3-benzothiazol-2-yl)oxy]-2-oxo-1,2-dihydropyridin-1-yl}acetic acid |
| NZ-396 | 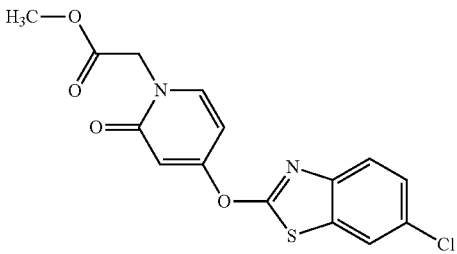 [SMILES: COC(=O)Cn1ccc(Oc2nc3ccc(Cl)cc3s2)cc1=O] | methyl 2-{4-[(6-chloro-1,3-benzothiazol-2-yl)oxy]-2-oxo-1,2-dihydropyridin-1-yl}acelate |
| NZ-395 | 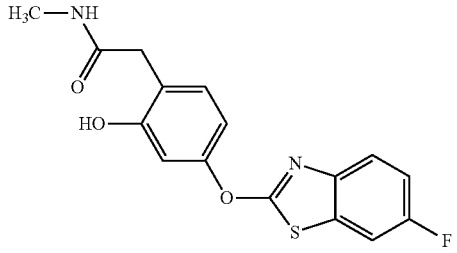 [SMILES: CNC(=O)Cc1ccc(Oc2nc3ccc(F)cc3s2)cc1O] | 2-{4-[(6-fluoro-1,3-benzothiazol-2-yl)oxy]-2-hydroxyphenyl}-N-methylacetamide |

TABLE 1-continued

| Arylphenoxypropionate Derivatives | | |
|---|---|---|
| NZ-394 | 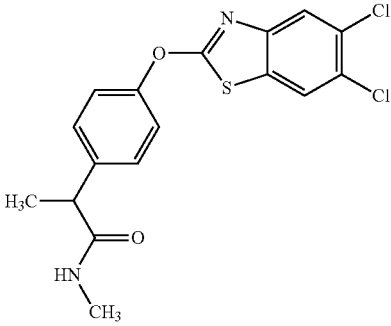 [SMILES: CNC(=O)C(C)c1ccc(Oc2nc3cc(Cl)c(Cl)cc3s2)cc1] | 2-{4-[(5,6-dichloro-1,3-benzothiazol-2-yl)oxy]phenyl}-N-methylpropanamide |
| NZ-393 | 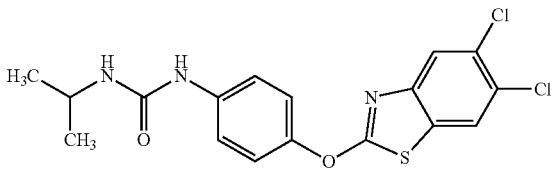 [SMILES: CC(C)NC(=O)Nc1ccc(Oc2nc3cc(Cl)c(Cl)cc3s2)cc1] | 1-{4-[(5,6-dichloro-1,3-benzothiazol-2-yl)oxy]phenyl}-3-(propan-2-yl)urea |
| NZ-392 | 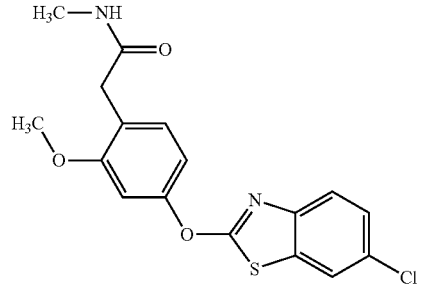 [SMILES: CNC(=O)Cc1ccc(Oc2nc3ccc(Cl)cc3s2)cc1OC] | 2-{4-[(6-chloro-1,3-benzothiazol-2-yl)oxy]-2-methoxyphenyl}-N-methylacetamide |
| NZ-391 | 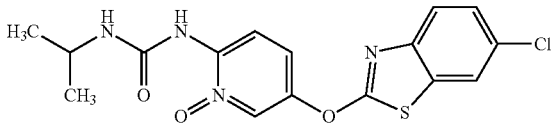 [SMILES: CC(C)NC(=O)Nc1ccc(Oc2nc3ccc(Cl)cc3s2)c[n+]1[O-]] | 1-{5-[(6-chloro-1,3-benzothiazol-2-yl)oxy]-1-oxo-1$\lambda^5$-pyridin-2-yl}-3-(propan-2-yl)urea |
| NZ-390 | 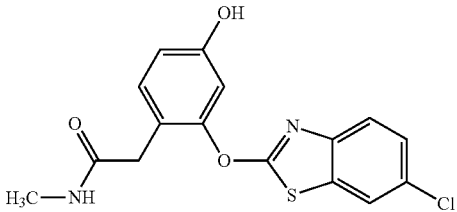 [SMILES: CNC(=O)Cc1ccc(O)cc1Oc1nc2ccc(Cl)cc2s1] | 2-{2-[(6-chloro-1,3-benzothiazol-2-yl)oxy]-4-hydroxyphenyl}-N-methylacetamide |
| NZ-389 | 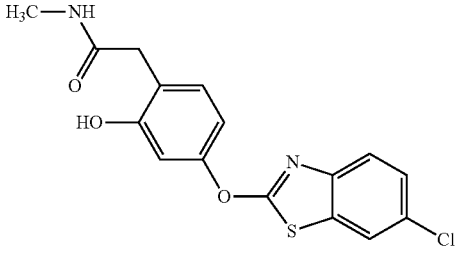 [SMILES: CNC(=O)Cc1ccc(Oc2nc3ccc(Cl)cc3s2)cc1O] | 2-{4-[(6-chloro-1,3-benzothiazol-2-yl)oxy]-2-hydroxyphenyl}-N-methylacetamide |
| NZ-388 | 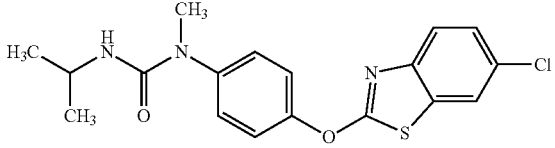 [SMILES: CC(C)NC(=O)N(C)c1ccc(Oc2nc3ccc(Cl)cc3s2)cc1] | 1-{4-[(6-chloro-1,3-benzothiazol-2-yl)oxy]phenyl}-1-methyl-3-(propan-2-yl)urea |

TABLE 1-continued

Arylphenoxypropionate Derivatives

| | | |
|---|---|---|
| NZ-387 | 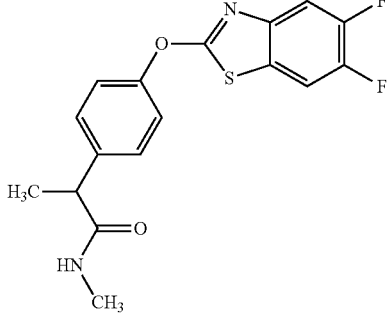 | 2-{4-[(5,6-difluoro-1,3-benzothiazol-2-yl)oxy]phenyl}-N-methylpropanamide |
| NZ-386 | 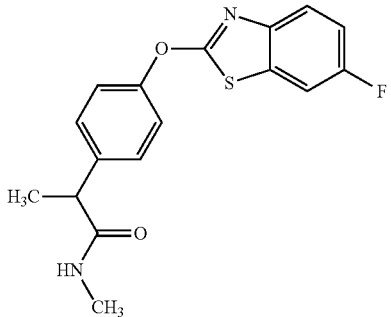 [SMILES: CNC(=O)C(C)c1ccc(Oc2nc3ccc(F)cc3s2)cc1] | 2-{4-[(6-fluoro-1,3-benzothiazol-2-yl)oxy]phenyl}-N-methylpropanamide |
| NZ-385 | 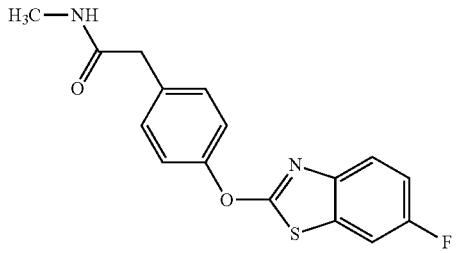 [SMILES: CNC(=O)Cc1ccc(Oc2nc3ccc(F)cc3s2)cc1] | 2-{4-[(6-fluoro-1,3-benzothiazol-2-yl)oxy]phenyl}-N-methylacetamide |
| NZ-383 | 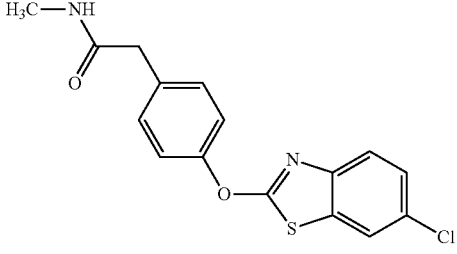 [SMILES: CNC(=O)Cc1ccc(Oc2nc3ccc(Cl)cc3s2)cc1] | 2-{4-[(6-chloro-1,3-benzothiazol-2-yl)oxy]phenyl}-N-methylacetamide |
| NZ-382 | 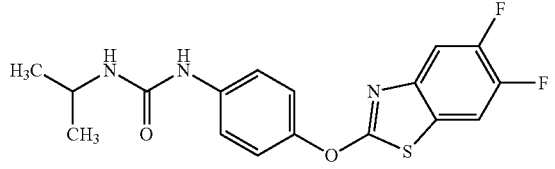 [SMILES: CC(C)NC(=O)Nc1ccc(Oc2nc3cc(F)c(F)cc3s2)cc1] | 1-{4-[(5,6-difluoro-1,3-benzothiazol-2-yl)oxy]phenyl}-3-(propan-2-yl)urea |
| NZ-381 | 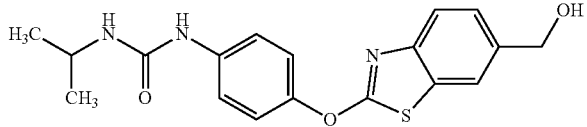 [SMILES: CC(C)NC(=O)Nc1ccc(Oc2nc3ccc(CO)cc3s2)cc1] | 1-(4-{[6-(hydroxymethyl)-1,3-benzothiazol-2-yl]oxy}phenyl)-3-(propan-2-yl)urea |

TABLE 1-continued

Arylphenoxypropionate Derivatives

| NZ-380 | 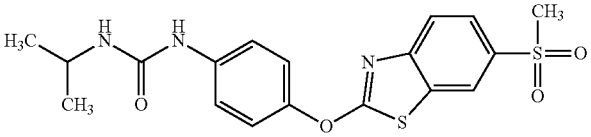 [SMILES: CC(C)NC(=O)Nc1ccc(Oc2nc3ccc(S(C)(=O)=O)cc3s2)cc1] | 1-{4-[(6-methanesulfonyl-1,3-benzothiazol-2-yl)oxy]phenyl}-3-(propan-2-yl)urea |
| --- | --- | --- |
| NZ-379 | 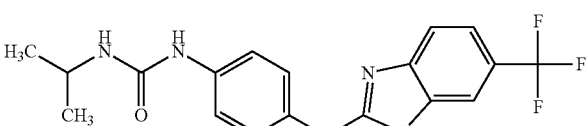 | 3-(propan-2-yl)-1-(4-{[6-(trifluoromethyl)-1,3-benzothiazol-2-yl]oxy}phenyl)urea |
| NZ-378 | 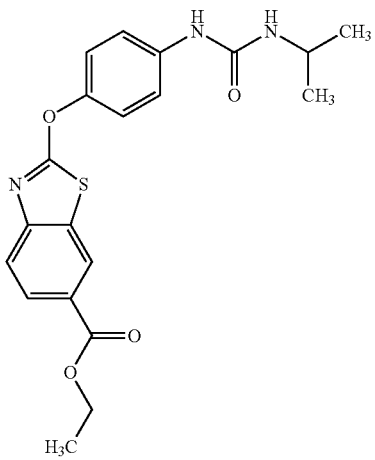 [SMILES: CCOC(=O)c1ccc2nc(Oc3ccc(NC(=O)NC(C)C)cc3)sc2c1] | ethyl 2-(4-{[(propan-2-yl)carbamoyl]amino}phenoxy)-1,3-benzothiazole-6-carboxylate |
| NZ-377 | 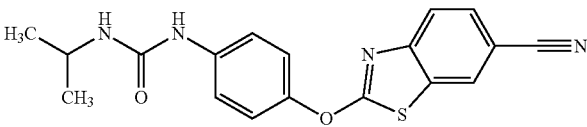 [SMILES: CC(C)NC(=O)Nc1ccc(Oc2nc3ccc(C#N)cc3s2)cc1] | 1-{4-[(6-cyano-1,3-benzothiazol-2-yl)oxy]phenyl}-3-(propan-2-yl)urea |
| NZ-376 | 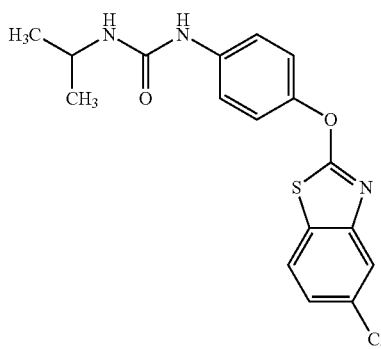 | 1-{4-[(5-chloro-1,3-benzothiazol-2-yl)oxy]phenyl}-3-(propan-2-yl)urea |
| NZ-374 | 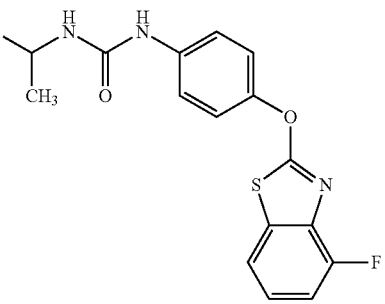 | 1-{4-[(4-fluoro-1,3-benzothiazol-2-yl)oxy]phenyl}-3-(propan-2-yl)urea |

TABLE 1-continued
Arylphenoxypropionate Derivatives
NZ-373 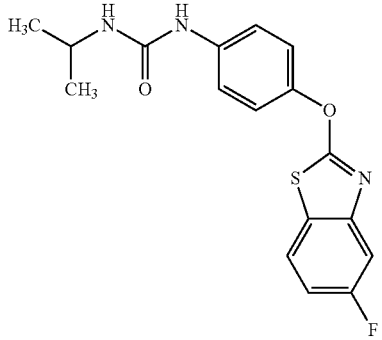 [SMILES: CC(C)NC(=O)Nc1ccc(Oc2nc3cc(F)ccc3s2)cc1] 1-{4-[(5-fluoro-1,3-benzothiazol-2-yl)oxy]phenyl}-3-(propan-2-yl)urea
NZ-372 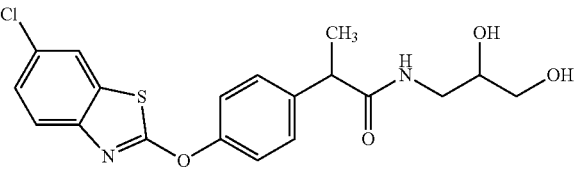 [SMILES: CC(C(=O)NCC(O)CO)c1ccc(Oc2nc3ccc(Cl)cc3s2)cc1] 2-{4-[(6-chloro-1,3-benzothiazol-2-yl)oxy]phenyl}-N-(2,3-dihydroxypropyl)propanamide
NZ-371 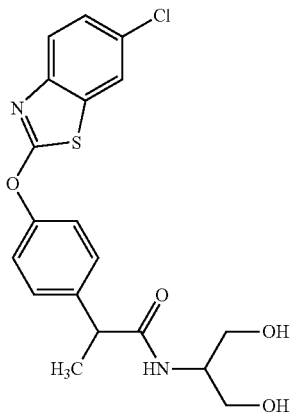 [SMILES: CC(C(=O)NC(CO)CO)c1ccc(Oc2nc3ccc(Cl)cc3s2)cc1] 2-{4-[(6-chloro-1,3-benzothiazol-2-yl)oxy]phenyl}-N-(1,3-dihydroxypropan-2-yl)propanamide
NZ-370 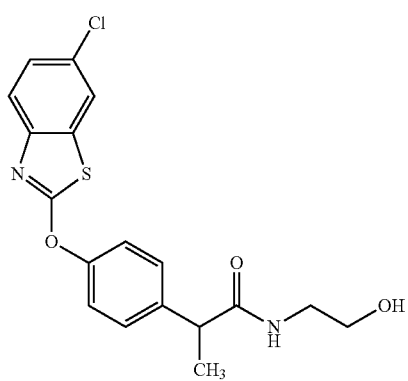 [SMILES: CC(C(=O)NCCO)c1ccc(Oc2nc3ccc(Cl)cc3s2)cc1] 2-{4-[(6-chloro-1,3-benzothiazol-2-yl)oxy]phenyl}-N-(2-hydroxyethyl)propanamide TABLE 1-continued
Arylphenoxypropionate Derivatives
NZ-369 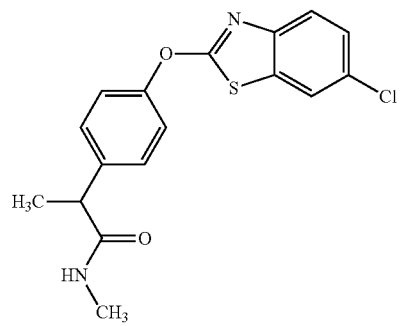 [SMILES: CNC(=O)C(C)c1ccc(Oc2nc3ccc(Cl)cc3s2)cc1] 2-{4-[(6-chloro-1,3-benzothiazol-2-yl)oxy]phenyl}-N-methylpropanamide
NZ-368 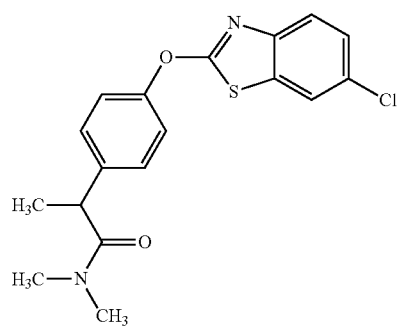 [SMILES: CC(C(=O)N(C)C)c1ccc(Oc2nc3ccc(Cl)cc3s2)cc1] 2-{4-[(6-chloro-1,3-benzothiazol-2-yl)oxy]phenyl}-N,N-dimethylpropanamide
NZ-366 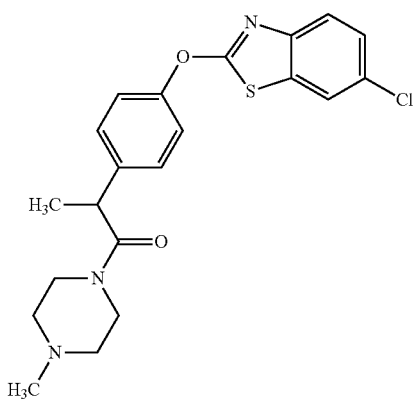 [SMILES: CC(C(=O)N1CCN(C)CC1)c1ccc(Oc2nc3ccc(Cl)cc3s2)cc1] 2-{4-[(6-chloro-1,3-benzothiazol-2-yl)oxy]phenyl}-1-(4-methylpiperazin-1-yl)propan-1-one
NZ-365 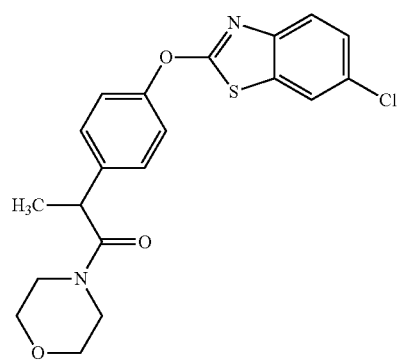 [SMILES: CC(C(=O)N1CCOCC1)c1ccc(Oc2nc3ccc(Cl)cc3s2)cc1] 2-{4-[(6-chloro-1,3-benzothiazol-2-yl)oxy]phenyl}-1-(morpholin-4-yl)propan-1-one TABLE 1-continued Arylphenoxypropionate Derivatives

| NZ-364 | | 2-{4-[(6-chloro-1,3-benzothiazol-2-yl)oxy]phenyl}-1-(piperazin-1-yl)propan-1-one |
| NZ-363 | | 1-{4-[(6-nitro-1,3-benzothiazol-2-yl)oxy]phenyl}-3-(propan-2-yl)urea |
| NZ-362 | | 1-{4-[(6-hydroxy-1,3-benzothiazol-2-yl)oxy]phenyl}-3-(propan-2-yl)urea |
| NZ-361 | | 1-{4-[(6-methoxy-1,3-benzothiazol-2-yl)oxy]phenyl}-3-(propan-2-yl)urea |
| NZ-360 | | 1-[4-(1,3-benzothiazol-2-yloxy)phenyl]-3-(propan-2-yl)urea |
| NZ-359 | | 1-{4-[(6-bromo-1,3-benzothiazol-2-yl)oxy]phenyl}-3-(propan-2-yl)urea |
| NZ-358 | | 1-{4-[(6-methyl-1,3-benzothiazol-2-yl)oxy]phenyl}-3-(propan-2-yl)urea |

TABLE 1-continued
Arylphenoxypropionate Derivatives
| NZ-357 | 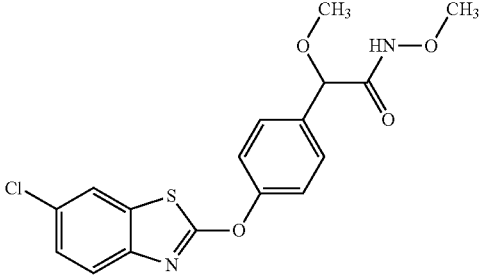 [SMILES: CONC(=O)C(OC)c1ccc(Oc2nc3ccc(Cl)cc3s2)cc1] | 2-{4-[(6-chloro-1,3-benzothiazol-2-yl)oxy]phenyl}-N,2-dimethoxyacelamide |
| NZ-356 | 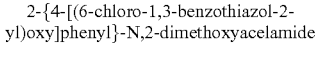 | 2-{4-[(6-chloro-1,3-benzothiazol-2-yl)oxy]phenyl}-2-methoxyacetic acid |
| NZ-355 | 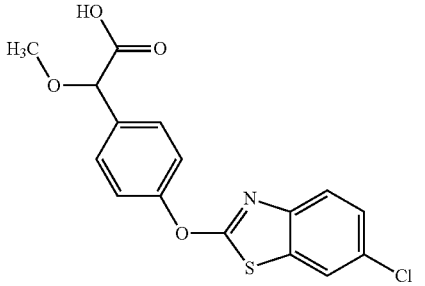 [SMILES: COC(C(=O)O)c1ccc(Oc2nc3ccc(Cl)cc3s2)cc1] | methyl 2-{4-[(6-chloro-1,3-benzothiazol-2-yl)oxy]phenyl}-2-methoxyacetate |
| NZ-354 | 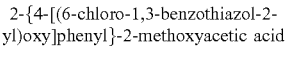 | 1-{4-[(6-chloro-1,3-benzothiazol-2-yl)oxy]phenyl}-3,3-dimethylurea |
| NZ-353 | 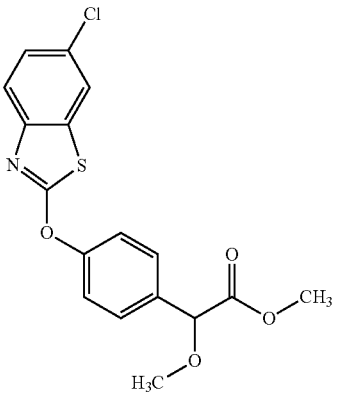 [SMILES: COC(=O)C(OC)c1ccc(Oc2nc3ccc(Cl)cc3s2)cc1] | 1-{4-[(6-chloro-1,3-benzothiazol-2-yl)oxy]phenyl}-3-methylurea |

TABLE 1-continued

Arylphenoxypropionate Derivatives

| NZ-352 | (structure) | 4-[(6-chloro-1,3-benzothiazol-2-yl)oxy]aniline |
| NZ-351 | (structure) | tert-butyl N-{4-[(6-chloro-1,3-benzothiazol-2-yl)oxy]phenyl}carbamate |
| NZ-350 | (structure) | 1-({4-[(6-chloro-1,3-benzothiazol-2-yl)oxy]phenyl}methyl)-3-methylurea |
| NZ-349 | (structure) | 1-({4-[(6-chloro-1,3-benzothiazol-2-yl)oxy]phenyl}methyl)-3,3-dimethylurea |
| NZ-348 | (structure) | {4-[(6-chloro-1,3-benzothiazol-2-yl)oxy]phenyl}methanamine |
| NZ-347 | (structure) | tert-butyl N-({4-[(6-chloro-1,3-benzothiazol-2-yl)oxy]phenyl}methyl)carbamate |
| NZ-346 | (structure) | 1-{4-[(6-chloroquinolin-2-yl)oxy]phenyl}-3-(propan-2-yl)urea |

TABLE 1-continued

Arylphenoxypropionate Derivatives

| | | |
|---|---|---|
| NZ-345 | | 1-{4-[(6-fluoroquinoxalin-2-yl)oxy]phenyl}-3-(propan-2-yl)urea |
| NZ-344 | | 1-{4-[(6-chloroquinoxalin-2-yl)oxy]phenyl}-3-methoxyurea |
| NZ-343 | | 1-{4-[(6-chloroquinoxalin-2-yl)oxy]phenyl}-3,3-dimethylurea |
| NZ-342 | | 1-{4-[(6-chloroquinoxalin-2-yl)oxy]phenyl}-3-methylurea |
| NZ-341 | | 1-{4-[(6-chloro-1,3-benzothiazol-2-yl)oxy]phenyl}imidazolidin-2-one |
| NZ-338 | | 2-{4-[(6-chloro-1,3-benzothiazol-2-yl)oxy]phenyl}-2-hydroxy-N-methoxyacetamide |

TABLE 1-continued

Arylphenoxypropionate Derivatives

| | | |
|---|---|---|
| NZ-337 | 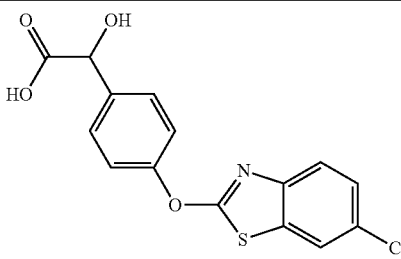 | 2-{4-[(6-chloro-1,3-benzothiazol-2-yl)oxy]phenyl}-2-hydroxyacetic acid |
| NZ-336 | 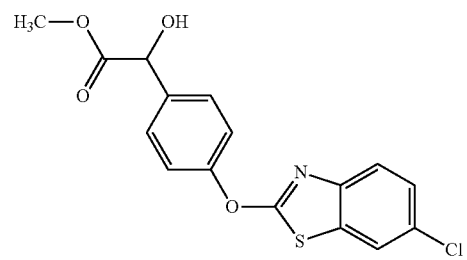 [SMILES: COC(=O)C(O)c1ccc(Oc2nc3ccc(Cl)cc3s2)cc1] | methyl 2-{4-[(6-chloro-1,3-benzothiazol-2-yl)oxy]phenyl}-2-hydroxyacetate |
| NZ-335 | 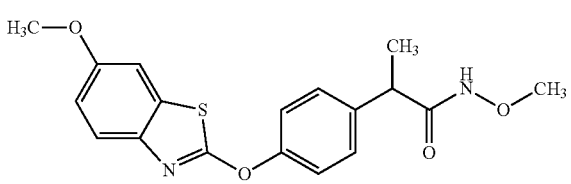 | N-methoxy-2-{4-[(6-methoxy-1,3-benzothiazol-2-yl)oxy]phenyl}propanamide |
| NZ-334 | 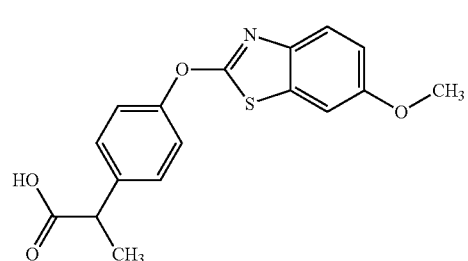 [SMILES: COc1ccc2nc(Oc3ccc(C(C)C(=O)O)cc3)sc2c1] | 2-{4-[(6-methoxy-1,3-benzothiazol-2-yl)oxy]phenyl}propanoic acid |
| NZ-333 | 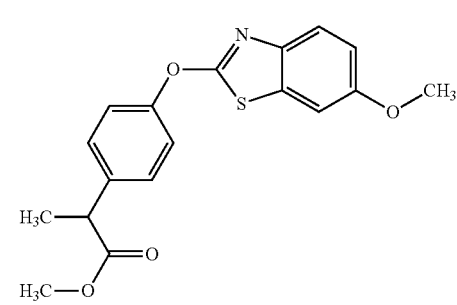 [SMILES: COC(=O)C(C)c1ccc(Oc2nc3ccc(OC)cc3s2)cc1] | methyl 2-{4-[(6-methoxy-1,3-benzothiazol-2-yl)oxy]phenyl}propanoate |
| NZ-332 | 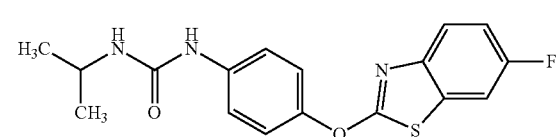 | 1-{4-[(6-fluoro-1,3-benzothiazol-2-yl)oxy]phenyl}-3-(propan-2-yl)urea |
| NZ-331 | 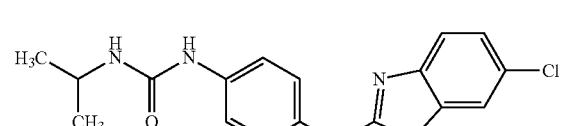 | 1-{4-[(6-chloro-1,3-benzothiazol-2-yl)oxy]phenyl}-3-(propan-2-yl)urea |

TABLE 1-continued

| | Arylphenoxypropionate Derivatives | |
|---|---|---|
| NZ-330 | | 2-{4-[(6-fluoro-1,3-benzothiazol-2-yl)oxy]phenyl}-N-methoxypropanamide |
| NZ-329 | | 2-{4-[(6-fluoro-1,3-benzothiazol-2-yl)oxy]phenyl}propanoic acid |
| NZ-328 | | methyl 2-{4-[(6-fluoro-1,3-benzothiazol-2-yl)oxy]phenyl}propanoate |
| NZ-327 | | 2-{4-[(6-chloro-1,3-benzothiazol-2-yl)oxy]phenyl}-N-(propan-2-yl)propanamide |
| NZ-326 | | 2-{4-[(6-chloroquinoxalin-2-yl)oxy]phenoxy}-N-(propan-2-yloxy)acetamide |
| NZ-325 | | (Z)-2-{4-[(6-chloroquinoxalin-2-yl)oxy]phenoxy}-N-methoxyethenecarbonimidoyl chloride |

TABLE 1-continued

Arylphenoxypropionate Derivatives

| NZ-323 | 2-{4-[(6-chloroquinoxalin-2-yl)oxy]phenoxy}-N-(cyclopropylmethoxy)acetamide |
| NZ-322 | 1-{4-[(6-chloroquinoxalin-2-yl)oxy]phenyl}-3-(propan-2-yl)urea |
| NZ-321 | tert-butyl N-{4-[(6-chloroquinoxalin-2-yl)oxy]phenyl}carbamate |
| NZ-320 | N-methoxy-2-oxo-7-phenoxy-2H-chromene-3-carboxamide |
| NZ-319 | 2-{4-[(6-chloro-1,3-benzothiazol-2-yl)oxy]phenoxy}-N-methoxy-2-methylpropanamide |
| NZ-318 | 2-{4-[(6-chloro-1,3-benzothiazol-2-yl)oxy]phenoxy}-2-methylpropanoic acid |

TABLE 1-continued

Arylphenoxypropionate Derivatives

| | | |
|---|---|---|
| NZ-317 | 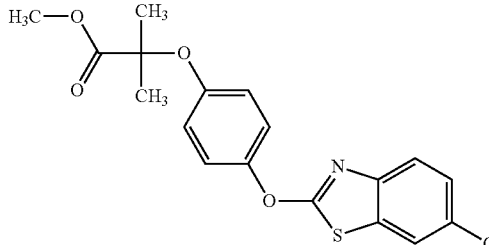 | methyl 2-{4-[(6-chloro-1,3-benzothiazol-2-yl)oxy]phenoxy}-2-methylpropanoate |
| NZ-316 | 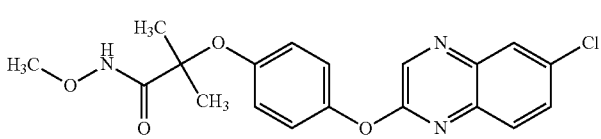 [SMILES: CONC(=O)C(C)(C)Oc1ccc(Oc2cnc3cc(Cl)ccc3n2)cc1] | 2-{4-[(6-chloroquinoxalin-2-yl)oxy]phenoxy}-N-methoxy-2-methylpropanamide |
| NZ-315 | 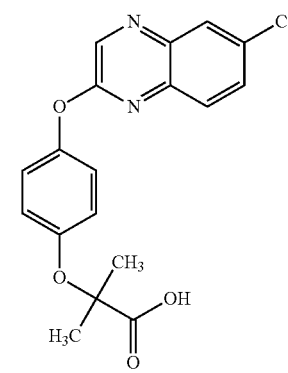 | 2-{4-[(6-chloroquinoxalin-2-yl)oxy]phenoxy}-2-methylpropanoic acid |
| NZ-314 | 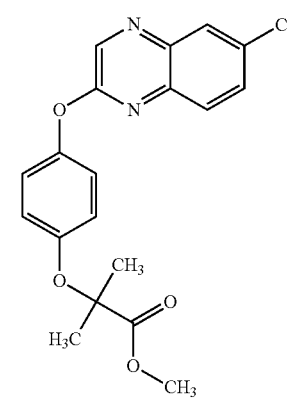 | methyl 2-{4-[(6-chloroquinoxalin-2-yl)oxy]phenoxy}-2-methylpropanoate |
| NZ-313 | 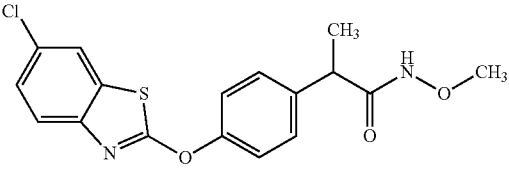 [SMILES: CONC(=O)C(C)c1ccc(Oc2nc3ccc(Cl)cc3s2)cc1] | 2-{4-[(6-chloro-1,3-benzothiazol-2-yl)oxy]phenyl}-N-methoxypropanamide |
| NZ-312 | 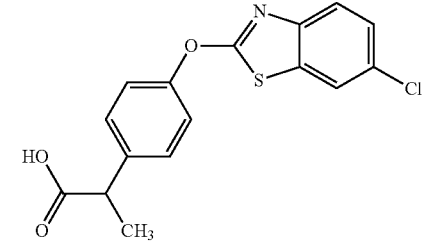 [SMILES: CC(C(=O)O)c1ccc(Oc2nc3ccc(Cl)cc3s2)cc1] | 2-{4-[(6-chloro-1,3-benzothiazol-2-yl)oxy]phenyl}propanoic acid |

TABLE 1-continued

Arylphenoxypropionate Derivatives

| NZ-311 | methyl 2-{4-[(6-chloro-1,3-benzothiazol-2-yl)oxy]phenyl}propanoate |
| NZ-310 | 2-{4-[(6-chloroquinoxalin-2-yl)oxy]phenyl}-N-methoxypropanamide |
| NZ-309 | 2-{4-[(6-chloroquinoxalin-2-yl)oxy]phenyl}propanoic acid |
| NZ-308 | methyl 2-{4-[(6-chloroquinoxalin-2-yl)oxy]phenyl}propanoate |
| NZ-307 | 2-{4-[(6-chloroquinoxalin-2-yl)oxy]phenoxy}-N-(propan-2-yl)acetamide |
| NZ-306 | 2-{4-[(6-chloroquinoxalin-2-yl)oxy]phenoxy}-N-ethylacetamide |

TABLE 1-continued

| | Arylphenoxypropionate Derivatives | |
|---|---|---|
| NZ-305 | | 2-{4-[(6-fluoro-1,3-benzothiazol-2-yl)oxy]phenoxy}-N-methoxyacetamide |
| NZ-304 | | 2-{4-[(6-fluoro-1,3-benzothiazol-2-yl)oxy]phenoxy}acetic acid |
| NZ-303 | | methyl 2-{4-[(6-fluoro-1,3-benzothiazol-2-yl)oxy]phenoxy}acetate |
| NZ-302 | | methyl 2-{4-[(6-chloro-1,3-benzoxazol-2-yl)oxy]phenyl}acetate |
| NZ-301 | | 2-{4-[(6-chloroquinoxalin-2-yl)oxy]phenyl}-N-methoxyacetamide |
| NZ-300 | | 2-{4-[(6-fluoro-1,3-benzothiazol-2-yl)oxy]phenyl}-N-methoxyacetamide |
| NZ-299 | | 2-{4-[(6-fluoro-1,3-benzothiazol-2-yl)oxy]phenyl}acetic acid |

TABLE 1-continued

Arylphenoxypropionate Derivatives

| | | |
|---|---|---|
| NZ-298 | 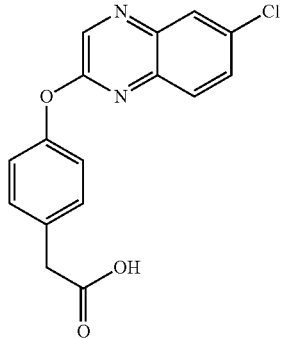 [SMILES: O=C(O)Cc1ccc(Oc2cnc3cc(Cl)ccc3n2)cc1] | 2-{4-[(6-chloroquinoxalin-2-yl)oxy]phenyl}acetic acid |
| NZ-297 | 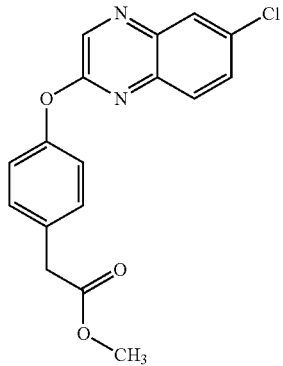 [SMILES: COC(=O)Cc1ccc(Oc2cnc3cc(Cl)ccc3n2)cc1] | methyl 2-{4-[(6-chloroquinoxalin-2-yl)oxy]phenyl}acetate |
| NZ-296 | 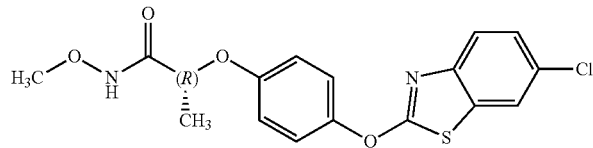 | (2R)-2-{4-[(6-chloro-1,3-benzoxazol-2-yl)oxy]phenoxy}-N-methoxypropanamide |
| NZ-295 | 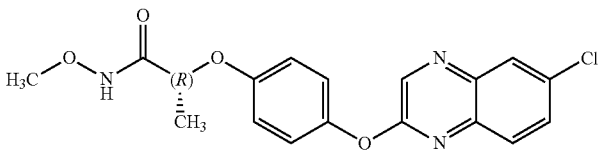 | (2R)-2-{4-[(6-chloroquinoxalin-2-yl)oxy]phenoxy}-N-methoxypropanamide |
| NZ-294 | 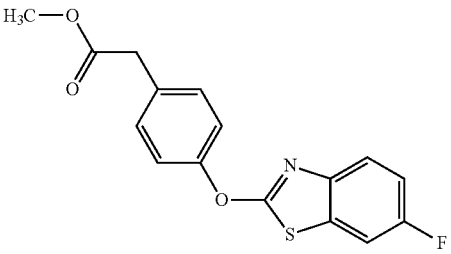 [SMILES: COC(=O)Cc1ccc(Oc2nc3ccc(F)cc3s2)cc1] | methyl 2-{4-[(6-fluoro-1,3-benzothiazol-2-yl)oxy]phenyl}acetate |
| NZ-293 | 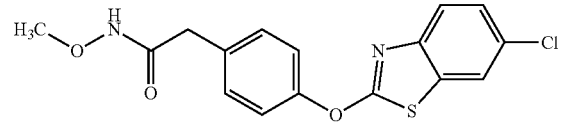 [SMILES: CONC(=O)Cc1ccc(Oc2nc3ccc(Cl)cc3s2)cc1] | 2-{4-[(6-chloro-1,3-benzothiazol-2-yl)oxy]phenyl}-N-methoxyacetamide |

TABLE 1-continued

Arylphenoxypropionate Derivatives

NZ-292 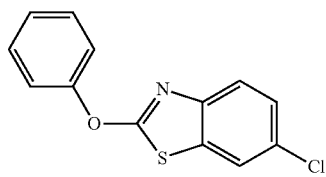 [SMILES: Clc1ccc2nc(Oc3ccccc3)sc2c1] 6-chloro-2-phenoxy-1,3-benzothiazole

NZ-291 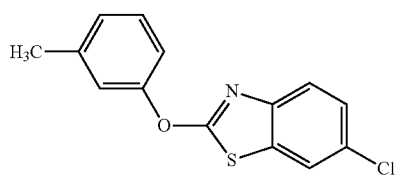 [SMILES: Cc1cccc(Oc2nc3ccc(Cl)cc3s2)c1] 6-chloro-2-(3-methylphenoxy)-1,3-benzothiazole

NZ-290 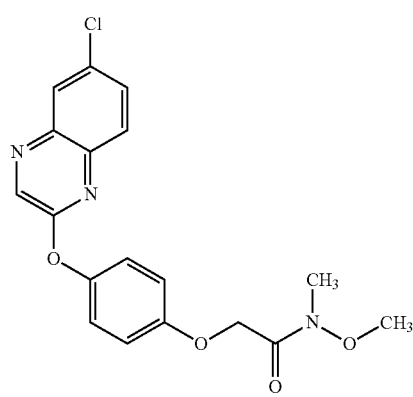 [SMILES: CON(C)C(=O)COc1ccc(Oc2cnc3cc(Cl)ccc3n2)cc1] 2-{4-[(6-chloroquinoxalin-2-yl)oxy]phenoxy}-N-methoxy-N-methylacetamide NZ-289 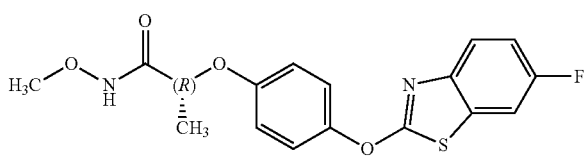 (2R)-2-{4-[(6-fluoro-1,3-benzothiazol-2-yl)oxy]phenoxy}-N-methoxypropanamide NZ-288 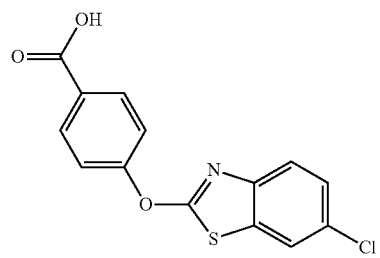 [SMILES: O=C(O)c1ccc(Oc2nc3ccc(Cl)cc3s2)cc1] 4-[(6-chloro-1,3-benzothiazol-2-yl)oxy]benzoic acid NZ-287 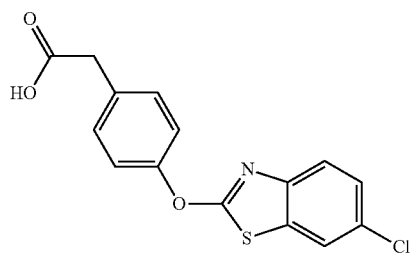 [SMILES: O=C(O)Cc1ccc(Oc2nc3ccc(Cl)cc3s2)cc1] 2-{4-[(6-chloro-1,3-benzothiazol-2-yl)oxy]phenyl}acetic acid NZ-286 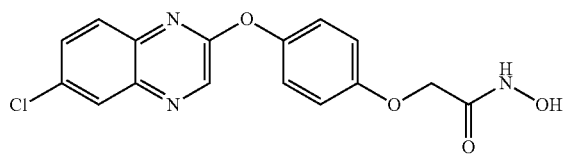 [SMILES: O=C(COc1ccc(Oc2cnc3cc(Cl)ccc3n2)cc1)NO] 2-{4-[(6-chloroquinoxalin-2-yl)oxy]phenoxy}-N-hydroxyacetamide TABLE 1-continued Arylphenoxypropionate Derivatives NZ-285 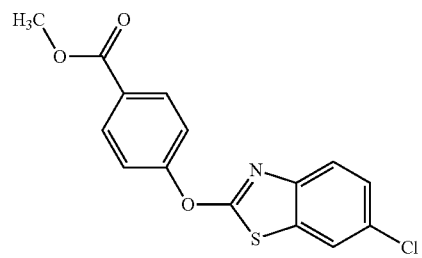 [SMILES: COC(=O)c1ccc(Oc2nc3ccc(Cl)cc3s2)cc1] methyl 4-[(6-chloro-1,3-benzothiazol-2-yl)oxy]benzoate NZ-284 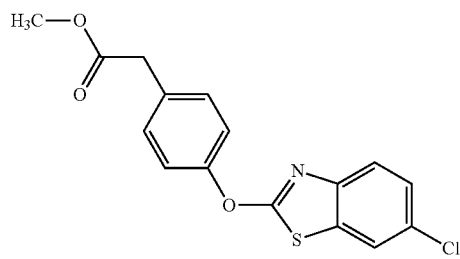 [SMILES: COC(=O)Cc1ccc(Oc2nc3ccc(Cl)cc3s2)cc1] methyl 2-{4-[(6-chloro-1,3-benzothiazol-2-yl)oxy]phenyl}acetate NZ-283 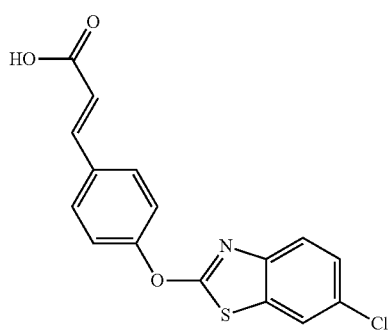 [SMILES: O=C(O)/C=C/c1ccc(Oc2nc3ccc(Cl)cc3s2)cc1] (2E)-3-{4-[(6-chloro-1,3-benzothiazol-2-yl)oxy]phenyl}prop-2-enoic acid NZ-282 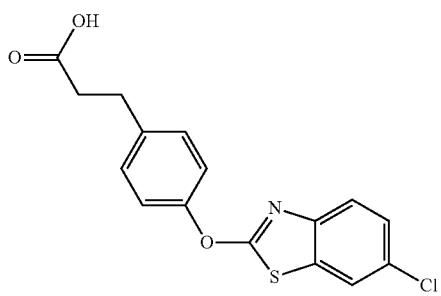 [SMILES: O=C(O)CCc1ccc(Oc2nc3ccc(Cl)cc3s2)cc1] 3-{4-[(6-chloro-1,3-benzothiazol-2-yl)oxy]phenyl}propanoic acid NZ-281 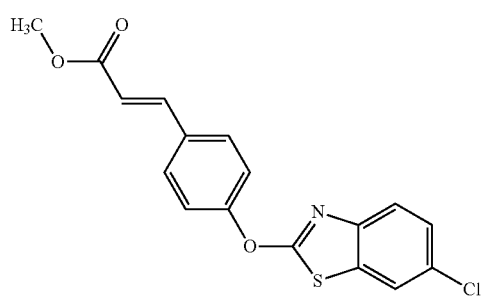 [SMILES: COC(=O)/C=C/c1ccc(Oc2nc3ccc(Cl)cc3s2)cc1] methyl (2E)-3-{4-[(6-chloro-1,3-benzothiazol-2-yl)oxy]phenyl}prop-2-enoate NZ-280 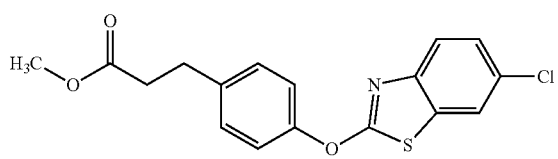 [SMILES: COC(=O)CCc1ccc(Oc2nc3ccc(Cl)cc3s2)cc1] methyl 3-{4-[(6-chloro-1,3-benzothiazol-2-yl)oxy]phenyl}propanoate TABLE 1-continued Arylphenoxypropionate Derivatives NZ-279 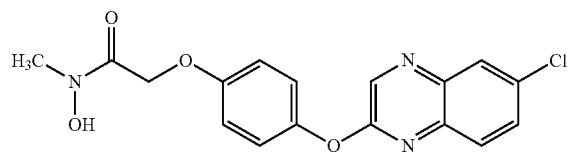 [SMILES: CN(O)C(=O)COc1ccc(Oc2cnc3cc(Cl)ccc3n2)cc1] 2-{4-[(6-chloroquinoxalin-2-yl)oxy]phenoxy}-N-hydroxy-N-methylacetamide NZ-278 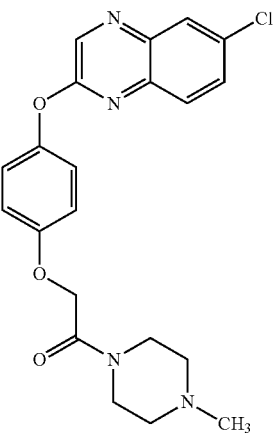 [SMILES: CN1CCN(C(=O)COc2ccc(Oc3cnc4cc(Cl)ccc4n3)cc2)CC1] 2-{4-[(6-chloroquinoxalin-2-yl)oxy]phenoxy}-1-(4-methylpiperazin-1-yl)ethan-1-one NZ-277 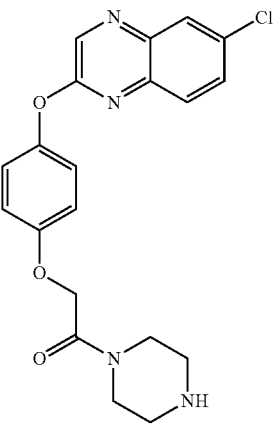 [SMILES: O=C(COc1ccc(Oc2cnc3cc(Cl)ccc3n2)cc1)N1CCNCC1] 2-{4-[(6-chloroquinoxalin-2-yl)oxy]phenoxy}-1-(piperazin-1-yl)ethan-1-one NZ-276 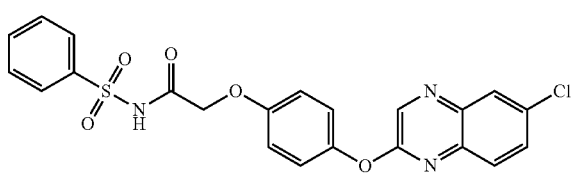 [SMILES: O=C(COc1ccc(Oc2cnc3cc(Cl)ccc3n2)cc1)NS(=O)(=O)c1ccccc1] N-(benzenesulfonyl)-2-{4-[(6-chloroquinoxalin-2-yl)oxy]phenoxy}acetamide NZ-275 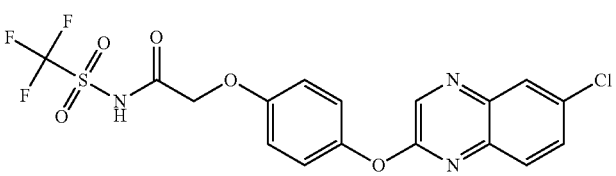 [SMILES: O=C(COc1ccc(Oc2cnc3cc(Cl)ccc3n2)cc1)NS(=O)(=O)C(F)(F)F] 2-{4-[(6-chloroquinoxalin-2-yl)oxy]phenoxy}-N-trifluoromethanesulfonylacetamide NZ-274 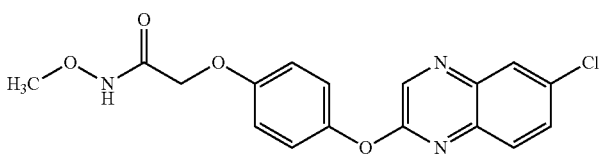 [SMILES: CONC(=O)COc1ccc(Oc2cnc3cc(Cl)ccc3n2)cc1] 2-{4-[(6-chloroquinoxalin-2-yl)oxy]phenoxy}-N-methoxyacetamide TABLE 1-continued
Arylphenoxypropionate Derivatives
NZ-273 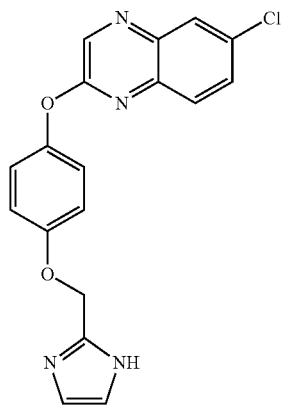 [SMILES: Clc1ccc2nc(Oc3ccc(OCc4ncc[nH]4)cc3)cnc2c1] 6-chloro-2-[4-(1H-imidazol-2-ylmethoxy)phenoxy]quinoxaline
NZ-272 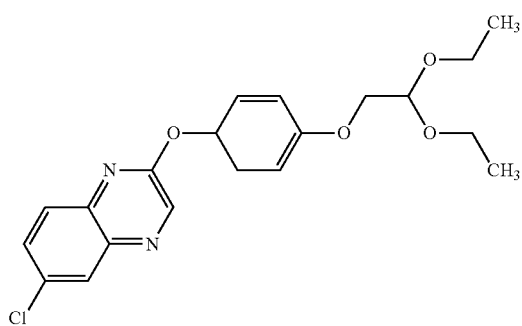 [SMILES: CCOC(COC1=CCC(Oc2cnc3cc(Cl)ccc3n2)C=C1)OCC] 6-chloro-2-[4-(2,2-diethoxyethoxy)phenoxy]quinoxaline
NZ-271 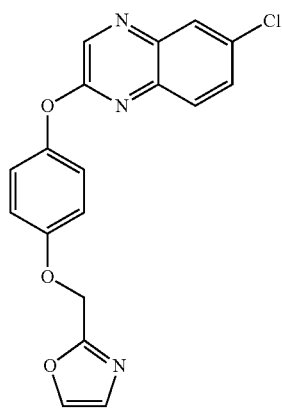 [SMILES: Clc1ccc2nc(Oc3ccc(OCc4ncco4)cc3)cnc2c1] 6-chloro-2-[4-(1,3-oxazol-2-ylmethoxy)phenoxy]quinoxaline
NZ-270 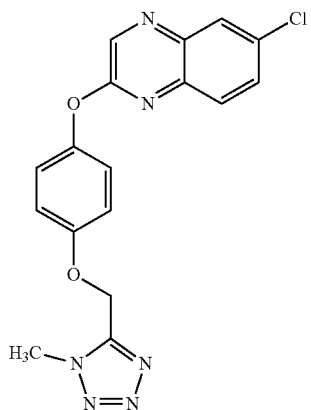 [SMILES: Cn1nnnc1COc1ccc(Oc2cnc3cc(Cl)ccc3n2)cc1] 6-chloro-2-{4-[(1-methyl-1H-1,2,3,4-tetrazol-5-yl)methoxy]phenoxy}quinoxaline TABLE 1-continued Arylphenoxypropionate Derivatives

| NZ-269 | 6-chloro-2-{4-[(2-methyl-2H-1,2,3,4-tetrazol-5-yl)methoxy]phenoxy}quinoxaline |
| NZ-268 | 6-chloro-2-[4-(1H-1,2,3,4-tetrazol-5-ylmethoxy)phenoxy]quinoxaline |
| NZ-267 | 2-{4-[(6-chloroquinoxalin-2-yl)oxy]phenoxy}-N-methylacetamide |
| NZ-266 | 2-{4-[(6-chloroquinoxalin-2-yl)oxy]phenoxy}-1-(morpholin-4-yl)ethan-1-one |

TABLE 1-continued
Arylphenoxypropionate Derivatives
NZ-265 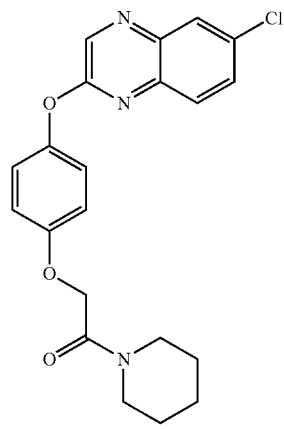 [SMILES: O=C(COc1ccc(Oc2cnc3cc(Cl)ccc3n2)cc1)N1CCCCC1] 2-{4-[(6-chloroquinoxalin-2-yl)oxy]phenoxy}-1-(piperidin-1-yl)ethan-1-one
NZ-264 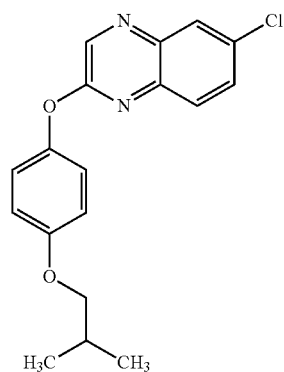 [SMILES: CC(C)COc1ccc(Oc2cnc3cc(Cl)ccc3n2)cc1] 1-{4-[(6-chloroquinoxalin-2-yl)oxy]phenoxy}propan-2-ol
NZ-263 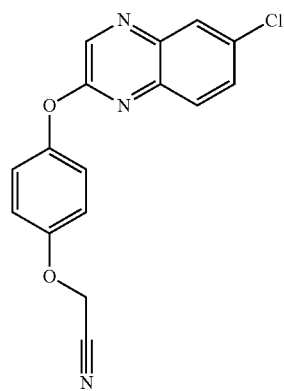 [SMILES: N#CCOc1ccc(Oc2cnc3cc(Cl)ccc3n2)cc1] 2-{4-[(6-chloroquinoxalin-2-yl)oxy]phenoxy}acetonitrile
NZ-262 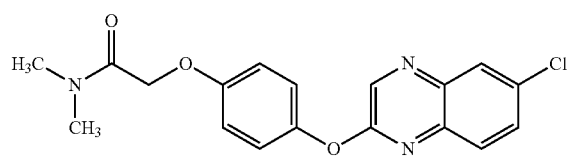 [SMILES: CN(C)C(=O)COc1ccc(Oc2cnc3cc(Cl)ccc3n2)cc1] 2-{4-[(6-chloroquinoxalin-2-yl)oxy]phenoxy}-N,N-dimethylacetamide TABLE 1-continued Arylphenoxypropionate Derivatives

| | | |
|---|---|---|
| NZ-261 | 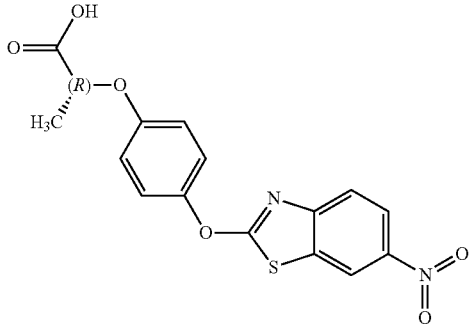 | (2R)-2-{4-[(6-nitro-1,3-benzothiazol-2-yl)oxy]phenoxy}propanoic acid |
| NZ-260 | 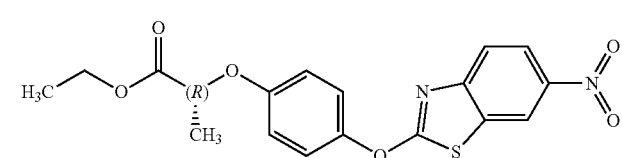 | ethyl (2R)-2-{4-[(6-nitro-1,3-benzothiazol-2-yl)oxy]phenoxy}propanoate |
| NZ-259 | 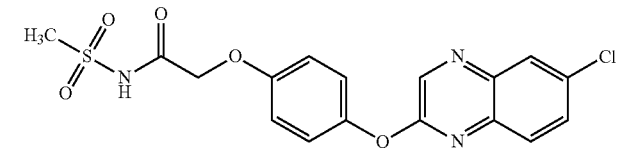 [SMILES: CS(=O)(=O)NC(=O)COc1ccc(Oc2cnc3cc(Cl)ccc3n2)cc1] | 2-{4-[(6-chloroquinoxalin-2-yl)oxy]phenoxy}-N-methanesulfonylacetamide |
| NZ-258 | 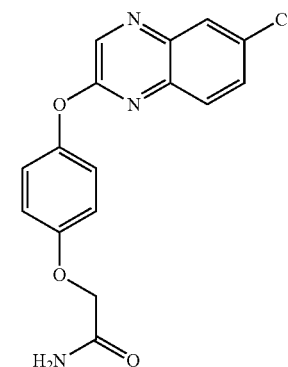 | 2-{4-[(6-chloroquinoxalin-2-yl)oxy]phenoxy}acetamide |
| NZ-257 | 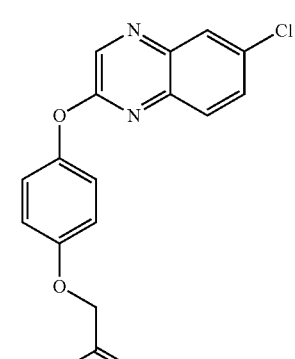 | 2-{4-[(6-chloroquinoxalin-2-yl)oxy]phenoxy}acetic acid |
| NZ-256 | 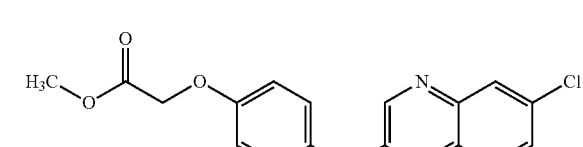 | methyl 2-{4-[(6-chloroquinoxalin-2-yl)oxy]phenoxy}acetate |

/ TABLE 1-continued

Arylphenoxypropionate Derivatives

| NZ-255 | 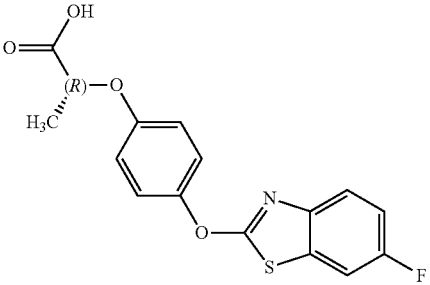 | (2R)-2-{4-[(6-fluoro-1,3-benzothiazol-2-yl)oxy]phenoxy}propanoic acid |
| NZ-254 | 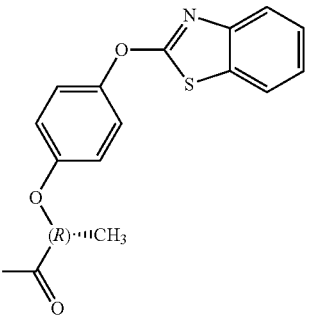 | (2R)-2-[4-(1,3-benzothiazol-2-yloxy)phenoxy]propanoic acid |
| NZ-253 | 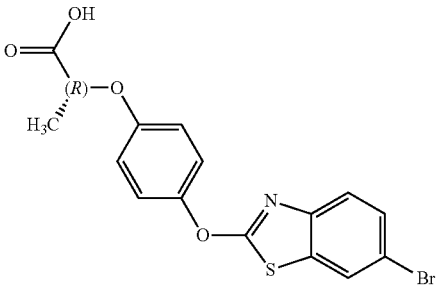 | (2R)-2-{4-[(6-bromo-1,3-benzothiazol-2-yl)oxy]phenoxy}propanoic acid |
| NZ-252 | 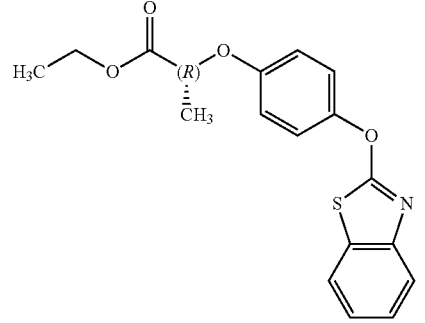 | ethyl (2R)-2-[4-(1,3-benzothiazol-2-yloxy)phenoxy]propanoate |
| NZ-251 | 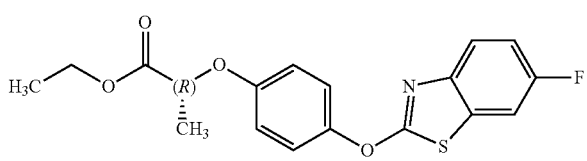 | ethyl (2R)-2-{4-[(6-fluoro-1,3-benzothiazol-2-yl)oxy]phenoxy}propanoate |
| NZ-250 | 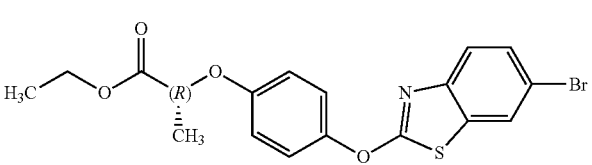 | ethyl (2R)-2-{4-[(6-bromo-1,3-benzothiazol-2-yl)oxy]phenoxy}propanoate |

TABLE 1-continued

Arylphenoxypropionate Derivatives

| | | |
|---|---|---|
| NZ-247 | 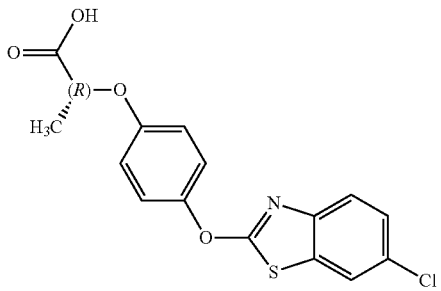 | (2R)-2-{4-[(6-chloro-1,3-benzothiazol-2-yl)oxy]phenoxy}propanoic acid |
| NZ-246 | 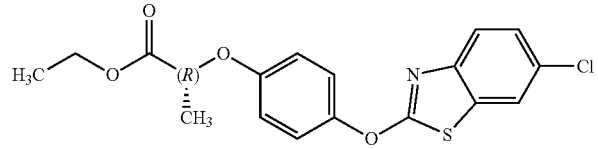 | ethyl (2R)-2-{4-[(6-chloro-1,3-benzothiazol-2-yl)oxy]phenoxy}propanoate |
| fenoxaprop-p-ethyl | 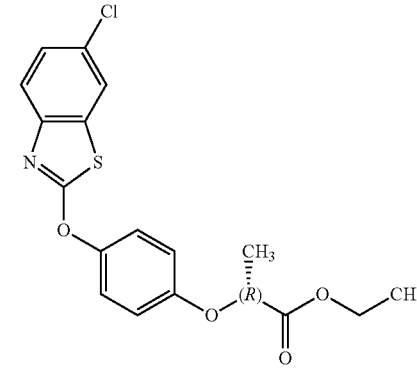 | ethyl (2R)-2-{4-[(6-chloro-1,3-benzoxazol-2-yl)oxy]phenoxy}propanoate |
| fenoxaprop-p | 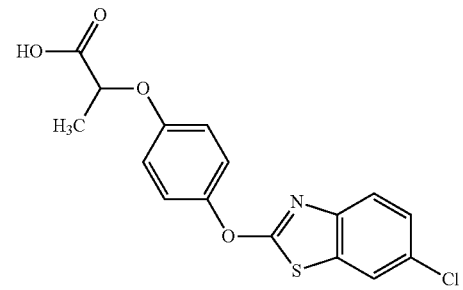 [SMILES: CC(Oc1ccc(Oc2nc3ccc(Cl)cc3s2)cc1)C(=O)O] | 2-{4-[(6-chloro-1,3-benzoxazol-2-yl)oxy]phenoxy}propanoic acid |

The present disclosure also includes pharmaceutically acceptable salts, hydrates, prodrugs, and mixtures of any of the above compositions. The term "pharmaceutically acceptable salt" refers to salts whose counter ion derives from pharmaceutically acceptable non-toxic acids and bases.

The arylphenoxypropionate derivatives, aryloxyphenoxyacetate derivatives, aryloxyphenylacetate derivatives, and substituted quinols which contain a basic moiety, such as, but not limited to an amine or a pyridine or imidazole ring, may form salts with a variety of organic and inorganic acids. Suitable pharmaceutically acceptable (i.e., non-toxic, physiologically acceptable) base addition salts for the compounds of the present invention include inorganic acids and organic acids. Examples include acetate, adipate, alginates, ascorbates, aspartates, benzenesulfonate (besylate), benzoate, bicarbonate, bisulfate, borates, butyrates, carbonate, camphorsulfonate, citrate, digluconates, dodecylsulfates, ethanesulfonate, fumarate, gluconate, glutamate, glycerophosphates, hemisulfates, heptanoates, hexanoates, hydrobromides, hydrochloride, hydroiodides, 2-hydroxyethanesulfonates, isethionate, lactate, maleate, malate, mandelate, methanesulfonate, 2-naphthalenesulfonates, nicotinates, mucate, nitrate, oxalates, pectinates, persulfates, 3-phenylpropionates, picrates, pivalates, propionates, pamoate, pantothenate, phosphate, salicylates, succinate, sulfate, sulfonates, tartrate, p-toluenesulfonate, and the like.

The arylphenoxypropionate derivatives, aryloxyphenoxyacetate derivatives, aryloxyphenylacetate derivatives, and substituted quinols which contain an acidic moiety, such as, but not limited to a carboxylic acid, may form salts with variety of organic and inorganic bases. Suitable pharmaceutically acceptable base addition salts for the compounds of the present invention include, but are not limited to, ammonium salts, metallic salts made from calcium, lithium, magnesium, potassium, sodium and zinc or organic salts made from lysine, N,N-dialkyl amino acid derivatives (e.g. N,N- dimethylglycine, piperidine-1-acetic acid and morpholine-4-acetic acid), N,N'-dibenzylethylenediamine, chloroprocaine, choline, diethanolamine, ethylenediamine, meglumine (N-methylglucamine), t-butylamine, dicyclohexylamine, hydrabamine, and procaine.

The arylphenoxypropionate derivatives, aryloxyphenoxyacetate derivatives, aryloxyphenylacetate derivatives, and substituted quinols, and salts thereof, may exist in their tautomeric form (for example, as an amide or imino ether). All such tautomeric forms are contemplated herein as part of the present invention.

The compounds described herein may contain asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as, their racemic and optically pure forms. Optically active (R)- and (S)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

Compositions of the present disclosure may also include a pharmaceutically acceptable carrier, in particular a carrier suitable for the intended mode of administration, or salts, buffers, or preservatives. Certain of the compounds disclosed herein are poorly soluble in water. Accordingly, aqueous compositions of the present disclosure may include solubility enhancers. Compositions for oral use may include components to enhance intestinal absorption. The overall formulation of the compositions may be based on the intended mode of administration. For instance, the composition may be formulated as a pill or capsule for oral ingestion. In other examples, the composition may be encapsulated, such as in a liposome or nanoparticle.

Compositions of the present disclosure may contain a sufficient amount of one or more one or more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof, to cause inhibition of a mycobacterium to occur when the composition is administered to the mycobacterium. The amount can vary depending on other components of the composition and their effects on drug availability in a patient, the amount of otherwise required to inhibit the mycobacterium, the intended mode of administration, the intended schedule for administration, any drug toxicity concerns, drug-drug interactions, such as interactions with other medications used by the patient, or the individual response of a patient. Many compositions may contain an amount well below levels at which toxicity to the patient becomes a concern.

The amount of arylphenoxypropionate derivative, aryloxyphenoxyacetate derivative, aryloxyphenylacetate derivative, substituted quinol, or pharmaceutically acceptable salt, hydrate, or prodrug thereof, or combination thereof, present in a composition may be measured in any of a number of ways. The amount may, for example, express concentration or total amount. Concentration may be for example, weight/weight, weight/volume, moles/weight, or moles/volume. Total amount may be total weight, total volume, or total moles. Typically, the amount may be expressed in a manner standard for the type of formulation or dosing regimen used.

Parasite Drug Sensitization and Inhibition Methods

The present disclosure also includes drug-sensitization and/or inhibition methods in which a composition comprising one or more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof, is administered to a parasite in order to sensitize the parasite to another drug or combination of drugs and/or to inhibit the parasite. The composition can be any composition described above. In certain embodiments, the composition can be administered with any other drug or drugs which can alternatively be present in a pharmaceutical composition as described herein. For example, the other drug can include ivermectin.

In methods in which a parasite is sensitized to a drug or drugs, the drug or drugs can be any drug or drugs for which rifamycin or a rifamycin derivative, such as rifabutin or a rifabutin derivative, or rifampicin or a rifampicin derivative, or a pharmaceutically acceptable salt, hydrate, or prodrug thereof, or a combination thereooneor more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof, increase sensitivity in a parasite. In certain embodiments, the drug or drugs can include an antiparasitic drug. Example types of suitable antiparasitic drugs and drug combinations include antinematodic drugs, anticestodic drugs, antitrematodic drugs, antiamamoebic drugs, antiprotazoal drugs, antihelminthic drugs, tiniacides, antiprotozoic drugs, and other drugs. Example classes of suitable antiparasitic drugs include benzimidazoles, avermectins, milbemycins, piperazines, octadepsipeptides, thiophenes, pamoates, spiroindoles, imadazothiazoles, quinines, biguanides, sulfonamides, tetracyclines, lincomycins, alkaloids, carbamates, formamidines, organophosphates, Rifampin, Amphotericin B, Melarsoprol, Eflornithine, Miltefosine, Metronidazole, Tinadadazole, Quinine-pyrithamine-sulfadiazine, Trimethoprin-sulfa methoxazole, Piperazine, Praziquantel Triclabendazole, Octadepsipeptides, Amino Acetonitrile derivatives and derivatives thereof.

Exemplary suitable antiparasitic drugs for use with the compositions and methods of the present disclosure include, without limitation, ivermectin, selamectin, doramectin, abamectin, albendazole, mebendazole, thiabendazole, fenbendazole, triclabendazole, flubendazole, diethylcarbazamine, niclosamide, suramin, pyrantel pamoate, levamisole, praziquantel, emodepside, monepantel, derquantel, rifoxanide, artemether, quinine, quinidine, chloroquine, amodiaquine, pyrimethamine, proguanil, sulfadozine, mefloquine, atovaquone, primaquine, artemisinin, doxycycline, clindamycin, sulfadoxine-pyrimethamine, moxidectin, permethrin, hexylresorcinol, and combinations thereof.

Accordingly, in certain embodiments, the antiparasitic drug or drugs to which sensitivity is increased in a parasite by the one or more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof, can include, without limitation, one or more of the antiparasitic drugs listed in Table 2 below, or any class or type referred to therein, or any antiparasitic drug referred to herein.

TABLE 2

Antiparasitic Drugs

| Antiparasitic Drug | Class/Type | Mechanism/Target |
|---|---|---|
| Trimethoprim | Anti-folate | Dihydrofolate reductase ("DHFR") |
| Pyrimethamine (Daraprim) | | |
| Proguanil (Paludrine) | | |
| Sulfamethoxazole | | deoxyhypusine synthase ("DHPS") |
| Sulfadiazine | | Sulfadoxine |
| Atovaquone (Mepron) | Ubiquinone Analog | Perturbs Mitochondrial Electron Transpot |
| Spiramycin (Rovmycin)- | Antibiotic | Ketolide Protein Synthesis Inhibitor |
| Azithromycin (Zithromax)- | | Macrolide Protein Synthesis Inhibitor |
| Paromomycin (Humatin)- | | Aminoglycoside Protein Synthesis Inhibitor |
| Clindamycin (Cleocin)- | | Lincosamide Protein Synthesis Inhibitor |
| Tetracycline (Sumycin)- | | Polyketide Protein Synthesis Inhibitor |
| Doxycycline (Vibramycin)- | | Polyketide Protein Synthesis Inhibitor |
| Metronidazole (Flagyl) | Nitroimidazole | PFOR-Dependent RNS Generation |
| Tinidazole (Tindamax) | | |
| Nitazoxanide (Alinia) | Nitrothiazole | |
| Iodoquinol (Yodoxin) | Quinoline | Iron chelation |
| Chloroquine | | Hemozoin Inhibitor |
| Primaquine | | |
| Mefloquine | | |
| Quinine | | |
| Quinidine | | |
| Praziquantel (Biltride)[1,2] | | Paralytic |
| Oxaminquine (Vansil)[1] | | |
| Triclabendazole (Egaten)[1] | Benzimidazole | Prevents tubulin polymerization |
| Niridazole[1] | Thiazole | Paralytic Phosphofructokinase Inhibitor |
| Stibophen[1] | Arylsulfonate | |
| Trichlorfon[1] | Organophosphate | Paralytic ACE Inhibitor |
| Mebendazole (Vermox)[2,3] | Benzimidazole | Prevents tublin polymerization |
| Albendazole (Albenza)[2,3] | | |
| Niclosamide[2] | Salicylanilide | Decouples Oxidative Phosphorylation |
| Ivermectin (Stromectol, Mectizan)[3,4] | Macroyclic Lactone | Paralytic GABA Agonist |
| Doxycycline (Vibramycin)[3] | Antibiotic | Targets Symbiotic Bacteria in Parasite Gut |
| Diethylcarbamazine (DEC)[3] | Piperazine | Perturbs Arachidonic Acid Metabolism |
| Pyrantel Pamoate (Helmex)[3] | Tetrahydropyrimidine | Paralytic |
| Permethrin (Elimite, Nix)[4] | Pyrethroid | Neurotoxin via Na-Channel Binding |
| Tiabendazole[3,5] | Nitrothiazole | Fumarate reductase |
| Levamisole[3,5] | Imidazothiazole | Paralytic Ach agonist |
| Mibemycin[3] | Macrolide | Glutamate sensitive chloride channels |

[1]Anti-trematodal;
[2]Anti-cestodal;
[3]Anti-nematodal;
[4]Anti-ectoparasitic;
[5]Anti-helminthic In methods of the current disclosure, the parasite can be sensitized to a drug or drugs already known to inhibit the parasite, or it can be sensitized to a drug or drugs not previously used with that type of parasite. If the parasite is a drug-resistant parasite that has acquired or evolved a resistance to a drug, it can be sensitized to a drug that previously exhibited a decreased ability to inhibit the parasite. In certain embodiments, sensitization of the parasite to the drug occurs at least in part by P-gp inhibition.

In certain embodiments, the composition can directly inhibit the parasite instead of or in addition to causing drug-sensitization.

The parasite that undergoes drug-sensitization or inhibition can be any type of parasite. It may, for instance, be a helminth, such as a nematode, a trematode, or a cestode, a protozoa, or an arthropod (i.e., an ectoparasite). The parasite can be a parasite of any animal or plant. By way of example and not limitation, the parasite that undergoes drug-sensitization or inhibition can be a species of the genus *Plasmodium*, such as *Plasmodium falciparum, Plasmodium malariae, Plasmodium ovale,* and *Plasmodium vivax,* a species of the genus *Ascaris,* such as *Ascaris lumbricoides,* a species of the genus *Enterobius,* such as *Enterobius vermicularis,* a species of the genus *Trichinella,* such as *Trichinella spiralis,* a species of the genus *Haemonchus,* such as *Haemonchus contortus,* a species of the genera *Aphelenchoides, Ditylenchus, Globodera, Heterodera, Longidorus, Meloidogyne, Nacobbus, Pratylenchus, Trichodorus,* and *Xiphinema,* a species of the genus *Bursaphelenchus,* such as *Bursaphelenchus xylophilus,* a species of the genus *Fasciola,* such as *Fasciola hepatica,* a species of the genus *Coccidoides,* or a species of the genus *Onchocerca,* such as *Onchocerca volvulus.*

The parasite that undergoes drug-sensitization or inhibition can be any parasite. The parasite can be, for example, any parasite commonly referred to or known as a flea, a tick, a worm, a hookworm, a roundworm, a heartworm, a fluke, a mite, a spider, a beetle, a mosquito, a fly, or a bed bug.

Accordingly, in certain embodiments, the parasite that undergoes drug-sensitization or inhibition can be a protozoan parasite, such as, for example, the protozoan parasites of Table 3 below. In certain embodiments, the parasite that undergoes drug sensitization or inhibition can be a helminthic parasite (parasitic worm) such as, for example, the helminthic parasites of Table 4 below. In certain embodiments, the parasite that undergoes drug sensitization or inhibition can be an ectoparasite, such as, for example, the helminthic parasites of Table 5 below. In certain embodiments, multiple parasites of different species, genera, class, or other category can simultaneously undergo drug sensitization or inhibition in a single host harboring the multiple parasites.

TABLE 3

Representative Protozoan Parasites

| Parasite | Disease | Symptoms (humans) | Current Drug Regimen |
|---|---|---|---|
| Cryptosporidium hominis, parvum | Cryptosporidiasis | Diarrhea-causing parasites (typically asymptomatic) but deadly in susceptible pop. (AIDS, Children, etc.) | Uncomplicated: Nitazoxanide (Alinia) AIDS: Paromomycin (Humatin) w/ Azithromycin (Zithromax) Questionable Efficacy for both regimes. |
| Isosporiasis belli | Isosporiasis | Diarrhea-causing parasites (typically asymptomatic) but deadly in susceptible pop. (AIDS, Children, etc.) | #1: Trimethoprim-Sulfamethoxazole w/folinic acid (Leucovorin) #2: Pyrimethamine (Daraprim) w/ folinic acid (Leucovorin) |
| Cyclospora cayetanesis | Cycosporiasis | Diarrhea-causing parasites (typically asymptomatic) but deadly in susceptible pop. (AIDS, Children, etc.) | Uncomplicated: No Recognized Effective Treatment AIDS: Trimethoprim-Sulfamethoxazole w/folinic acid (Leucovorin) considered effective at reducing severity. Control HIV infection to resolve parasite infestation. |
| Toxoplasma gondii | Toxoplasmosis | Usually asymptomatic but causes fatal encephalitis in AIDS/Immunocompromised Patients. TORCH Pathogen associated with transplacental infection. | Uncomplicated: Pyrimethamine (Daraprim) + sulfadiazine/clindamycin (Cleocin)/ azithromycin (Zithromax) Pregnancy: Uncomplicated + Spimmycin (Rovamycin) AIDS: Pyrimethamine (Damprim) + sulfadiazine/clindamycin (Cleocin)/ azithromycin (Zithromax). Treat patient indefinitely once Dx. *** All regimes require folinic acid (Leucovorin) *** |
| Balantidium coli | Balantidiasis | Diarrhea, Constiption. Can mimick inflammatory bowel conditions. | #1: Tetracycline (Sumycin) #2: Metronidazole (Flagyl) #3: Iodoquinol (Yodoxin) |
| Entamoeba histolytica, dispar | Amebiasis | Typically asymptomatic but can cause wide range of symptoms ranging from mild diarrhea to severe dysentery with mucoid, bloody diarrhea. May cause ameobic liver abscesses w/ or w/o intestinal disease. | Asymptomatic. Luminal Agents Iodoquinol (Yodoxin) or paromomycin (Humatin) Symptomatic: Colitis & Hepatic Abscess Metronidazole (Flagyl) + Luminal Agents. |
| Giardia lamblia | Giardiasis | ⅔ Asymptomatic. Others experience diarrhea varying in severity, sulfurous gas/belches, weight loss, cramping, pain, etc. Traveler's Diarrhea. | Metronidazole (Flagyl) |
| Trichmonas vaginalis | Trichomoniasis | Very common STI that is usually asymtomatic but can cause vaginits, urethritis, etc. | #1 Metronidazole (Flagyl) #2 Tinidazole (Tindamax) |
| Dientamoeba fragilis | Dientamoebiasis | Traveler's diarrhea, chronic diarrhea/abdominal pain, failure to thrive. | Prophylaxis: Paromomycin (Humatin) Symptomatic: Iodouinol (Yodoxin), Paromomycin (Humatin), Tetracycline (Sumycin), Metronidazole (Flagyl) combination of any two. |
| Blastocystis hominis | Blastocystosis | Typically nonsymptomatic and colonization transient. Nonspecific GI symptoms including diarrhea, flatulence, pain, etc. | Metronidazole (Flagyl) now considered ineffective. Nitazoxanide (Alinia) possible replacement (trials ongoing) |
| Plasmodium falciparum, vivax, ovale, malariea | Malaria | Classical paroxysm (cyclic fevers) w/headache, joint pain, vomiting, hemolytic anemia, jaundice, and convulsions. Neurological signs in severe cases. Presents 1-3 weeks post infection w/o prophylaxis. | Hemozoin Inhibitors: Chloroquine (I), Primaquine (II), Mefloquine (I), Quinine (I), Quinidine Gluconate (I). Antifolates: sulfadoxine (I), sulfamethoxypyrazine (I) + proguanil (II) or pyrimethamine (I). Sespuiterpene Lactones: Artemether, Artesunate, |

TABLE 3-continued

Representative Protozoan Parasites

| Parasite | Disease | Symptoms (humans) | Current Drug Regimen |
|---|---|---|---|
| | | | Dihyroartemisin, Artemotil, Artemisin (II) None FDA Approved. Naphthopuinonones: Atovaquone (II) Adjuncts: Tetracycline/Doxycycline, Clindamycin (Lincosamides). Proven Schizoticides. Use when indicated for Severe Disease. |
| *Babesia divergens, microfti*, other | Babesiosis | Typically asymptomatic (>50%) with others developing malaria-like illness w/ hemolytic anemia, cyclic fevers, thrombocytopenia, and possible organ failure 1-4 weeks post infection. | Mild/Moderate: Atovaquone (Mepron) w/Azithromycin (Zithromax) Severe: Quinine Sulfate w/ Clindamycin (Cleocin) |
| *Trypanosoma brucei* | African Trypanosomiasis (Sleeping Sickness) | Hemolymphatic phase with fever, headache, pains, and fever followed by CNS involvement. Fatal if not treated promptly. | No CNS *T.b. rhodesiense*: Suramin No CNS *T.b. gambiense*: Pentamidine CNS *T.b. rhodesiense*: Melarsoprol (Mel B, Arsobal) CNS *T.b. gambiense*: Eflomithine (DFMO, Ordinyl) |
| *Trypanosoma cruzi* | American Trypanosomiasis (Chaga's Disease) | Acute disease usually asymptomatic but cagoma/Romana's Sign may be present. Chronic infection destroys myenteric complex causing megaesophaug, colon, other dilations and dilated cardiomyopathy. | #1: Nifurtimox (Lampit) #2: Benzidazole (Rohagan) Both drugs can effect radical cure in acute phase but become less effecitve in chronic patients (especially those who have been infected for longer periods of time) |
| *Leishomania mexicana, aethiopica, tropic, braziliensis, donovani, infantum.* | Leishmaniasis | Cutaneous, mucocutaneous, difffuse cutaneous, and viseral (Kala Azar) Presentations | Classical Tx: Sodium Stibogluconate + pentavalent antimony (Pentostam) w/meglumine antimonate (Glucontime). Retired due to tox & resistance. Cutaneous Local: Topical paromomycin + gentamicin formulation. Oral Systemic: Miltefosine (Impavido) w/azoles ketoconazole, itraconazole, fluconazole IV Systemic: Amphotericin B (Ambisome) |

TABLE 4

Representative Helminthic Parasites

| Parasite | Disease | Symptoms (humans) | Current Drug Regimen |
|---|---|---|---|
| *Schistosoma mansoni, japonicum, haemotobium* | Schistosomiasis | Direct skin penetration in aquatic soils, etc. with infected fresh-water snails resulting in prolonged colonizationof the intestines/urinary tract dependent on species. Causes malnutiriton, organ damage, and associated with bladder cancer. | Praziquantel (Biltride) |
| *Trichobilharzia regenti* | Swimmer's Itch | Direct skin penetration in aquatic soils, etc. with infected fresh-water snails. Mild w/localized skin irritation. | Antihistamines No specific treatment |
| *Clonorchis simensis* | Clonorchiasis | Following ingestion of raw fish, colonize biliary tract. Associated with cholangiocarcinoma, liver damage, etc. | #1: Praziquantel (Biltride) #2: Albendazole |

TABLE 4-continued

Representative Helminthic Parasites

| Parasite | Disease | Symptoms (humans) | Current Drug Regimen |
|---|---|---|---|
| *Fasciola hepatica, gigantica* | Fascioliasis | Liver dysfunction, pain following colonization of the liver and biliary tract | Triclabendazole (Egaten) |
| *Opisthorchis viverrinil* | Opisthorchiasis | Following ingestion of raw fish, colonize biliary tract. Associated with cholangiocarcinoma, liver damage, etc. | #1: Praziquantel (Biltride) #2: Albendazole |
| *Paragonimus westermani, kellicotti* | Paragonimiasis | Liver, Lung dysfunction w/ pulmonary manifestations in chronic infections. | #1: Praziquantel (Biltride) #2: Triclabendazole (Egaten) |
| *Fasciolopsis buski* | Fasciolopisiasis | Typically asymptomatic but can include diarrhea, abdominal pain, obstruction. | Praziquantel (Biltride) |
| *Metagonimus yokagawai* | Metagonimiasis | Diarrhea, colic, obstruction. | Praziquantel (Biltride) |
| *Heterophyes heterophyes* | Heterophyiasis | Diarrhea, colic, obstruction. | Praziquantel (Biltride) |
| *Echinococcus granulosus, multilocularis* | Echinocccosis | Typically asymptomatic with formation of large cysts containing parasites. Rupture results in allergic reaction/anaphylaxis. Can behave like slow-growing destructive tumors. | Cystic: Albendazole (Albenza) w/ Surgical resection of cysts. Add Praziquantel (Biltride) if cyst spillage occurs during surgery. Alveolar: Albendazole (Albenza) or Mebendazole (Vermox) |
| *Taenia saginata, solium, asiatica* | Taeniasis | Tapeworms acquired from eating undercooked beef and sizes causing malnutrition, obstruction, etc. | Praziquantel (Biltride) |
| *Taenia solium, asiatica* | Cysticerosis | Occur following infection with pork tapeworms. All tissues susceptible to cyst infestation. CNS/CVS most dangerous. | Praziquantel (Biltride) w/prednisone |
| *Hymenolpeis nana, diminuta* | Hymenolepiasis | Asymptomatic dwarf tapeworm. Extremely common. | #1: Praziquantel #2: Niclosamide #3: Nitazoxanide |
| *Diphyllobotrium latum, mansonoides* | Diphyllobothriasis | Freshwater fish tapeworm. Largest of all tapeworms and can cause obstruction, B12 def. w/ megaloblastic anemia. | Praziquantel |
| *Spirometra erinaceieuropaei* | Sparganosis | Asymptomatic unless worms migrate to CNS. Typically nonspecific skin irritation as worms migrate. | No drug treatment. Surgical removal of worms required. |
| *Dracunculus medinensis* | Dracunculiasis | Guinea Worms. Enough said, | No drug treatment. "Stick Therapy" to remove erupting worms from lower extremities. |
| *Onchocerca volvulus* | Onchocerciasis | River Blindess | Ivermectin (Stromectol) & Doxycycline (Vibramycin) |
| *Loa loa* | Loiasis | Asymptomatic Eye Worm | Diethylcarbamazine |
| *Mansonella perstans, ozzardi, streptocera* | Mansonellosis | Swelling, nonspecific skin symptoms, rashes, typically asymptomatic. | #1: Mebendazole (Vermox) or Albendazole (Albenza) #2: Ivermectin (Stromectol) *** Include doxycycline (Vibramycin) w/#1 or #2 *** |
| *Wucheria bancrofti, Brugia malayi, timori* | Lymphatic Filariasis | Typically asymtomatic but some develop profound lymphatic obstruction and lymphadema (Elephantiasis) w/episodes of febrile/afebrile lymphangitis and lymphadenitis. Nocturnal cough associated with migrating worms. | Ivermectin (Stromectol) w/ Deithylcarbamazine (DEC) Typically responds poorly to drugs once lymphedema sets in. |
| *Gnathostoma spinigerum, hispidium* | Gnathostomiasis | Painful, intermittent, itchy swellings caused by migrating worms. Possible VLM organism. | #1: Ivermectin (Stromectol) #2: Albendazole (Albenza) |
| *Ancylostoma duodenale, brazilienes* | Ancylostomiasis and Cutaneous Larva Migrans | Signs of iron-deficiency anemia, malnutrition, and skin manifestations following infection by penetration of intact skin from infected soil. (Hookworms) | #1: Albendazole (Albenza) #2: Mebendazole (Vermox) #3: Pyrantel Pamoate (Helmex) |

TABLE 4-continued

Representative Helminthic Parasites

| Parasite | Disease | Symptoms (humans) | Current Drug Regimen |
|---|---|---|---|
| Necator americanus | Necatoriasis | Signs of iron-deficiency anemia, malnutrition, and skin manifestations following infection by penetration of intact skin from infected soil. (Hookworms) | #1: Albendazole (Albenza) #2: Mebendazole (Vermox) #3: Pyrantel Pamoate (Helmex) |
| Angiostrongylus cantonensis | Angiostrongyliasis | Abdominal disease and eosinophilic meningitis presentations possible. | #1: Albendazole (Albenza) #2: Mebendazole (Vermox) *** w/prednisolone *** |
| Ascaris lumbricoides | Ascariasis | Typically asymptomatic w/ nonspecific respiratory symptoms during pulmonary stage followed by adominal pain and possible obstrcution of biliary tract and/or intestines. | #1: Abendazole (Albenza) #2: Mebendazole (Vermox) #3: Ivermectin (Stromectol) |
| Toxocara canis, cati | Toxocariasis and Visceral Larva Migrans | Typically asymptomatic. VLM very serious depending on what organ is invaded. Non-VLM show generalized signs of worm infestations. | #1: Ivermectin (Stromectol) #2: Albendazole (Albenza) |
| Strongyloides stercoralis | Strongyloidiasis | Typically asymptomatic w/ mild GI symptoms including pain and diarrhea. May present with rashes. | #1: Mebendazole (Vermox) #2: Albendazole (Albenza) |
| Enterobius vermicularis | Enterobiasis | Typically asymptomatic w/ pruitic perianal region and possible superinfections. | #1: Albendazole (Albenza) #2: Mebendazole (Vermox) #3: Pyrantel Pamoate (Helmex) |
| Trichinella spiralis | Trichinellosis | Acquired from undercooked pork resulting in tissue infestation following actue GI symptoms. Larval encystments cause organ-specific symptoms. | #1: Mebendazole (Vermox) #2: Albendazole (Albenza) |
| Trichuris trichiura | Trichuriasis | Typically asymptomatic but heavy infections may cause GI symptoms. | #1: Mebendazole (Vermox) or #2: Albendazole (Albenza) #3: Ivermectin (Stromectol) |

TABLE 5

Representative Ectoparasites

| Parasite | Disease | Symptoms (humans) | Current Drug Regimen |
|---|---|---|---|
| Pedicululs humanus capitus, humanus | Pediculosis | Head lice, body lice spread by direct contact with either infected persons or infested bedding, clothing, hats, etc. | Permethrin (Elimite, Nix, Acticin, etc.) OTC any 1% formulation topical only. |
| Phthiriasis pubis | Phthiriasis | Pubic lice or "Crabs" spread by direct contact (sexual). | Permethrin (Elimite, Nix, Acticin, etc.) OTC any 1% formulation topical only. |
| Sarcoptes scabiei | Scabies | Mite infests stratum corneum with reaction resulting immune forming itchy blisters/lesions. | #1: Rx Permethrin (Elimite, Lyclear, Nix) Any 5% formulation. #2: Crotamiton (Eurax, Crotan) #3: Lindane 1% #4 Ivermectin (Stromectol) for Norwegian variant. |

The organism may also be *Eimeria vermiformis*.

The composition can be delivered to the parasite in a host organism by delivering the composition to the host organism, such as by administering, feeding, injecting, topical application, attachment, or providing for inhalation. In certain embodiments, the composition contacts the parasite by diffusion throughout the host organism after administration. Additionally or alternatively, the composition can be delivered to a recipient prophylactically, i.e., prior to recipient infection, or contact with, or exposure to, the parasite. The mode of delivery can be selected based on a number of factors, including metabolism of one or more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof, or another drug in the composition, the mode of administration of other drugs to the host organism, such as the drug to which the parasite is sensitized, the location and type of parasite to be drug-sensitized, the health of the host organism, the ability or inability to use particular dosing forms or schedules with the host organism, preferred dosing schedule, including any adjustment to dosing schedules due to side effects of other drugs, and ease of administration. In certain embodiments, the mode of administration can be enteral, such as orally or by introduction into a feeding tube. In certain embodiments, the mode of administration can be parenteral, such as intravenously. In certain embodiments, the mode of administration is transcutaneous. In certain embodiments, the mode of administration is topical. In certain embodiments, the mode of administration is by affixing a dosage form to the to body of an infected or susceptible animal, such as a collar or tag.

The dosage amounts of the and administration schedule of the one or more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof, can vary depending on other components of the composition and their effects on drug availability in a recipient, the type of drug or drugs to which the parasite is sensitized, the intended mode of administration, the intended schedule for administration, when other drugs are administered, any drug toxicity concerns, and the recipient's response to the drug. In certain embodiments, the amount and frequency of delivery of one or more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof, can be such that levels in the recipient remain well below levels at which toxicity to the recipient becomes a concern. However the amount and frequency can also be such that the levels of one or more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof, in the recipient remain continuously at a level sufficient to induce drug-sensitization or are at a level sufficient to induce drug sensitization when or shortly after the drug to which the parasite is sensitized is delivered to it. Accordingly, the composition can be taken on a regular basis during treatment with the drug to which the parasite is sensitized or it can be taken only a set time before, at the same time, or a set time after the drug to which the parasite is sensitized.

In certain embodiments, the administration of the arylphenoxypropionate derivative, aryloxyphenoxyacetate derivative, aryloxyphenylacetate derivative, substituted quinol, or pharmaceutically acceptable salt, hydrate, or prodrug thereof, or combination thereof, is calibrated to reach a threshold concentration in the plasma or tissue of a patient. Such calibration can take into consideration experimentally derived bioavailability, such as the exemplary study data provided below, as well as the mass of the patient. In certain embodiments, the threshold concentration is a proportion of the minimum inhibitory concentration ($MIC_{50}$).

In certain embodiments, and based on one or more of the considerations discussed, the unit dosage of the arylphenoxypropionate derivative, aryloxyphenoxyacetate derivative, aryloxyphenylacetate derivative, substituted quinol, or pharmaceutically acceptable salt, hydrate, or prodrug thereof, or combination thereof, is between about 1 mg/kg body weight to about 500 mg/kg body weight. In certain embodiments, the unit dosage is between about 5 mg/kg to about 350 mg/kg. In certain embodiments, the unit dosage is between about 10 mg/kg and about 200 mg/kg body weight.

The present disclosure further includes methods of identifying whether an arylphenoxypropionate derivative, aryloxyphenoxyacetate derivative, aryloxyphenylacetate derivative, substituted quinol, or pharmaceutically acceptable salt, hydrate, or prodrug thereof, or combination thereof, is able to inhibit a parasite. Such methods include preparing or obtaining such a derivative, applying it to the parasite, and identifying that the derivative inhibits the parasite.

Representative $MIC_{50}$ data for certain arylphenoxypropionate derivatives in *Cryptosporidium parvum* (CP) are provided below. In certain embodiments, the arylphenoxypropionate derivative, aryloxyphenoxyacetate derivative, aryloxyphenylacetate derivative, substituted quinol, or pharmaceutically acceptable salt, hydrate, or prodrug thereof, or combination thereof, has an $MIC_{50}$ value against CP of about 0.01 μM to about 20 μM, or about 0.1 μM to about 15 μM, or about 0.5 μM to about 12.5 μM, or about 1 μM to about 10 μM.

EXAMPLES

The following examples are provided to further illustrate certain embodiments of the disclosure. They are not intended to disclose or describe each and every aspect of the disclosure in complete detail and should be not be so interpreted. Unless otherwise specified, designations of cells lines and compositions are used consistently throughout these examples.

Example 1—Synthesis of Aryloxyphenoxyacetate Derivatives

Aryloxyphenoxyacetate derivatives can be prepared according the following scheme:

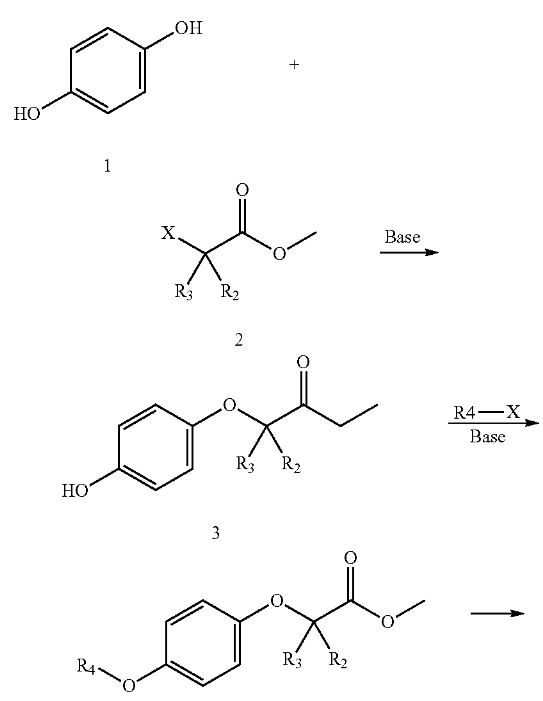

1

2

3

4

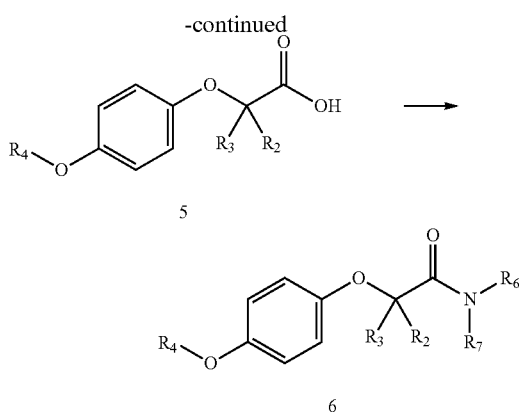

The compounds (3) are synthesized by condensation of hydroquinone (1) with chloro- or bromo-substituted acetate (2) at a temperature range from 5° C. to 120° C. in water, or organic solvent, such as DMF, DMSO, ethanol, in the presence of base, such as NaOH, $K_2CO_3$, or NaH. Substitution of compounds (3) with aromatic chloride or bromide (R4-X) in organic solvent, such as DMF, DMSO, dioxane, acetonitril, ethanol in the presence or absence of a catalyst, such as CuI, at a temperature range from 25° C. to 150° C. in the presence of base, such as $K_2CO_3$. $Li_2CO_3$, LiOH, KOH, produces ester (4). Hydrolysis of ester (4) will give acid (5). Coupling of acid (5) with amine in the presence of coupling reagents, such as EDCI, CDI or via acyl chloride in organic solvent, such as DCM, THF, DMF, produces amide (6).

Other aryloxyphenoxy or aryloxyphenyl -acetate, -acetyl amide, -acyl sulfonamide can be prepared by similar methods. It is apparent to one skilled in art that other sequence of the reactions, and alternative reagents can be used for the synthesis of compounds of the present disclosure. These alternatives for the synthesis of the derivatives are within the scope of this invention.

Aryloxyphenyl urea or cabamate derivatives can be prepared according the following schemes:

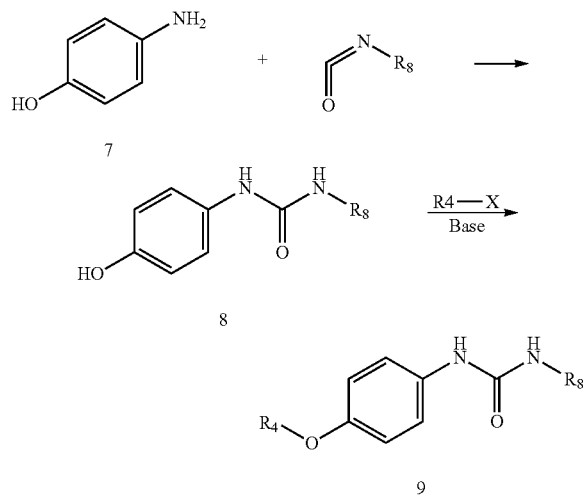

The compound (8) are synthesized by reaction of aminophenol (7) with isocyanate in organic solvent, such as DMF, dioxane, acetonitril, ethanol, THF, methanol, ethyl acetate, dichloromethane, or toluene, in the presence or absence of base, such as K2CO3, NaHCO3, triethylamine at a temperature range from 5° C. to 120° C. Substitution of compounds (8) with aromatic chloride or bromide (R4-X) in organic solvent, such as DMF, DMSO, dioxane, acetonitril, ethanol in the presence or absence of a catalyst, such as CuI, at a temperature range from 25° C. to 150° C. in the presence of base, such as $K_2CO_3$. $Li_2CO_3$, LiOH, KOH, produces Aryloxyphenyl urea derivatives (9).

Example 2—*Cryptosporidium* Testing

Cell Culture Model of *Cryprosporodium parvum* Infection

Fresh oocysts of CP (Iowa strain) were purchased from Bunch Grass Farm (Deary, ID). Oocysts were further purified by a Percoll-based gradient centrifugation method and surface sterilized with 10% bleach for 7 min on ice, followed by washes with phosphate-buffered saline (PBS). An ileocecal colorectal adenocarcinoma cell line (HCT-8, ATCC # CCL-244) was used to host the growth of CP in vitro. One day before the inoculation, HCT-8 cells were seeded in 96-well plates ($2.5 \times 10^4$/well) containing RPMI 1640 medium supplied with 10% fetal bovine serum (200 μL medium/well in all experiments) and allowed to grow overnight at 37° C. under 5% $CO_2$ atmosphere until they reached ~90% confluence. For drug testing, host cells were infected with $1.5 \times 10^4$ oocysts per well (ratio ~1:3). After inoculation, parasite oocysts were allowed to undergo excystation and invasion into host cells for 3 h at 37° C. Free parasites and oocyst walls in the medium were removed from the plates by an exchange of the culture medium. Drugs at specified concentrations were added into the culture at this time point (immediately after the medium exchange). Parasite-infected cells were then incubated at 37° C. for additional 41 h (total 44 h infection time). At least two independent experiments were conducted for every experimental condition, each including two replicates drugs and eight replicates for negative controls.

Preparation of Cell Lysates

Plates containing HCT-8 cells infected with CP for 44 h were first centrifuged for 10 min at 1000×g to ensure that free merozoites in the medium were firmly settled on the bottom of the wells. Medium was removed, followed by two gentle washes with PBS. For extracting total RNA, 200 μL of ice-cold Bio-Rad iScript qRT-PCR sample preparation reagent (lysis buffer) (Bio-Rad Laboratories, Hercules, Calif.) was added into each well. Plates were sealed with heat sealing films and subjected to vortex for 20 min. Plates were then incubated at 75° C. for 15 min, followed by centrifugation (5 min, 2000×g) to settle down cell debris. Supernatants were used immediately in subsequent qRT-PCR reactions or the plates were stored at −80° C. until use.

Real-Time qRT-PCR Assay

The levels of 18S rRNA transcripts from CP and host cells (referred to as Cp18S and Hs18S) were detected by real-time qRT-PCR method using gScript™ one-step SYBR green qRT-PCR kit (Quanta Biosciences, Gaithersburg, Md.). Cell lysates prepared as described above were diluted by 100 and 2000 folds for detecting Cp18S and Hs18S transcripts, respectively. Reactions were performed in hard-shell 384-well skirted PCR plates (Bio-Rad Laboratories, Hercules, Calif.) (10 μL/well) containing 3 μL diluted cell lysate, 5 μL one-step SYBR green master mix, 0.2 μl RT master mix and the following primers: Cp18S-1011F and Cp18S-1185R primer pair for Cp18S rRNA, and Hs18S-1F and Hs18S-1R primer pair for Hs18S rRNA. Hs18S levels were used as controls and for normalization.

Real-time qRT-PCR reactions were performed by a Bio-Rad CFX384 Touch Real-Time PCR Detection System. The reactions started with synthesizing cDNA at 50° C. for 20 min, followed by 5 min at 95° C. to denature RNA-cDNA hybrids and deactivate reverse transcriptase, and 40 two-temperature thermal cycles of PCR amplification at 95° C., 10 sec and 58° C., 30 sec. At the end of PCR amplification, melting curve analysis was performed between 65° C. to 95° C. At least 2 technical replicates were included in qRT-PCR reactions for each sample.

After qRT-PCR reactions were completed, amplification curves and melting peaks were examined to assess the quality and specificity of the reactions, followed by the computation of relative parasite loads based on the cycle threshold ($C_T$) values of Cp18S and Hs18S transcripts as previously described. qRT-PCR was used to quantify parasite 18S rRNA and $MIC_{50}$ was determined by the amount of compound resulting in 50% reduction of parasite growth compated to the control. The % inhibition (% inh @ (μM)) was calculated using a standard curve. No toxicity to the HCT-8 monolayers was observed.

TABLE 6

Cyryptosporidium Inhibition Data

| Compound | % inh @ (μM) | $MIC_{50}$ (μM) |
|---|---|---|
| NZ-259 | 33% @ 10 uM | >10 |
| NZ-261 | 60% @ 10 uM | ~10 |
| NZ-274 | 15% @ 10 uM | NA |
| NZ-278 |  | ~0.25 |
| NZ-289 | 88% @ 10 uM |  |
| NZ-295 | 61% @ 10 uM |  |
| NZ-302 | 60% @ 10 uM | ~10 |
| NZ-310 | 83% @ 10 uM |  |
| NZ-322 | 44% @ 0.9 uM |  |
| NZ-327 |  | 0.007 to 0.022 |
| NZ-331 | 36% @ 0.05 uM |  |
| NZ-332 |  | ~2.5 |
| NZ-364 |  | 0.12 |
| NZ-365 |  | 0.025 |
| NZ-366 |  | 0.05 |
| NZ-366 (peak 1) | 85% @ 0.05 uM | <0.05 |
| NZ-366 (peak 2) | 81% @ 0.05 uM | <0.05 |
| NZ-368 | 63% @ 0.125 uM | <0.125 |
| NZ-369 |  | 0.05 to 0.08 |
| NZ-369 (peak 1) |  | 0.07 |
| NZ-369 (peak 2) |  | ~0.2 |
| NZ-370 |  | 0.05 to 0.06 |
| NZ-371 |  | 0.15 to 0.23 |
| NZ-372 |  | 0.085 |
| NZ-386 |  | 0.05 to 0.3 |
| NZ-387 |  | ~0.44 |
| NZ-389 |  | ~1.1 |
| NZ-395 |  | ~5 |
| NZ-398 | 50% @ 10 uM | ~10 |
| NZ-399 |  | NA |
| NZ-400 | 67% @ 10 uM | ~10 |
| NZ-401 | 3% @ 4 uM | NA |
| NZ-403 | 63% @ 10 uM | ~10 |
| NZ-409 |  | ~0.44 |
| NZ-410 | 94% @ 10 uM | 2-10 |
| NZ-411 | 75.7% @ 10 uM |  |
| NZ-425 |  | 0.25 to 0.5 |
| NZ-426 |  | 0.25 to 1 |
| NZ-427 | 71% @ 0.25 uM | <0.25 |
| NZ-433 |  | ~2 |
| NZ-438 | 43% @ 0.25 uM | 0.25 to 1 |
| NZ-440 | 53% @ 10 uM | ~10 |
| NZ-446 |  | 1-4 |
| NZ-450 |  | ~2 |
| NZ-458 |  | NA |
| NZ-459 |  | 1 |
| NZ-460 | 19% @ 5 uM | NA |
| NZ-464 |  | 0.05 to 0.27 |
| NZ-465 | 68% @ 0.25 uM | <0.25 |
| NZ-466 |  | 0.05 to 0.1 |
| NZ-467 |  | 0.25-1 |
| NZ-469 | 82% @ 0.25 uM | <0.25 |
| NZ-471 | 89% @ 4 uM | 1-4 |
| NZ-472 |  | ~1 |
| NZ-475 |  | 0.06 |
| NZ-476 |  | ~0.5-1 |
| NZ-477 |  | 0.05 to 0.17 |
| NZ-479 |  | ~0.5-1 |
| NZ-481 |  | 1-4 |
| NZ-484 |  | ~1 |
| NZ-485 |  | 1-4 |
| NZ-489 | 68% @ 0.25 uM | <0.25 |
| NZ-490 | 60% @ 0.25 uM | ~0.25 |
| NZ-496 |  | 0.25 to 1 |
| NZ-500 |  | ~0.25 |
| NZ-505 |  | ~0.25 |
| NZ-516 |  | 0.016 |
| NZ-518 | 32% @ 0.45 uM | >0.45 |
| NZ-521 |  | 0.25 |
| NZ-522 |  | 0.022 to 0.045 |
| NZ-528 |  | 0.45 to 0.9 |
| NZ-529 | 42% @ 0.45 uM | >0.45 |
| NZ-530 |  | ~0.225 |
| NZ-531 |  |  |
| NZ-532 |  | NA |
| NZ-533 |  | NA |
| NZ-534 |  | NA |
| NZ-535 |  | 0.225 to 0.45 |
| NZ-536 |  | NA |
| NZ-538 |  | 0.054 |
| NZ-539 |  | 0.057 |
| NZ-541 |  | 0.081 |
| NZ-542 |  | 0.112 |
| NZ-543 |  | 0.045 |
| NZ-544 |  | 0.072 |
| NZ-545 |  | 0.45 |
| NZ-546 | 76% @ 0.225 uM | <0.225 |
| NZ-547 | 96% @ 0.056 uM | <0.056 |
| NZ-548 | 45% @ 0.112 uM | 0.112 to 0.225 |
| NZ-553 |  | 0.002 |
| NZ-554 |  | 0.056 to 0.112 |
| NZ-555 | 79% @ 0.056 uM | <0.056 |
| NZ-556 | 64% @ 0.056 uM | ~0.056 |
| NZ-557 |  | 0.112 to 0.225 |
| NZ-558 |  | ~0.056 |
| NZ-561 |  | 0.04 |
| NZ-562 |  | ~0.45 |
| NZ-563 |  | 0.018 |
| NZ-564 |  | 0.054 |
| NZ-572 |  | ~0.5 |
| NZ-573 |  | ~0.5 |
| NZ-574 |  | ~1 |
| NZ-575 |  | ~1 |
| NZ-576 |  | ~0.03 |
| NZ-577 |  | ~0.25 |
| NZ-578 |  | 0.018 |

NA: not active

In general, compounds with a benzothiazole core inhibited CP better than those with a benzopyrazine core. In additions, benzothiazole cores substituted with 6-Cl inhibited CP better than benzothiazole cores with a 6-F or 5,6-di-f substitution. α-methyl substitution at phenyl acetic amides improved inhibition as compared to unsubstituted phenyl acetic amides, often decreasining $MIC_{50}$ to less than 100 nM.

Example 3—Additional Crytosporidium, Toxicity, Dosing, and Other Testing

Cell Toxicity Testing

S. cerevisiae cytotoxicity and human fibroblast cytotoxicity testing was performed. The following compounds were not toxic at concentrations at or above 100 μM in both S. cerevisiae cytotoxicity and human fibroblast cytotoxicity testing: NZ-251, NZ-274, NZ-287, NZ-289, NZ-290, NZ-293, NZ-294, NZ-295, NZ-296, NZ-298, NZ-299, NZ-300, NZ-301, NZ-302, NZ-304, NZ-305, NZ-306, NZ-307, NZ-308, NZ-309, NZ-310, NZ-311, NZ-312, NZ-313, NZ-314, NZ-315, NZ-316, NZ-317, NZ-318, NZ-319, NZ-320, NZ-321, NZ-322, NZ-323, NZ-325, NZ-326, NZ-327, NZ-328, NZ-329, NZ-330, NZ-331, NZ-332, NZ-334, NZ-335, NZ-337. NZ-361, NZ-362, NZ-363, NZ-364, NZ-369, NZ-370, NZ-371. NZ-373, NZ-374, NZ-376, NZ-377, NZ-378, NZ-379, NZ-380, NZ-381, NZ-383, NZ-385, NZ-386, NZ-387, NZ-388, NZ-389, NZ-390, NZ-391, NZ-392, NZ-393, NZ-394, NZ-395, NZ-396, NZ-397, NZ-398, NZ-399, NZ-400, NZ-401, NZ-402, NZ-403, NZ-404, NZ405, NZ-406, NZ-407, NZ-408, NZ-409, NZ-410, NZ-411, NZ-412, NZ-413, NZ-4 14, NZ-415, NZ-416, NZ-417, NZ-418, NZ-419, NZ-420, NZ-421, NZ-422, NZ-423, NZ-424, NZ-425, NZ-426, NZ-427, NZ-428, NZ-429, NZ-430, NZ-431, NZ-432, NZ-433, NZ-534, NZ-435, NZ-436, NZ-437, NZ-438, NZ-439, NZ-440, NZ-441, NZ-442, NZ-443, NZ-444, NZ-445, NZ-446, NZ-447, NZ-448, NZ449, NZ-450, NZ-451, NZ-452, NZ-453, NZ-454, NZ-455, NZ-456, NZ-457, NZ-458, NZ-459, NZ-460, NZ-461, NZ-462, NZ-463, NZ-464, NZ-465, NZ-466, NZ-467, NZ-468, NZ-469, NZ-470, NZ-471, NZ-472, NZ-473, NZ-474, NZ-475, NZ-476, NZ-477, NZ-478, NZ-479, NZ-480, NZ-481, NZ-481, NZ-482, NZ-483, NZ-484, NZ-485, NZ-486, NZ-487, NZ-488, NZ-489, NZ-490, NZ-491, NZ-492, NZ-493, NZ-494, NZ-495, NZ-496, NZ-497, NZ-498, NZ-499, NZ-500, NZ-501, NZ-502, NZ-503, NZ-504, NZ-505, NZ-506, NZ-507, NZ-508, NZ-509, NZ-510, NZ-511, NZ-512, NZ-513, NZ-514, NZ-515, NZ-516, NZ-517-NZ 578.

The following compounds were not toxic at concentrations at or above 100 μM in S. cerevisiae cytotoxicity testing: NZ-347, NZ-349, NZ-350, NZ-351, NZ-353, NZ-355, NZ-356, NZ-357, NZ-358, NZ-359, NZ-360, NZ-372.

The following compounds were not toxic at concentrations at or above 100 μM in human fibroblast cytotoxicity testing: NZ-303, NZ-338, NZ-341, NZ-342, NZ-343, NZ-345, NZ-346, NZ-368, NZ-365, NZ-382, fenoxaprop-p, fenoxaprop-p-ethyl.

The following compounds were not toxic at concentrations at or above 25 μM and at or below 50 μM in S. cerevisiae cytotoxicity testing: NZ-348, NZ-352, NZ-366, NZ-368.

The following compound was not toxic at concentrations at or above 25 μM and at or below 50 μM in human fibroblast cytotoxicity testing: NZ-366.

The following compounds were not toxic at concentrations at or above 50 μM and at or below 100 μM in S. cerevisiae cytotoxicity testing: NZ-336, NZ-354, NZ-365, NZ-382.

The following compound was not toxic at concentrations at or above 50 μM and at or below 100 μM in human fibroblast cytotoxicity testing: NZ-336.

A group of compounds found to be promising were subjected to further tests. These tests included an IL-12 mouse model test to determine compound efficacy, verification of $MIC_{50}$ for CP, cytotoxicity test for fibroblasts and yeast to determine potential toxic effects, a Human ether-a-go-go-related gene (hERG) test to determine potential cardiotoxicity, an AMES test tp determine mutagenic potential, a Safety Screen 44 test to determine common negative off-target drug interastion (Eurofins Cerep, SA, France), a cytochrome P450 (CYP) test to determine potential liver toxicity, a maximum tolerated dose, test, a Pharmacokinetics (PK) test to determine fate of the substance administered to a living organism tests for plasma stability in human and mouse, to measure the degradation of compound in plasma MClint and HClint test to determine in vitro intrinsic clearance for Mouse and Human, and kinetic solubility and plasma protein binding tests in mouse and human. Results are presented in Table 7.

TABLE 7

Basic Efficacy, Toxicity, and Dosing Test Results

| Compound | Mouse Model (Mead) | MIC50 (nM) (CP) | Fibroblast Cytotox (IC50) (uM) | Yeast Cytotox (IC50) (uM) | hERG (Abbvie) (uM) | MCLint, HCLint (mL/min/g liver) | Kinetic Sol. (uM) | PPB |
|---|---|---|---|---|---|---|---|---|
| NZ-366 | DPI7 = 59% @50 mg/kg | 50 | 48 | 80 | 2.4 | MLM = 41 HLM = 7.9 | 62 | 98.1% (mice) |
| NZ-369 | DPI7 = 70% @100 mg/kg | 80 | >100 | >100 | >30 | MLM = 3.3 HLM = 0.69 | 86 | 98.5% (mice) |
| NZ-516 | DPI7 = 94% @50 mg/kg | 16 | 5.6 | >100 | 2.7 | MLM = 4.1 HLM = 0.54 | 100 | |
| NZ-370 | | | 50-60 | >100 | >100 | 30 | MLM = HLM = | 40 | |
| NZ-365 | | | 25 | >100 | >100 | 12 | MLM = 10 HLM = 4.8 | 28 | |
| NZ-327 | | | 7-22 | >100 | >100 | | MLM = 3.7 HLM = 1.3 | 33 | 98.4% (mice) |
| NZ-538 | | | 54 | >100 | >100 | 7.3 | MLM = 3.9 HLM = 0.7 | | |
| NZ-539 | | | 57 | >100 | >100 | >30 | MLM = 4.4 HLM = 1.8 | | |
| NZ-541 | | | 81 | >100 | >100 | 27 | MLM = 6.3 HLM = 2.0 | | |

TABLE 7-continued

Basic Efficacy, Toxicity, and Dosing Test Results

| Compound | Mouse Model (Mead) | MIC50 (nM) | Fibroblast Cytotox (IC50) (CP) (uM) | Yeast Cytotox (IC50) (uM) | hERG (Abbvie) (uM) | MCLint, HCLint (mL/min/g liver) | Kinetic Sol. (uM) | PPB |
|---|---|---|---|---|---|---|---|---|
| NZ-543 | | 45 | >100 | >100 | 24.0 | MLM = 2<br>HLM = 1.2 | | |
| NZ-544 | | 72 | >100 | >100 | 11.0 | MLM = 3.3<br>HLM = 2.6 | | |
| NZ-553 | | 2 | 40 | >100 | 11.0 | MLM = 1.28<br>HLM = 0.87 | 100 | 99% (mice) |
| NZ-578 | | <30<br>83%<br>@31 uM | >100 | | | | | |

Example 4—Efficacy of NZ-366 and NZ-369 in an acute Cryptosporodosis Mouse Model To investigate the relationship between anticryptosporidial activity and systemic exposure the plasma pharmacokinetics for NZ-369 were measured. Compound NZ-369 had excellent systemic pharmacokinetics, with the greatest values of $C_{max}$ and $t_{1/2}$, for an overall area under the curve (AUC).

The pharmacokinetics of NZ-369 following single intravenous (IV) and oral administration (PO) at 3 and 10 mg free base/kg respectively to the female Balb/c mouse. PK parameters are presented in Table 8.

TABLE 8

PK Parameters for NZ-369

| | IV | PO |
|---|---|---|
| $C_{max}$ (ng/mL) | | 2159 |
| $T_{max}$ (hr) | | 2 |
| $T_{1/2}$ (hr) | 3.4 | |
| AUC0-24 (mg-min/mL) | 452102 | 1186472 |
| Clb (mL/min/kg) | 6.6 | |
| Vdss | 1.7 | |
| F (%) | 78.8 | |

The anticryptosporidial activity of the in vitro inhibitors was assessed in the IL-12 knockout mouse model that resembles the acute human disease (Ehigiator H N, Romagnoli P, Borgelt K, Fernandez M, McNair N, Secor W E, Mead J R. 2005. Mucosal cytokine and antigen-specific responses to *Cryptosporidium* parvum in IL-12p40 KO mice. Parasite Immunol. 27: 17-28; Campbell L D, Stewart J N, Mead J R. 2002. Susceptibility to *Cryptosporidium parvum* infections in cytokine- and chemokine-receptor knockout mice. J. Parasitol. 88:1014-1016). The protocol was approved by the Institutional Animal Care and Use Committees of Emory University, the AtlantaVAMedical Center, and Brandeis University. Mice (6 to 10 per group) were inoculated with 1,000 purified CP oocysts (Iowa isolate, from cattle). Treatment by gavage began 4 h postinfection with either vehicle (5% dimethyl sulfoxide (DMSO) in canola oil), 50-100 mg/kg compound, or 2,000 mg/kg paromomycin. Compounds were given for 7 days, and mice were sacrificed on day 8 (peak infection). Parasite load was quantified by fluorescence-activated cell sorting (FACS) assays for the presence of the oocysts in the feces at days 0, 4, and 7. Fecal pellets from individual mice were routinely collected daily and homogenized in adjusted volumes of 2.5% potassium dichromate. Samples were processed individually. Aliquots (200 ul) of vortexed samples were processed over microscale sucrose gradients as previously described (Arrowood M J, Hurd M R, Mead J R. 1995. A new method for evaluating experimental cryptosporidial parasite loads using immunofluorescent flowcytometry. J. Parasitol. 81:404-409). The oocyst-containing fraction was collected, washed, and treated with monoclonal antibody (OW5O-FITC) for 20 min. Samples were adjusted to 600 ul, and a portion (100 ul) was assayed with a 102-s sampling interval using logical gating of forward/side scatter and OW5O-FITC fluorescence signal on a Becton, Dickinson FACScan flow cytometer. Flow cytometry data were evaluated by analysis of variance (KaleidaGraph (Synergy Software, Reading Pa.); Microsoft Excel (Microsoft Corporation, Redmond, Wash.)).

NZ-366 (50 mg/kg) and NZ-369 (100 mg/kg) were administered via gavage in a single daily dose to IL-12 knockout mice that were infected with 1,000 CP oocysts. Additional control groups included those treated with single daily doses of vehicle, and paromomycin (Prm) (2,000 mg/kg), by oral gavage. Fecal oocysts were counted on day 7 post infection and these results demonstrated that the two compounds, NZ-366 and NZ-369, have anticryptosporidial activity in the acute IL-12 knockout mouse model of disease. Results are presented in FIG. 1. NZ-366 and NZ-369 were more effective than paromomycin, a current leading drug used to combat the parasite, when administered after a single dose, and equally as effective as paromomycin over the course of the study. As expected there was no overt toxicity noted in the mice. NZ-516, NZ-364, NX-475, and NZ-372 have also been shown to be effective in the same type of test.

Example 5—In Vivo Toxicity Evaluation of NZ-369

Compound toxicity was evaluated at 200 mg/kg of body weight in uninfected mice treated for 7 days (5 mice/group). Toxicity was assessed by weight loss and signs of distress (e.g., ruffled fur, hunched shoulders, and decreased appetite). No overt signs of toxicity were observed for any of the compounds. No significant changes in weight were observed between treated and vehicle control mice Example 6—Calf Studies of NZ-369

Figure 2:
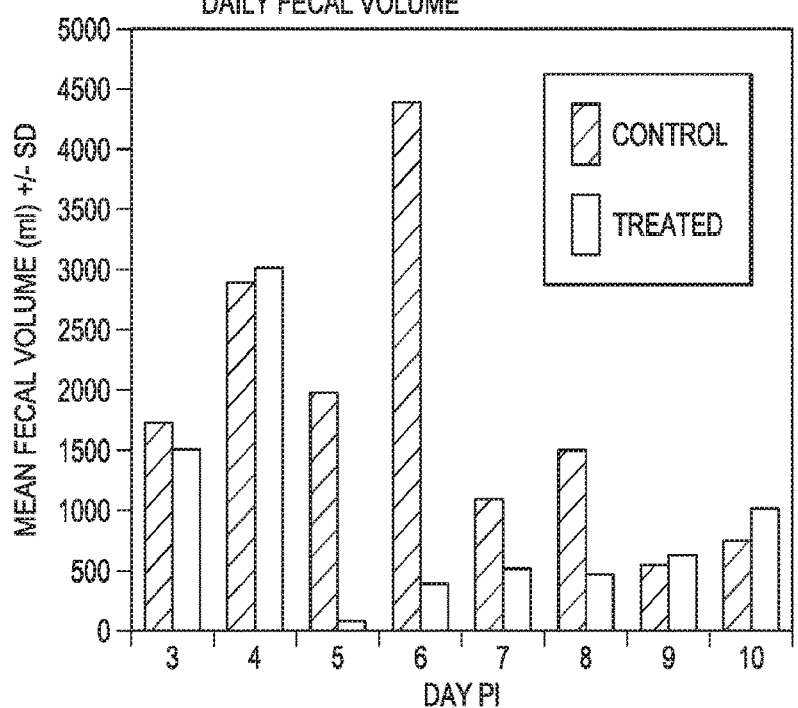
FIG. 2 is a graph of fecal volume vs. days post infection in calves with Cryptosporodosis treated with a control or test compound.

New born calves are susceptible to CP infection. They can develop severe diarrhea like humans. Calves were inoculated with $5 \times 10^7$ CP oocysts/calf on day 0. Calves had diarrhea in both the groups at onset of dosing. Treatment was started on day 3. Calves were given NZ-369 @ 8.5 mg/kg every 12 hrs for 5 days. Fecal volume, urine volume, daily clinical evaluation, fecal consistency scores and weight gains were evaluated. Results for fecal volume are presented in FIG. 2. The treatment and control calves had about the same fecal volume for the first two days of treatment, then the treatment calves treated with NZ-369 showed a marked reduction in fecal volume through day 8 post infection as compared to the control.

Figure 3:
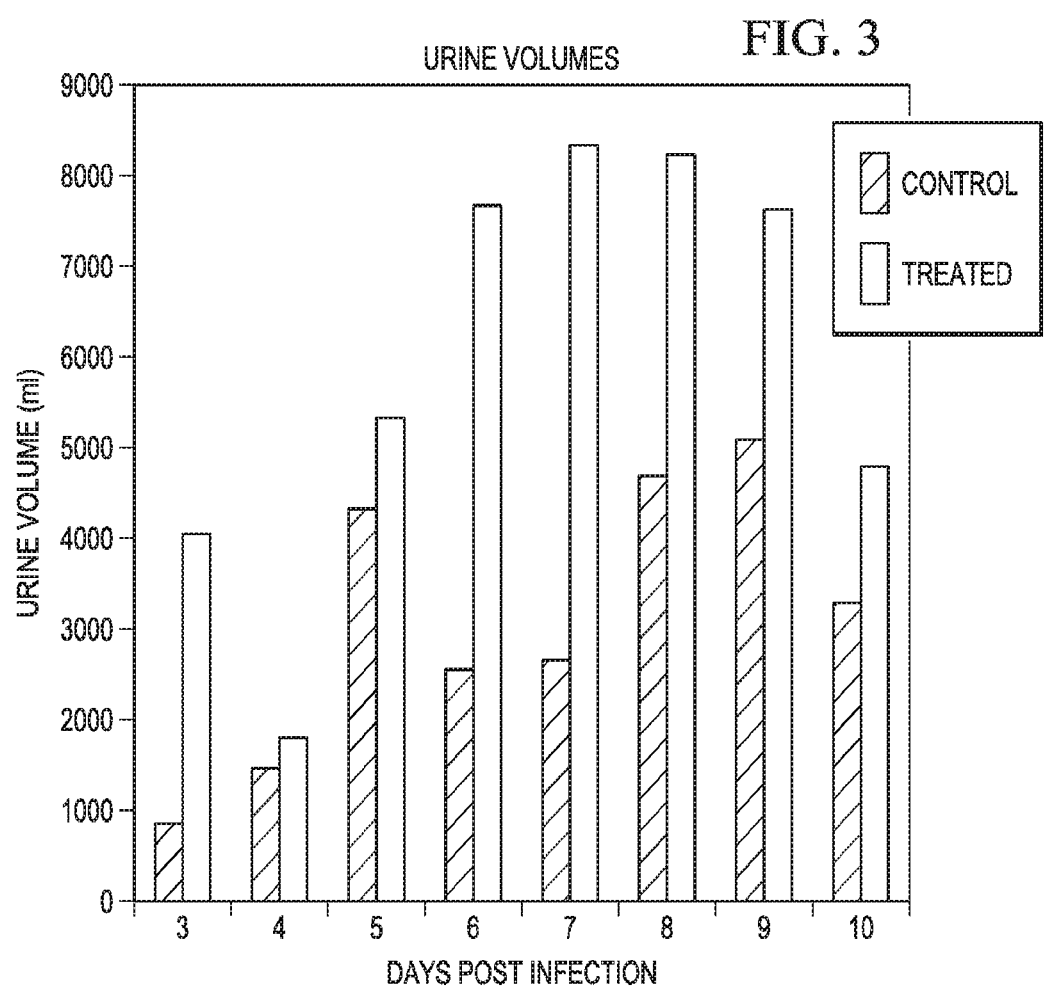
FIG. 3 is a graph of urine volume vs. days post infection in calves with Cryptosporodosis treated with a control or test compound.
Figure 4:
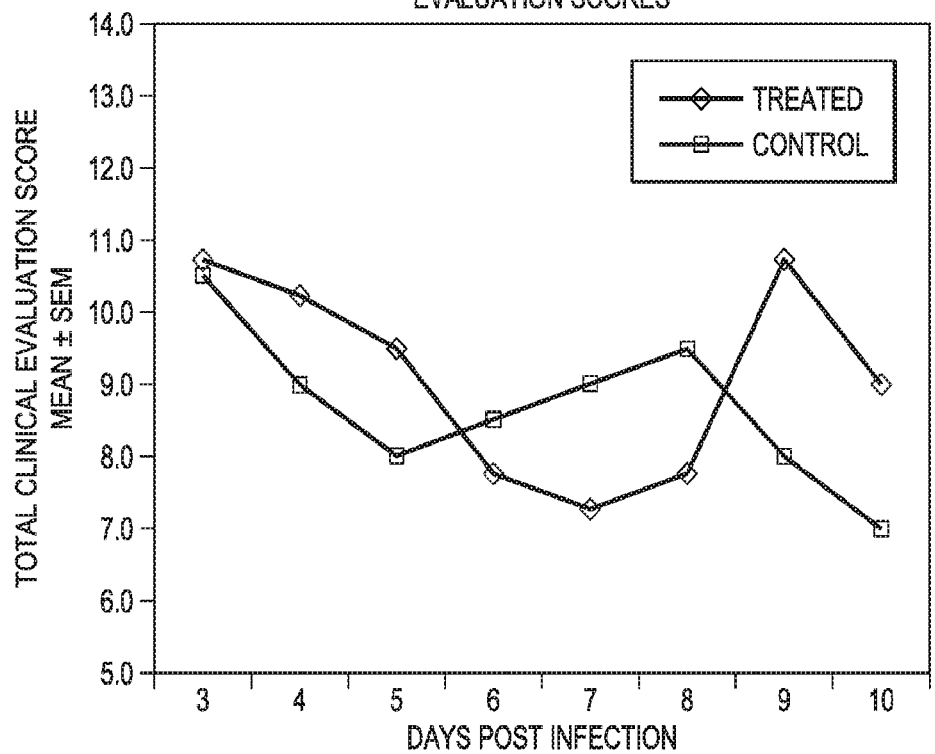
FIG. 4 is a graph of overall clinical evaluation vs. days post infection in calves with Cryptosporodosis treated with a control or test compound.

Greater urine output was seen in calves treated with NZ-369 than in control calves except on day 4 post-infection as shown in FIG. 3. Calves receiving NZ-369 also had higher clinical evaluation scores and greater improvement post-infection as shown in FIG. 4.

Figure 5:
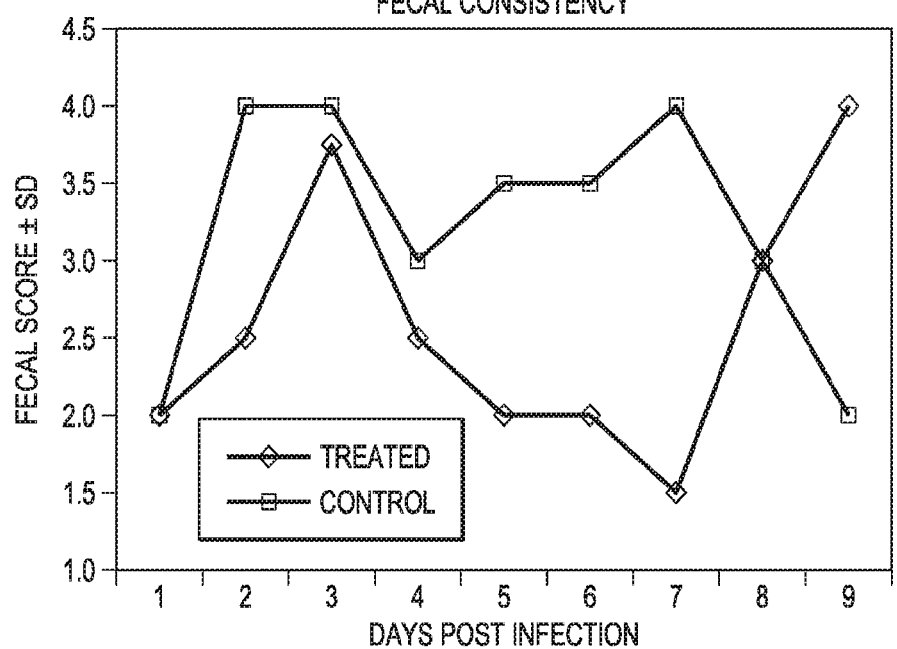
FIG. 5 is a graph of fecal consistency vs. days post infection in calves with Cryptosporodosis treated with a control or test compound.

A lower fecal consistency score, as shown in FIG. 5, was observed in the NZ-369 treated calved compared with control calves on days 4-7 post infection, which demonstrates decreased diarrhea with NZ-369 therapy.

Figure 6:
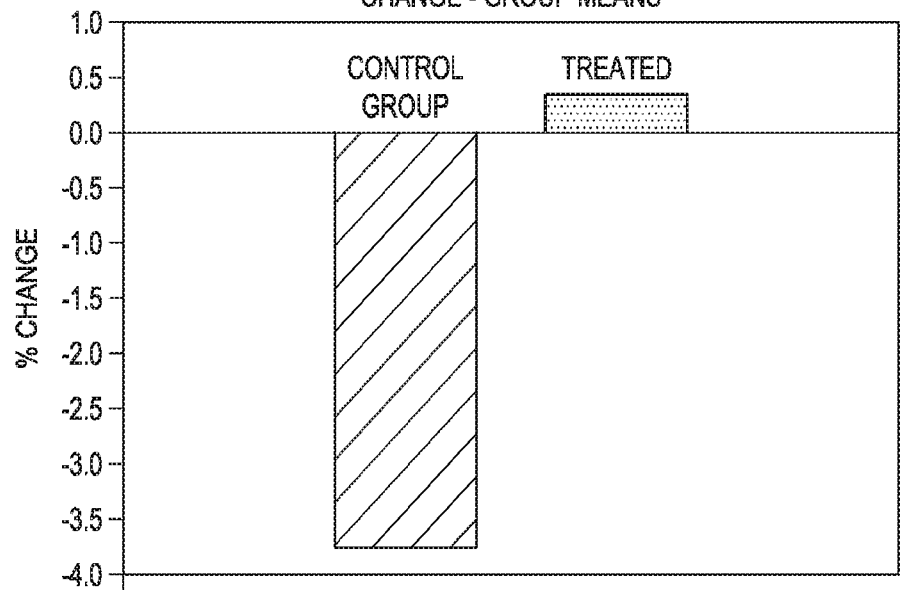
FIG. 6 is a graph of percent weight change over a trial period in calves with Cryptosporodosis treated with a control or test compound.

As shown in FIG. 6, calves treated with NZ-369 maintained their weight over the trial period compared to the control calf. Treatment calves actually gained a slight amount of weight compared to the control calf.

Example 7—Eimeriosis Testing in Chickens

Eimeriosis, often also referred to as coccidiosis, is the disease caused by *Eimeria* parasites resulting in severe mucosal damage, weight loss and sometimes even death. The disease is widespread and many species are found in poultry, livestock and small animals. Infections with *Eimeria* sp. confined to the distal ileum and/or the large bowel can often result in intermittent diarrhoea or even be asymptomatic. Infections may often involve the pyloric region of the gastric mucosa. Parasite forms displace the microvillus border and eventually lead to the loss of the mature surface epithelium. The rapid loss of surface epithelium causes marked shortening and fusion of the villi and lengthening of the crypts due to acceleration of cell division to compensate for the loss of cells. The combined loss of microvillus border and villus height diminishes the absorptive intestinal surface and reduces uptake of fluids, electrolytes and nutrients from the gut lumen.

The pharmacokinetics of NZ-369 was first investigated in in broiler chickens. 9 male broiler chicks age 14-21 days were used in two studies, with triplicate time points. In the first study, chicks received 1-20 mg per animal (57 mg/kg) in 500 μL of 10% DMSO, 90% Canola oil by gavage. In the second study, chick received 2-40 mg per animal (117 mg/kg) in 500 μL of 10% DMSO, 90% Canola oil by gavage.

3 male broiler chicks age 14-21 days were used a a third study with triplicate time points. These chicks in the third study received 3-40 mg per animal (125 mg/kg) in a 240 mg NZ-369 plus 400 g blended bird feed for two days per cohort. These chicks consumed the feed without prejudice, with most of it being eaten on day 1 such that dosing at 24 hours was 0.9823 μg/mL and at 48 hours it was 0.3646 μg/mL.

All chicks tolerated the dose well without any obvious signs of distress, morbidity, or mortality.

To determine the effects of NZ-366 and NZ-369 on coccidiosis in broiler chicks, experimental animals were divided into 4 treatment groups: Unmedicated (UNM), those receiving the experimental compounds (366 and 369); and those receiving Salinomycin (SAL).

Compounds NZ-366 and NZ-369 were administered at a dose of 20 mg/bird by oral gavage daily beginning from 11 days post-hatching. Salinomycin was administered in-feed beginning from 10 days post-hatching. Broilers were administered a 1000x dose of coccidiosis vaccine by oral gavage at 13 days post-hatching.

Figure 7:
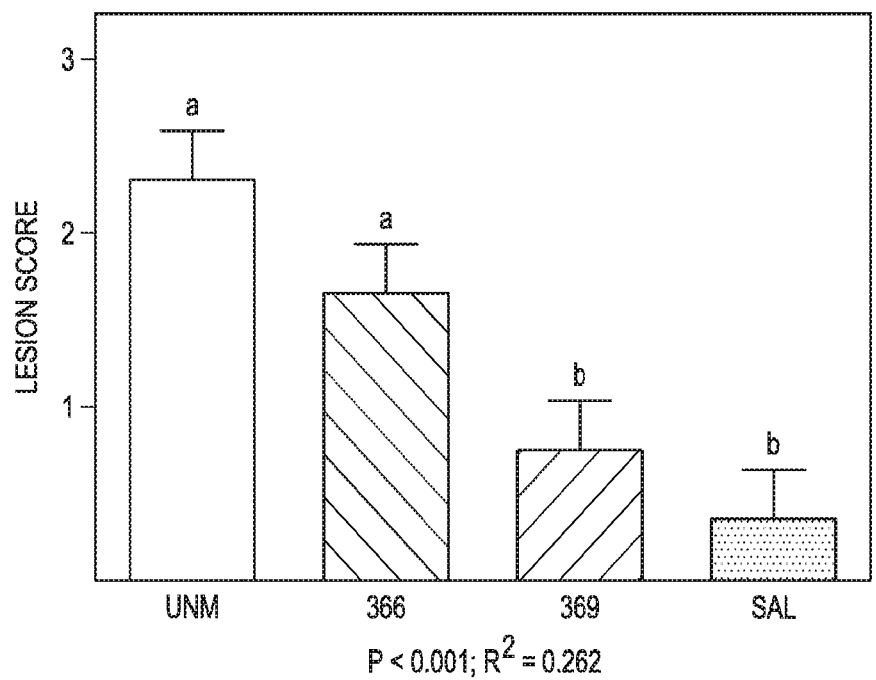
FIG. 7 is a graph of lesion scores for duodenal lesions in broiler chicks with coccidiosis that were untreated or treated with a control or test compound.

Results for duodenal lesions, which result from coccidiosis, are presented in FIG. 7. Lesion scores in the duodenum were lower in broiler chicks administered NZ-369 as compared to unmedicated broilers and those administered NZ-366. Additionally, reduction of lesion scores by NZ-369 was comparable to broiler chicks administered Salinomycin. Treatment with NZ-369 appeared to reduce lesion scores in the duodenum of broiler chicks to a level comparable to treatment with Salinomycin. The reduction in lesion scores suggests the efficacy of NZ-369 and similar compounds as anticoccidials for use in broiler chickens. In FIG. 7, lesion scores expressed as the mean±SEM from 24 broilers per treatment. Different letters indicate significantly different means as determined using Duncan's multiple range test ($P<0.05$)

Although only exemplary embodiments of the invention are specifically described above, it will be appreciated that modifications and variations of these examples are possible without departing from the spirit and intended scope of the invention. For example, various specific formulations including components not listed herein and specific methods of administering such formulations can be developed using the ordinary skill in the art. Numeric amounts expressed herein will be understood by one of ordinary skill in the art to include amounts that are approximately or about those expressed. Furthermore, the term "or" as used herein is not intended to express exclusive options (either/or) unless the context specifically indicates that exclusivity is required; rather "or" is intended to be inclusive (and/or).

The invention claimed is:

1. A method of sensitizing a parasite to a drug comprising administering an arylphenoxypropionate derivative, an aryloxyphenoxyacetate derivative, an aryloxyphenylacetate derivative, one or more substituted quinols, or a pharmaceutically acceptable salt, hydrate, or prodrug thereof, or a combination thereof to the parasite in an amount and for a time sufficient to sensitize the parasite to the drug, wherein the parasite is a species of the genus *Plasmodium*, a species of the genus *Ascaris*, a species of the genus *Enterobius*, a species of the genus *Trichinella*, a species of the genus *Haemonchus*, a species of the genus *Aphelenchoides*, a species of the genus *Ditvlenchus*, a species of the genus *Globodera*, a species of the genus *Heterodera*, a species of the genus *Longidorus*, a species of the genus *Meloidogyne*, a species of the genus *Nacobbus*, a species of the genus *Pratvlenchus*, a species of the genus *Trichodorus*, a species of the genus *Xiphinema*, a species of the genus *Bursaphelenchus*, a species of the genus *Fasciola*, a species of the genus *Coccidoides*, or a species of the genus *Onchocerca*, or the parasite is selected from the group consisting of *Pedicululs humanus, Phthiriasis pubis, Sarcoptes scabiei, Schistosoma mansoni, Schistosoma japonicum, Schistosoma haemotobium, Trichobilharzia regenti, Clonorchis simensis, Fasciola hepatica, Fasciola gigantica, Opisthorchis viverrinil, Paragonimus westermani, Paragonimus kellicotti, Fasciolopsis buski, Metagonimus vokagawai, Heterophyes heterophyes, Echinococcus granulosus, Echinococcus multilocularis, Taenia saginata, Taenia solium, Taenia asiatica, Hvmenolpeis nana, Hvmenolpeis diminuta, Diphvllobotrium latum, Diphvllobotrium mansonoides, Spirometra erinaceieuropaei, Dracunculus medinensis, Onchocerca volvulus, Lo vaginalis a loa, Mansonella*

*perstans, Mansonella ozzardi, Mansonella streptocera, Wucheria bancrofti, Brugia malavi, Brugia timori, Gnathostoma spinigerum, Gnathostoma hispidium, Ancylostoma duodenale, Ancylostoma brazilienes, Necator americanus, Angiostrongylus cantonensis, Ascaris lumbricoides, Toxocara canis, Toxocara cati, Strongyloides stercoralis, Enterobius vermicularis, Trichinella spiralis, Trichuris trichiura, Cryptosporidium hominis, Cryptosporidium parvum, Isosporiasis belli, Cyclospora cavetanesis, Balantidium coli, Entamoeba histolvtica, dispar, Giardia lamblia, Trichmonas vaginalis, Dientamoeba fragilis, Blastocystis hominis, Plasmodium falciparum, Plasmodium vivax, Plasmodium ovale, Plasmodium malariea, Babesia divergens, Babesia microfti, Trypanosoma brucei, Trypanosoma cruzi, Leishomania mexicana, Leishomania aethiopica, Leishomania tropic, Leishomania braziliensis, Leishomania donovani,* and *Leishomania infantum, Eimeria vermiformis, Eimeria brunett, Eimeria praecox, Eimeria maxima, Eimeria mitis, Eimeria necatrix* and *Eimeria tenella*.

2. The method of claim 1, further comprising administering an arylphenoxypropionate derivative, an aryloxyphenoxyacetate derivative, an aryloxyphenylacetate derivative, one or more substituted quinols, or a pharmaceutically acceptable salt, hydrate, or prodrug thereof, or a combination thereof to the parasite before administering the drug to which the parasite is sensitized.

3. The method of claim 1, further comprising administering an arylphenoxypropionate derivative, an aryloxyphenoxyacetate derivative, an aryloxyphenylacetate derivative, one or more substituted quinols, or a pharmaceutically acceptable salt, hydrate, or prodrug thereof, or a combination thereof to the parasite concurrently with the drug to which the parasite is sensitized.

4. The method of claim 1, further comprising administering an arylphenoxypropionate derivative, an aryloxyphenoxyacetate derivative, an aryloxyphenylacetate derivative, one or more substituted quinols, or a pharmaceutically acceptable salt, hydrate, or prodrug thereof, or a combination thereof to the parasite after administering the drug to which the parasite is sensitized.

5. The method of claim 1, further comprising administering an arylphenoxypropionate derivative, an aryloxyphenoxyacetate derivative, an aryloxyphenylacetate derivative, one or more substituted quinols, or a pharmaceutically acceptable salt, hydrate, or prodrug thereof, or a combination thereof to the parasite a second or greater time.

6. The method of claim 1, wherein administering an arylphenoxypropionate derivative, an aryloxyphenoxyacetate derivative, an aryloxyphenylacetate derivative, one or more substituted quinols, or a pharmaceutically acceptable salt, hydrate, or prodrug thereof, or a combination thereof to the parasite in an amount and for a time sufficient to sensitize the parasite to the drug comprises rendering the parasite susceptible to the drug at a lower dose than in the absence of an arylphenoxypropionate derivative, an aryloxyphenoxyacetate derivative, an aryloxyphenylacetate derivative, one or more substituted quinols, or a pharmaceutically acceptable salt, hydrate, or prodrug thereof, or a combination thereof.

7. The method of claim 1, wherein administering an arylphenoxypropionate derivative, an aryloxyphenoxyacetate derivative, an aryloxyphenylacetate derivative, one or more substituted quinols, or a pharmaceutically acceptable salt, hydrate, or prodrug thereof, or a combination thereof to the parasite in an amount and for a time sufficient to sensitize the parasite to the drug comprises rendering the parasite susceptible to a drug that the parasite would not be susceptible to in the absence of an arylphenoxypropionate derivative, an aryloxyphenoxyacetate derivative, an aryloxyphenylacetate derivative, one or more substituted quinols, or a pharmaceutically acceptable salt, hydrate, or prodrug thereof, or a combination thereof.

8. The method of claim 1, wherein the drug comprises an antiparasitic drug and wherein administering arylphenoxypropionate derivative, an aryloxyphenoxyacetate derivative, an aryloxyphenylacetate derivative, one or more substituted quinols, or a pharmaceutically acceptable salt, hydrate, or prodrug thereof, or a combination thereof to the parasite in an amount and for a time sufficient to sensitize the parasite to the drug comprises rendering the parasite susceptible to death or a decrease in growth due to the antiparasitic drug.

* * * * *